United States Patent
Widmaier et al.

(10) Patent No.: US 9,963,554 B2
(45) Date of Patent: *May 8, 2018

(54) METHODS AND COMPOSITIONS FOR SYNTHESIZING IMPROVED SILK FIBERS

(71) Applicant: Bolt Threads, Inc., Emeryville, CA (US)

(72) Inventors: Daniel M. Widmaier, San Francisco, CA (US); David N. Breslauer, San Francisco, CA (US); Joshua Kittleson, Berkeley, CA (US); Brendan Turner, El Cerrito, CA (US); Lindsay Wray, Fairfield, CA (US)

(73) Assignee: Bolt Threads, Inc., Emeryville, CA (US)

(*) Notice: Subject to any disclaimer, the term of this patent is extended or adjusted under 35 U.S.C. 154(b) by 0 days. days.

This patent is subject to a terminal disclaimer.

(21) Appl. No.: 15/073,514

(22) Filed: Mar. 17, 2016

(65) Prior Publication Data
US 2016/0222174 A1    Aug. 4, 2016

Related U.S. Application Data

(63) Continuation of application No. PCT/US2014/056117, filed on Sep. 17, 2014.

(60) Provisional application No. 61/878,858, filed on Sep. 17, 2013.

(51) Int. Cl.
| | |
|---|---|
| C12P 21/02 | (2006.01) |
| C07H 1/00 | (2006.01) |
| C08H 1/00 | (2006.01) |
| D01F 4/00 | (2006.01) |
| D01F 4/02 | (2006.01) |
| D01F 6/68 | (2006.01) |
| C07K 14/435 | (2006.01) |
| C12P 21/00 | (2006.01) |

(52) U.S. Cl.
CPC ......... *C08H 1/00* (2013.01); *C07K 14/43518* (2013.01); *C07K 14/43586* (2013.01); *C12P 21/00* (2013.01); *C12P 21/02* (2013.01); *D01F 4/00* (2013.01); *D01F 4/02* (2013.01); *D01F 6/68* (2013.01); *C07K 2319/02* (2013.01)

(58) Field of Classification Search
None
See application file for complete search history.

(56) References Cited

U.S. PATENT DOCUMENTS

| | | | |
|---|---|---|---|
| 5,171,505 A | 12/1992 | Lock | |
| 7,057,023 B2 | 6/2006 | Islam et al. | |
| 2005/0010035 A1 | 1/2005 | Lewis et al. | |
| 2005/0054830 A1 | 3/2005 | Islam et al. | |
| 2007/0260039 A1 | 11/2007 | Karatzas et al. | |
| 2010/0068517 A1 | 3/2010 | Liu et al. | |
| 2010/0222553 A1 | 9/2010 | Hayashi et al. | |
| 2012/0041177 A1 | 2/2012 | Johansson et al. | |
| 2013/0109762 A1 | 5/2013 | Lammel et al. | |
| 2013/0212718 A1 | 8/2013 | Fraser et al. | |
| 2014/0058066 A1 | 2/2014 | Sekiyama et al. | |
| 2014/0128991 A1 | 5/2014 | Atanasoska et al. | |
| 2014/0194603 A1 | 7/2014 | Lehmann et al. | |
| 2015/0047532 A1 | 2/2015 | Lewis et al. | |

FOREIGN PATENT DOCUMENTS

| | | |
|---|---|---|
| WO | WO 02/099082 A2 | 12/2002 |
| WO | WO 03/020916 A2 | 3/2003 |
| WO | WO 2003/057727 A1 | 7/2003 |
| WO | WO 2012/050919 A2 | 4/2012 |
| WO | WO 2012/055854 A2 | 5/2012 |
| WO | WO 2013/180767 A2 | 12/2013 |
| WO | WO 2016/149414 A1 | 9/2016 |

OTHER PUBLICATIONS

Hopp et al., Nature Biotechnology, 6:1204-1210, 1988.*
Collins, T. et al., "Batch Production of a Silk-Elastin-Like Protein in E. col. BL21(DE3): Key Parameters for Optimisation," Microbial Cell Factories, Feb. 27, 2013, pp. 1-16, vol. 12, No. 21.
Elices, M. et al., "Bioinspired Fibers Follow the Track of Natural Spider Silk." Macromolecules, 2011, pp. 1166-1176, vol. 44.
Guerette, P.A. et al., "Silk Properties Determined by Gland-Specific Expression of a Spider Fibroin Gene Family." Science, Apr. 5, 1996, pp. 112-115, vol. 272, No. 5258.
Paal, M. et al., "A Novel Ecotin-Ubiquitin-Tag (ECUT) for Efficient, Soluble Peptide Production in the Periplasm of *Escherichia coli*," Microbial Cell Factories, Jan. 21, 2009, pp. 1-9, vol. 8, No. 7.
PCT Invitation to Pay Additional Fees, PCT Application No. PCT/US14/56117, dated Jan. 14, 2015, 3 pages.
PCT International Search Report and Written Opinion, PCT Application No. PCT/US14/56117, dated Mar. 10, 2015, 26 pages.
Xia, X. et al., "Native-Sized Recombinant Spider Silk Protein Produced in Metabolically Engineered *Escherichia coli* Results in a Strong Fiber," Proc. Natl. Acad. Sci., 2010, pp. 14059-14063, vol. 107, No. 32.
PCT International Search Report and Written Opinion, PCT Application No. PCT/US16/22707, dated Jul. 12, 2016, 17 pages.
European Extended Search Report, European Application No. 14846179.1, dated Feb. 24, 2017, 11 pages.
Database Accession No. I6YNT3, "SubName: Full=Major Ampullate Silk Protein 2 {ECO:0000313| ENBL:AFN54363.1}," Retrieved from EBI Accession No. UNIPROT:I6YNT3, Oct. 3, 2012, 1 page.

(Continued)

*Primary Examiner* — Nancy A Treptow

(74) *Attorney, Agent, or Firm* — Fenwick & West LLP

(57) ABSTRACT

The present disclosure provides methods and compositions for directed to synthetic block copolymer proteins, expression constructs for their secretion, recombinant microorganisms for their production, and synthetic fibers (including advantageously, microfibers) comprising these proteins that recapitulate many properties of natural silk. The recombinant microorganisms can be used for the commercial production of silk-like fibers.

11 Claims, 21 Drawing Sheets

(56) References Cited

OTHER PUBLICATIONS

Zhang, Y. et al., "The Molecular Structures of Major Ampullate Silk Proteins of the Wasp Spider, *Argiope bruennichi*: A Second Blueprint for Synthesizing De Novo Silk," Comparative Biochemistry and Physiology Part B: Biochemistry and Molecular Biology, Elsevier, Dec. 20, 2012, pp. 151-158, vol. 164, No. 3.
Bliven, S. et al., "Circular Permutation in Proteins," PLOS Computational Biology, Mar. 2012, pp. 1-5, vol. 8, Issue 3, e1002445.

\* cited by examiner

METHODS AND COMPOSITIONS FOR SYNTHESIZING IMPROVED SILK FIBERS

CROSS-REFERENCE TO RELATED APPLICATIONS

This application is a continuation of co-pending International Application No. PCT/US2014/056117, filed Sep. 17, 2014, which claims benefit of U.S. Provisional Application No. 61/878,858, filed on Sep. 17, 2013, both of which are hereby incorporated by reference in their entirety for all purposes.

SEQUENCE LISTING

The instant application contains a Sequence Listing which has been submitted electronically in ASCII format and is hereby incorporated by reference in its entirety. Said ASCII copy, created on Sep. 16, 2014, is named 27321PCT_CRF_SequenceListing.txt and is 4,189,730 bytes in size.

FIELD OF THE INVENTION

The present disclosure relates to methods and compositions directed to synthetic block copolymer proteins, expression constructs for their secretion, recombinant microorganisms for their production, and synthetic fibers comprising these proteins that recapitulate many properties of natural silk.

BACKGROUND OF THE INVENTION

Spider's silk polypeptides are large (>150 kDa, >1000 amino acids) polypeptides that can be broken down into three domains: an N-terminal non-repetitive domain (NTD), the repeat domain (REP), and the C-terminal non-repetitive domain (CTD). The NTD and CTD are relatively small (~150, ~100 amino acids respectively), well-studied, and are believed to confer to the polypeptide aqueous stability, pH sensitivity, and molecular alignment upon aggregation. NTD also has a strongly predicted secretion tag, which is often removed during heterologous expression. The repetitive region composes ~90% of the natural polypeptide, and folds into the crystalline and amorphous regions that confer strength and flexibility to the silk fiber, respectively.

Silk polypeptides come from a variety of sources, including bees, moths, spiders, mites, and other arthropods. Some organisms make multiple silk fibers with unique sequences, structural elements, and mechanical properties. For example, orb weaving spiders have six unique types of glands that produce different silk polypeptide sequences that are polymerized into fibers tailored to fit an environmental or lifecycle niche. The fibers are named for the gland they originate from and the polypeptides are labeled with the gland abbreviation (e.g. "Ma") and "Sp" for spidroin (short for spider fibroin). In orb weavers, these types include Major Ampullate (MaSp, also called dragline), Minor Ampullate (MiSp), Flagelliform (Flag), Aciniform (AcSp), Tubuliform (TuSp), and Pyriform (PySp). This combination of polypeptide sequences across fiber types, domains, and variation amongst different genus and species of organisms leads to a vast array of potential properties that can be harnessed by commercial production of the recombinant fibers. To date, the vast majority of the work with recombinant silks has focused on the Major Ampullate Spidroins (MaSp).

Currently, recombinant silk fibers are not commercially available and, with a handful of exceptions, are not produced in microorganisms outside of *Escherichia coli* and other gram-negative prokaryotes. Recombinant silks produced to date have largely consisted either of polymerized short silk sequence motifs or fragments of native repeat domains, sometimes in combination with NTDs and/or CTDs. This has resulted in the production of small scales of recombinant silk polypeptides (milligrams at lab scale, kilograms at bioprocessing scale) produced using intracellular expression and purification by chromatography or bulk precipitation. These methods do not lead to viable commercial scalability that can compete with the price of existing technical and textile fibers. Additional production hosts that have been utilized to make silk polypeptides include transgenic goats, transgenic silkworms, and plants. These hosts have yet to enable commercial scale production of silk, presumably due to slow engineering cycles and poor scalability.

Microfibers are a classification of fibers having a fineness of less than 1 decitex (dtex), approximately 10 µm in diameter. H. K., Kaynak and O. Babaarslan, Woven Fabrics, Croatia: InTech, 2012. The small diameter of microfibers imparts a range of qualities and characteristics to microfiber yarns and fabrics that are desirable to consumers. Microfibers are inherently more flexible (bending is inversely proportional to fiber diameter) and thus have a soft feel, low stiffness, and high drapeability. Microfibers can also be spun into yarns having high fiber density (greater fibers per yarn cross-sectional area), giving microfiber yarns a higher strength compared to other yarns of similar dimensions. Microfibers also contribute to discrete stress relief within the yarn, resulting in anti-wrinkle fabrics. Furthermore, microfibers have high compaction efficiency within the yarn, which improves fabric waterproofness and windproofness while maintaining breathability compared to other waterproofing and windproofing techniques (such as polyvinyl coatings). The high density of fibers within microfiber fabrics results in microchannel structures between fibers, which promotes the capillary effect and imparts a wicking and quick drying characteristic. The high surface area to volume of microfiber yarns allows for brighter and sharper dyeing, and printed fabrics have clearer and sharper pattern retention as well. Currently, recombinant silk fibers do not have a fineness that is small enough to result in silks having microfiber type characteristics. U.S. Pat. App. Pub. No. 2014/0058066 generally discloses fiber diameters between 5-100 µm, but does not actually disclose any working examples of any fiber having a diameter as small as 5 µm.

What is needed, therefore, are improved methods and compositions relating to of recombinant block copolymer proteins, expression constructs for their secretion at high rates, microorganisms expressing these proteins and synthetic fibers made from these proteins that recapitulate many of the properties of silk fibers, including fibers having small diameters useful for microfiber textiles.

SUMMARY OF THE INVENTION

The invention provides compositions of proteinaceous block co-polymers capable of assembling into fibers, and methods of producing said co-polymers. A proteinaceous block co-polymer comprises a quasi-repeat domain, the co-polymer capable of assembling into a fiber. In some embodiments the co-polymer comprises an alanine composition of 12-40% of the amino acid sequence of the co-polymer, a glycine composition of 25-50% of the amino acid sequence of the co-polymer, a proline composition of 9-20% of the amino acid sequence of the co-polymer, a β-turn composition of 15-37% of the amino acid sequence of the co-polymer, a GPG amino acid motif content of 18-55% of the amino acid sequence of the co-polymer, and a poly alanine amino acid motif content of 9-35% of all amino acids of the co-polymer.

In some embodiments, the co-polymer also includes an N-terminal non-repetitive domain between 75-350 amino acids in length, and a C-terminal non-repetitive domain between 75-350 amino acids in length. In some embodiments, the quasi-repeat domain is 500-5000, 119-1575, or 900-950 amino acids in length. In other embodiments, the mass of the co-polymer is 40-400, 12.2-132, or 70-100 kDa. In some embodiments, the alanine composition is 16-31% or 15-20% of the amino acid sequence of the co-polymer. In other embodiments, the glycine composition is 29-43% or 38-43% of the amino acid sequence of the co-polymer. In some embodiments, the proline composition is 11-16% or 13-15% of the amino acid sequence of the co-polymer. In other embodiments, the β-turn composition is 18-33% or 25-30% of the amino acid sequence of the co-polymer. In some embodiments, the GPG amino acid motif content is 22-47% or 30-45% of the amino acid sequence of the co-polymer. In other embodiments, the poly alanine amino acid motif content is 12-29% of the amino acid sequence of the co-polymer. In some embodiments, the co-polymer comprises a sequence from Table 13a, SEQ ID NO: 1396, or SEQ ID NO: 1374. In other embodiments, the co-polymer consists of SEQ ID NO: 1398 or SEQ ID NO: 2770.

In some embodiments, an engineered microorganism comprises a heterologous nucleic acid molecule encoding a secretion signal and a coding sequence, the coding sequence encoding the co-polymer described above, wherein the secretion signal allows for secretion of the co-polymer from the microorganism. In further embodiments, the engineered microorganism is *Pichia pastoris* or *Bacillus subtilis*. In other embodiments, a cell culture comprises a culture medium and the engineered microorganism. In other embodiments, a method of producing a secreted block co-polymer comprises obtaining the cell culture medium and maintaining the cell culture medium under conditions that result in the engineered microorganism secreting the co-polymer at a rate of at least 2-20 mg silk/g DCW/hour. In further embodiments, the co-polymer is secreted at a rate of at least 20 mg silk/g DCW/hour. In yet other embodiments, a cell culture medium comprises a secreted co-polymer as described above.

In other embodiments, the invention includes a method for producing a fiber comprises obtaining the cell culture medium as described above, isolating the secreted protein, and processing the protein into a spinnable solution and producing a fiber from the spinnable solution. In some embodiments, a fiber comprises a secreted co-polymer as described above. In some embodiments, the fiber has a yield stress of 24-172 or 150-172 MPa. In other embodiments, the fiber has a maximum stress of 54-310 or 150-310 MPa. In some embodiments, the fiber has a breaking strain of 2-200% or 180-200%. In other embodiments, the fiber has a diameter of 4.48-12.7 or 4-5 µm. In some embodiments, the fiber has an initial modulus of 1617-5820 or 5500-5820 MPa. In other embodiments, the fiber has a toughness value of at least 0.5, 3.1, or 59.2 MJ/m$^3$. In still other embodiments, the fiber has a fineness between 0.2-0.6 denier.

These and other embodiments of the invention are further described in the Figures, Description, Examples and Claims, herein.

BRIEF DESCRIPTION OF THE FIGURES

FIG. 1 discloses "AAAAAA" as SEQ ID NO: 2838.

FIG. 8 discloses SEQ ID NOs: 2839-2842 and 2841-2843, respectively, in order of appearance.

DETAILED DESCRIPTION OF THE INVENTION

Figure 1:
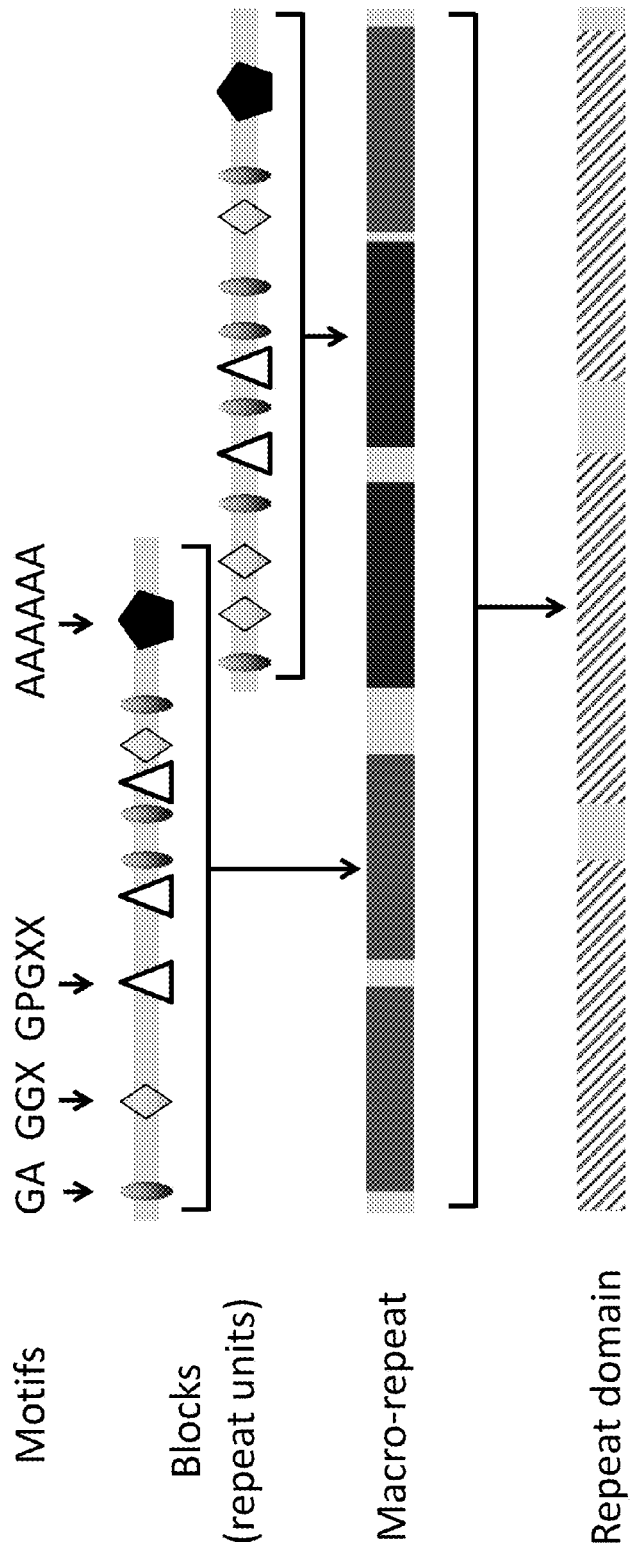
FIG. 1 depicts the hierarchical architecture of silk polypeptide sequences, including the block copolymeric structure of natural silk polypeptides.

Unless otherwise defined herein, scientific and technical terms used in connection with the present invention shall have the meanings that are commonly understood by those of ordinary skill in the art. Further, unless otherwise required by context, singular terms shall include the plural and plural terms shall include the singular. Generally, nomenclatures used in connection with, and techniques of, biochemistry, enzymology, molecular and cellular biology, microbiology, genetics and polypeptide and nucleic acid chemistry and hybridization described herein are those well known and commonly used in the art.

The methods and techniques of the present invention are generally performed according to conventional methods well known in the art and as described in various general and more specific references that are cited and discussed throughout the present specification unless otherwise indicated. See, e.g., Sambrook et al., *Molecular Cloning: A Laboratory Manual*, 2d ed., Cold Spring Harbor Laboratory Press, Cold Spring Harbor, N.Y. (1989); Ausubel et al., *Current Protocols in Molecular Biology*, Greene Publishing Associates (1992, and Supplements to 2002); Harlow and Lane, *Antibodies: A Laboratory Manual*, Cold Spring Harbor Laboratory Press, Cold Spring Harbor, N.Y. (1990); Taylor and Drickamer, *Introduction to Glycobiology*, Oxford Univ. Press (2003); *Worthington Enzyme Manual*, Worthington Biochemical Corp., Freehold, N.J.; *Handbook of Biochemistry: Section A Proteins*, Vol I, CRC Press (1976); Handbook of Biochemistry: Section A Proteins, Vol II, CRC Press (1976); *Essentials of Glycobiology*, Cold Spring Harbor Laboratory Press (1999).

All publications, patents and other references mentioned herein are hereby incorporated by reference in their entireties.

The following terms, unless otherwise indicated, shall be understood to have the following meanings:

The term "polynucleotide" or "nucleic acid molecule" refers to a polymeric form of nucleotides of at least 10 bases in length. The term includes DNA molecules (e.g., cDNA or genomic or synthetic DNA) and RNA molecules (e.g., mRNA or synthetic RNA), as well as analogs of DNA or RNA containing non-natural nucleotide analogs, non-native internucleoside bonds, or both. The nucleic acid can be in any topological conformation. For instance, the nucleic acid can be single-stranded, double-stranded, triple-stranded, quadruplexed, partially double-stranded, branched, hairpinned, circular, or in a padlocked conformation.

Unless otherwise indicated, and as an example for all sequences described herein under the general format "SEQ ID NO:", "nucleic acid comprising SEQ ID NO:1" refers to a nucleic acid, at least a portion of which has either (i) the sequence of SEQ ID NO:1, or (ii) a sequence complementary to SEQ ID NO:1. The choice between the two is dictated by the context. For instance, if the nucleic acid is used as a probe, the choice between the two is dictated by the requirement that the probe be complementary to the desired target.

An "isolated" RNA, DNA or a mixed polymer is one which is substantially separated from other cellular components that naturally accompany the native polynucleotide in its natural host cell, e.g., ribosomes, polymerases and genomic sequences with which it is naturally associated.

The term "recombinant" refers to a biomolecule, e.g., a gene or polypeptide, that (1) has been removed from its naturally occurring environment, (2) is not associated with all or a portion of a polynucleotide in which the gene is found in nature, (3) is operatively linked to a polynucleotide which it is not linked to in nature, or (4) does not occur in nature. The term "recombinant" can be used in reference to cloned DNA isolates, chemically synthesized polynucleotide analogs, or polynucleotide analogs that are biologically synthesized by heterologous systems, as well as polypeptides and/or mRNAs encoded by such nucleic acids.

As used herein, an endogenous nucleic acid sequence in the genome of an organism (or the encoded polypeptide product of that sequence) is deemed "recombinant" herein if a heterologous sequence is placed adjacent to the endogenous nucleic acid sequence, such that the expression of this endogenous nucleic acid sequence is altered. In this context, a heterologous sequence is a sequence that is not naturally adjacent to the endogenous nucleic acid sequence, whether or not the heterologous sequence is itself endogenous (originating from the same host cell or progeny thereof) or exogenous (originating from a different host cell or progeny thereof). By way of example, a promoter sequence can be substituted (e.g., by homologous recombination) for the native promoter of a gene in the genome of a host cell, such that this gene has an altered expression pattern. This gene would now become "recombinant" because it is separated from at least some of the sequences that naturally flank it. In an embodiment, a heterologous nucleic acid molecule is not endogenous to the organism. In further embodiments, a heterologous nucleic acid molecule is a plasmid or molecule integrated into a host chromosome by homologous or random integration.

A nucleic acid is also considered "recombinant" if it contains any modifications that do not naturally occur to the corresponding nucleic acid in a genome. For instance, an endogenous coding sequence is considered "recombinant" if it contains an insertion, deletion or a point mutation introduced artificially, e.g., by human intervention. A "recombinant nucleic acid" also includes a nucleic acid integrated into a host cell chromosome at a heterologous site and a nucleic acid construct present as an episome.

As used herein, the phrase "degenerate variant" of a reference nucleic acid sequence encompasses nucleic acid sequences that can be translated, according to the standard genetic code, to provide an amino acid sequence identical to that translated from the reference nucleic acid sequence. The term "degenerate oligonucleotide" or "degenerate primer" is used to signify an oligonucleotide capable of hybridizing with target nucleic acid sequences that are not necessarily identical in sequence but that are homologous to one another within one or more particular segments.

The term "percent sequence identity" or "identical" in the context of nucleic acid sequences refers to the residues in the two sequences which are the same when aligned for maximum correspondence. The length of sequence identity comparison may be over a stretch of at least about nine nucleotides, usually at least about 20 nucleotides, more usually at least about 24 nucleotides, typically at least about 28 nucleotides, more typically at least about 32 nucleotides, and preferably at least about 36 or more nucleotides. There are a number of different algorithms known in the art which can be used to measure nucleotide sequence identity. For instance, polynucleotide sequences can be compared using FASTA, Gap or Bestfit, which are programs in Wisconsin Package Version 10.0, Genetics Computer Group (GCG), Madison, Wis. FASTA provides alignments and percent sequence identity of the regions of the best overlap between the query and search sequences. Pearson, Methods Enzymol. 183:63-98 (1990) (hereby incorporated by reference in its entirety). For instance, percent sequence identity between nucleic acid sequences can be determined using FASTA with its default parameters (a word size of 6 and the NOPAM factor for the scoring matrix) or using Gap with its default parameters as provided in GCG Version 6.1, herein incorporated by reference. Alternatively, sequences can be compared using the computer program, BLAST (Altschul et al., J. Mol. Biol. 215:403-410 (1990); Gish and States, Nature Genet. 3:266-272 (1993); Madden et al., Meth. Enzymol. 266:131-141 (1996); Altschul et al., Nucleic Acids Res. 25:3389-3402 (1997); Zhang and Madden, Genome Res. 7:649-656 (1997)), especially blastp or tblastn (Altschul et al., Nucleic Acids Res. 25:3389-3402 (1997)).

The term "substantial homology" or "substantial similarity," when referring to a nucleic acid or fragment thereof, indicates that, when optimally aligned with appropriate nucleotide insertions or deletions with another nucleic acid (or its complementary strand), there is nucleotide sequence identity in at least about 76%, 80%, 85%, preferably at least about 90%, and more preferably at least about 95%, 96%, 97%, 98% or 99% of the nucleotide bases, as measured by any well-known algorithm of sequence identity, such as FASTA, BLAST or Gap, as discussed above.

The nucleic acids (also referred to as polynucleotides) of this present invention can include both sense and antisense strands of RNA, cDNA, genomic DNA, and synthetic forms and mixed polymers of the above. They can be modified chemically or biochemically or may contain non-natural or derivatized nucleotide bases, as will be readily appreciated by those of skill in the art. Such modifications include, for example, labels, methylation, substitution of one or more of the naturally occurring nucleotides with an analog, internucleotide modifications such as uncharged linkages (e.g., methyl phosphonates, phosphotriesters, phosphoramidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha anomeric nucleic acids, etc.) Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule. Other modifications can include, for example, analogs in which the ribose ring contains a bridging moiety or other structure such as the modifications found in "locked" nucleic acids.

The term "mutated" when applied to nucleic acid sequences means that nucleotides in a nucleic acid sequence may be inserted, deleted or changed compared to a reference nucleic acid sequence. A single alteration may be made at a locus (a point mutation) or multiple nucleotides may be inserted, deleted or changed at a single locus. In addition, one or more alterations may be made at any number of loci within a nucleic acid sequence. A nucleic acid sequence may be mutated by any method known in the art including but not limited to mutagenesis techniques such as "error-prone PCR" (a process for performing PCR under conditions where the copying fidelity of the DNA polymerase is low, such that a high rate of point mutations is obtained along the entire length of the PCR product; see, e.g., Leung et al., Technique, 1:11-15 (1989) and Caldwell and Joyce, PCR Methods Applic. 2:28-33 (1992)); and "oligonucleotide-directed mutagenesis" (a process which enables the generation of site-specific mutations in any cloned DNA segment of interest; see, e.g., Reidhaar-Olson and Sauer, Science 241:53-57 (1988)).

The term "vector" as used herein is intended to refer to a nucleic acid molecule capable of transporting another nucleic acid to which it has been linked. One type of vector is a "plasmid," which generally refers to a circular double stranded DNA loop into which additional DNA segments may be ligated, but also includes linear double-stranded molecules such as those resulting from amplification by the polymerase chain reaction (PCR) or from treatment of a circular plasmid with a restriction enzyme. Other vectors include cosmids, bacterial artificial chromosomes (BAC) and yeast artificial chromosomes (YAC). Another type of vector is a viral vector, wherein additional DNA segments may be ligated into the viral genome (discussed in more detail below). Certain vectors are capable of autonomous replication in a host cell into which they are introduced (e.g., vectors having an origin of replication which functions in the host cell). Other vectors can be integrated into the genome of a host cell upon introduction into the host cell, and are thereby replicated along with the host genome. Moreover, certain preferred vectors are capable of directing the expression of genes to which they are operatively linked. Such vectors are referred to herein as "recombinant expression vectors" (or simply "expression vectors").

The term "expression system" as used herein includes vehicles or vectors for the expression of a gene in a host cell as well as vehicles or vectors which bring about stable integration of a gene into the host chromosome.

"Operatively linked" or "operably linked" expression control sequences refers to a linkage in which the expression control sequence is contiguous with the gene of interest to control the gene of interest, as well as expression control sequences that act in trans or at a distance to control the gene of interest.

The term "expression control sequence" as used herein refers to polynucleotide sequences which are necessary to affect the expression of coding sequences to which they are operatively linked. Expression control sequences are sequences which control the transcription, post-transcriptional events and translation of nucleic acid sequences. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (e.g., ribosome binding sites); sequences that enhance polypeptide stability; and when desired, sequences that enhance polypeptide secretion. The nature of such control sequences differs depending upon the host organism; in prokaryotes, such control sequences generally include promoter, ribosomal binding site, and transcription termination sequence. The term "control sequences" is intended to include, at a minimum, all components whose presence is essential for expression, and can also include additional components whose presence is advantageous, for example, leader sequences and fusion partner sequences.

The term "promoter," as used herein, refers to a DNA region to which RNA polymerase binds to initiate gene transcription, and positions at the 5' direction of an mRNA transcription initiation site.

The term "recombinant host cell" (or simply "host cell"), as used herein, is intended to refer to a cell into which a recombinant vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein. A recombinant host cell may be an isolated cell or cell line grown in culture or may be a cell which resides in a living tissue or organism.

The term "peptide" as used herein refers to a short polypeptide, e.g., one that is typically less than about 50 amino acids long and more typically less than about 30 amino acids long. The term as used herein encompasses analogs and mimetics that mimic structural and thus biological function.

The term "polypeptide" encompasses both naturally-occurring and non-naturally-occurring proteins, and fragments, mutants, derivatives and analogs thereof. A polypeptide may be monomeric or polymeric. Further, a polypeptide may comprise a number of different domains each of which has one or more distinct activities.

As used herein, the term "molecule" means any compound, including, but not limited to, a small molecule, peptide, polypeptide, sugar, nucleotide, nucleic acid, polynucleotide, lipid, etc., and such a compound can be natural or synthetic.

The term "block" or "repeat unit" as used herein refers to a subsequence greater than approximately 12 amino acids of a natural silk polypeptide that is found, possibly with modest variations, repeatedly in said natural silk polypeptide sequence and serves as a basic repeating unit in said silk polypeptide sequence. Examples can be found in Table 1. Further examples of block amino acid sequences can be found in SEQ ID NOs: 1515-2156. Blocks may, but do not necessarily, include very short "motifs." A "motif" as used herein refers to an approximately 2-10 amino acid sequence that appears in multiple blocks. For example, a motif may consist of the amino acid sequence GGA, GPG, or AAAAA (SEQ ID NO: 2803). A sequence of a plurality of blocks is a "block co-polymer."

As used herein, the term "repeat domain" refers to a sequence selected from the set of contiguous (unbroken by a substantial non-repetitive domain, excluding known silk spacer elements) repetitive segments in a silk polypeptide. Native silk sequences generally contain one repeat domain. In some embodiments of the present invention, there is one repeat domain per silk molecule. A "macro-repeat" as used herein is a naturally occurring repetitive amino acid sequence comprising more than one block. In an embodiment, a macro-repeat is repeated at least twice in a repeat domain. In a further embodiment, the two repetitions are imperfect. A "quasi-repeat" as used herein is an amino acid sequence comprising more than one block, such that the blocks are similar but not identical in amino acid sequence.

A "repeat sequence" or "R" as used herein refers to a repetitive amino acid sequence. Examples include the nucleotide sequences of SEQ ID NOs: 1-467, the nucleotide sequences with flanking sequences for cloning of SEQ ID NOs: 468-931, and the amino acid sequences of SEQ ID NOs: 932-1398. In an embodiment, a repeat sequence includes a macro-repeat or a fragment of a macro-repeat. In another embodiment, a repeat sequence includes a block. In a further embodiment, a single block is split across two repeat sequences.

Any ranges disclosed herein are inclusive of the extremes of the range. For example, a range of 2-5% includes 2% and 5%, and any number or fraction of a number in between, for example: 2.25%, 2.5%, 2.75%, 3%, 3.25%, 3.5%, 3.75%, 4%, 4.25%, 4.5%, and 4.75%.

Unless otherwise defined, all technical and scientific terms used herein have the same meaning as commonly understood by one of ordinary skill in the art to which this present invention pertains. Exemplary methods and materials are described below, although methods and materials similar or equivalent to those described herein can also be used in the practice of the present invention and will be apparent to those of skill in the art. All publications and other references mentioned herein are incorporated by reference in their entirety. In case of conflict, the present specification, including definitions, will control. The materials, methods, and examples are illustrative only and not intended to be limiting.

Throughout this specification and claims, the word "comprise" or variations such as "comprises" or "comprising," will be understood to imply the inclusion of a stated integer or group of integers but not the exclusion of any other integer or group of integers.

Silk Sequences

In some embodiments disclosed herein are 1) block copolymer polypeptide compositions generated by mixing and matching repeat domains derived from silk polypeptide sequences and 2) recombinant expression of block copolymer polypeptides having sufficiently large size (approximately 40 kDa) to form useful fibers by secretion from an industrially scalable microorganism. We provide herein the ability to produce relatively large (approximately 40 kDa to approximately 100 kDa) block copolymer polypeptides engineered from silk repeat domain fragments in a scalable engineered microorganism host, including sequences from almost all published amino acid sequences of spider silk polypeptides. In some embodiments, silk polypeptide sequences are matched and designed to produce highly expressed and secreted polypeptides capable of fiber formation.

Provided herein, in several embodiments, are compositions for expression and secretion of block copolymers engineered from a combinatorial mix of silk polypeptide domains across the silk polypeptide sequence space. In some embodiments provided herein are methods of secreting block copolymers in scalable organisms (e.g., yeast, fungi, and gram positive bacteria). In some embodiments, the block copolymer polypeptide comprises 0 or more N-terminal domains (NTD), 1 or more repeat domains (REP), and 0 or more C-terminal domains (CTD). In some aspects of the embodiment, the block copolymer polypeptide is >100 amino acids of a single polypeptide chain. In some embodiments, the block copolymer polypeptide comprises a domain that is at least 80%, 81%, 82%, 83%, 84%, 85%, 86%, 87%, 88%, 89%, 90%, 91%, 92%, 93%, 94%, 95%, 96%, 97%, 98%, or 99% identical to a sequence of SEQ ID NOs: 932-1398.

Several types of native spider silks have been identified. The mechanical properties of each natively spun silk type are believed to be closely connected to the molecular composition of that silk. See, e.g., Garb, J. E., et al., Untangling spider silk evolution with spidroin terminal domains, *BMC Evol. Biol.*, 10:243 (2010); Bittencourt, D., et al., Protein families, natural history and biotechnological aspects of spider silk, *Genet. Mol. Res.*, 11:3 (2012); Rising, A., et al., Spider silk proteins: recent advances in recombinant production, structure-function relationships and biomedical applications, *Cell. Mol. Life Sci.*, 68:2, pg. 169-184 (2011); and Humenik, M., et al., Spider silk: understanding the structure-function relationship of a natural fiber, *Prog. Mol. Biol. Transl. Sci.*, 103, pg. 131-85 (2011). For example:

Aciniform (AcSp) silks tend to have high toughness, a result of moderately high strength coupled with moderately high extensibility. AcSp silks are characterized by large block ("ensemble repeat") sizes that often incorporate motifs of poly serine and GPX. Tubuliform (TuSp or Cylindrical) silks tend to have large diameters, with modest strength and high extensibility. TuSp silks are characterized by their poly serine and poly threonine content, and short tracts of poly alanine. Major Ampullate (MaSp) silks tend to have high strength and modest extensibility. MaSp silks can be one of two subtypes: MaSp1 and MaSp2. MaSp1 silks are generally less extensible than MaSp2 silks, and are characterized by poly alanine, GX, and GGX motifs. MaSp2 silks are characterized by poly alanine, GGX, and GPX motifs. Minor Ampullate (MiSp) silks tend to have modest strength and modest extensibility. MiSp silks are characterized by GGX, GA, and poly A motifs, and often contain spacer elements of approximately 100 amino acids. Flagelliform (Flag) silks tend to have very high extensibility and modest strength. Flag silks are usually characterized by GPG, GGX, and short spacer motifs.

The properties of each silk type can vary from species to species, and spiders leading distinct lifestyles (e.g. sedentary web spinners vs. vagabond hunters) or that are evolutionarily older may produce silks that differ in properties from the above descriptions (for descriptions of spider diversity and classification, see Hormiga, G., and Griswold, C. E., Systematics, phylogeny, and evolution of orb-weaving spiders, *Annu. Rev. Entomol.* 59, pg. 487-512 (2014); and Blackedge, T. A. et al., Reconstructing web evolution and spider diversification in the molecular era, *Proc. Natl. Acad. Sci. U.S.A.*, 106:13, pg. 5229-5234 (2009)). However, synthetic block copolymer polypeptides having sequence similarity and/or amino acid composition similarity to the repeat domains of native silk proteins can be used to manufacture on commercial scales consistent silk-like fibers that recapitulate the properties of corresponding natural silk fibers.

In some embodiments, a list of putative silk sequences can be compiled by searching GenBank for relevant terms, e.g. "spidroin" "fibroin" "MaSp", and those sequences can be pooled with additional sequences obtained through independent sequencing efforts. Sequences are then translated into amino acids, filtered for duplicate entries, and manually split into domains (NTD, REP, CTD). In some embodiments, candidate amino acid sequences are reverse translated into a DNA sequence optimized for expression in *Pichia (Komagataella) pastoris*. The DNA sequences are each cloned into an expression vector and transformed into *Pichia (Komagataella) pastoris*. In some embodiments, various silk domains demonstrating successful expression and secretion are subsequently assembled in combinatorial fashion to build silk molecules capable of fiber formation.

Silk polypeptides are characteristically composed of a repeat domain (REP) flanked by non-repetitive regions (e.g., C-terminal and N-terminal domains). In an embodiment, both the C-terminal and N-terminal domains are between 75-350 amino acids in length. The repeat domain exhibits a hierarchical architecture, as depicted in FIG. 1. The repeat domain comprises a series of blocks (also called repeat units). The blocks are repeated, sometimes perfectly and sometimes imperfectly (making up a quasi-repeat domain), throughout the silk repeat domain. The length and composition of blocks varies among different silk types and across different species. Table 1 lists examples of block sequences from selected species and silk types, with further examples presented in Rising, A. et al., Spider silk proteins: recent advances in recombinant production, structure-function relationships and biomedical applications, *Cell Mol. Life Sci.*, 68:2, pg 169-184 (2011); and Gatesy, J. et al., Extreme diversity, conservation, and convergence of spider silk fibroin sequences, *Science,* 291:5513, pg. 2603-2605 (2001). In some cases, blocks may be arranged in a regular pattern, forming larger macro-repeats that appear multiple times (usually 2-8) in the repeat domain of the silk sequence. Repeated blocks inside a repeat domain or macro-repeat, and repeated macro-repeats within the repeat domain, may be separated by spacing elements. In some embodiments, block sequences comprise a glycine rich region followed by a polyA region. In some embodiments, short (~1-10) amino acid motifs appear multiple times inside of blocks. A subset of commonly observed motifs is depicted in FIG. 1. For the purpose of this invention, blocks from different natural silk polypeptides can be selected without reference to circular permutation (i.e., identified blocks that are otherwise similar between silk polypeptides may not align due to circular permutation). Thus, for example, a "block" of SGAGG (SEQ ID NO: 2804) is, for the purposes of the present invention, the same as GSGAG (SEQ ID NO: 2805) and the same as GGSGA (SEQ ID NO: 2806); they are all just circular permutations of each other. The particular permutation selected for a given silk sequence can be dictated by convenience (usually starting with a G) more than anything else. Silk sequences obtained from the NCBI database can be partitioned into blocks and non-repetitive regions.

TABLE 1

Samples of Block Sequences

| Species | Silk Type | Representative Block Amino Acid Sequence |
|---|---|---|
| *Aliatypus gulosus* | Fibroin 1 | GAASSSSTIITTKSASASAAADASAAATASAASRSSAN AAASAFAQSFSSILLESGYFCSIFGSSISSSYAAAIASAA SRAAAESNGYTTHAYACAKAVASAVERVTSGADAY AYAQAISDALSHALLYTGRLNTANANSLASAFAYAF ANAAAQASASSASAGAASASGAASASGAGSAS (SEQ ID NO: 2807) |
| *Plectreurys tristis* | Fibroin 1 | GAGAGAGAGAGAGAGAGSGASTSVSTSSSSGSGAGA GAGSGAGSGAGAGSGAGAGAGGAGAGFGSGLGL GYGVGLSSAQAQAQAQAAAQAQAQAQAQAYAAAQ AQAQAQAQAQAAAAAAAAAAA (SEQ ID NO: 2808) |
| *Plectreurys tristis* | Fibroin 4 | GAAQKQPSGESSVATASAAATSVTSGGAPVGKPGVP APIFYPQGPLQQGPAPGPSNVQPGTSQQGPIGGVGGS NAFSSSFASALSLNRGFTEVISSASATAVASAFQKGLA PYGTAFALSAASAAADAYNSIGSGANAFAYAQAFAR VLYPLVQQYGLSSSAKASAFASAIASSFSSGTSGQGPS IGQQQPPVTISAASASAGASAAAVGGGQVGQGPYGG QQQSTAASASAAAATATS (SEQ ID NO: 2809) |

TABLE 1-continued

Samples of Block Sequences

| Species | Silk Type | Representative Block Amino Acid Sequence |
|---|---|---|
| Araneus gemmoides | TuSp | GNVGYQLGLKVANSLGLGNAQALASSLSQAVSAVG VGASSNAYANAVSNAVGQVLAGQGILNAANAGSLA SSFASALSSSAASVASQSASQSQAASQSQAAASAFRQ AASQSASQSDSRAGSQSSTKTTSTSTSGSQADSRSASS SASQSASAFAQQSSASLSSSSSFSSAFSSATSISAV (SEQ ID NO: 2810) |
| Argiope aurantia | TuSp | GSLASSFASALSASAASVASSAAAQAASQSQAAASAF SRAASQSASQSAARSGAQSISTTTTTSTAGSQAASQSA SSAASQSASSFARASSASLAASSSFSSAFSSANSLSAL GNVGYQLGFNVANNLGIGNAAGLGNALSQAVSSVG VGASSSTYANAVSNAVGQFLAGQGILNAANA (SEQ ID NO: 2811) |
| Deinopis spinosa | TuSp | GASASAYASAISNAVGPYLYGLGLFNQANAASFASSF ASAVSSAVASASASAASSAYAQSAAAQAQAASSAFS QAAAQSAAAASAGASAGASAGAGAVAGAGAVA GAGAVAGASAAAASQAAASSSASAVASAFAQSASY ALASSSAFANAFASATSAGYLGSLAYQLGLTTAYNL GLSNAQAFASTLSQAVTGVGL (SEQ ID NO: 2812) |
| Nephila clavipes | TuSp | GATAASYGNALSTAAAQFFATAGLLNAGNASALASS FARAFSASAESQSFAQSQAFQQASAFQQAASRSASQS AAEAGSTSSSTTTTTSAARSQAASQSASSSYSSAFAQA ASSSLATSSALSRAFSSVSSASAASSLAYSIGLSAARSL GIADAAGLAGVLARAAGALGQ (SEQ ID NO: 2813) |
| Argiope trifasciata | Flag | GGAPGGGPGGAGPGGAGFGPGGGAGFGPGGGAGFG PGGAAGGPGGPGGPGGPGGAGGYGPGGAGGYGPGG VGPGGAGGYGPGGAGGYGPGGSGPGGAGPGGAGGE GPVTVDVDVTVGPEGVGGGPGGAGPGGAGFGPGGG AGFGPGGAPGAPGGPGGPGGPGGPGGPGGVGPGGA GGYGPGGAGGVGPAGTGGFGPGGAGGFGPGGAGGF GPGGAGGFGPAGAGGYGPGGVGPGGAGGFGPGGVG PGGSGPGGAGGEGPVTVDVDVSV (SEQ ID NO: 2814) |
| Nephila clavipes | Flag | GVSYGPGGAGGPYGPGGPYGPGGEGPGGAGGPYGP GGVGPGGSGPGGYGPGGAGPGGYGPGGSGPGGYGP GGSGPGGYGPGGSGPGGYGPGGSGPGGYGPGGYGP GGSGPGGSGPGGSGPGGYGPGGTGPGGSGPGGYGPG GSGPGGSGPGGYGPGGSGPGGFGPGGSGPGGYGPGG SGPGGAGPGGVGPGGFGPGGAGPGGAAPGGAGPGG AGPGGAGPGGAGPGGAGPGGAGGAGGAGGS GGAGGSGGTTIIEDLDITIDGADGPITISEELPISGAGGS GPGGAGPGGVGPGGSGPGGVGPGGSGPGGVGPGGS GPGGVGPGGAGGPYGPGGSGPGGAGGAGGPGGAYG PGGSYGPGGSGPGGAGGPYGPGGEGPGGAGGPYGP GGAGGPYGPGGAGGPYGPGGEGGPYGP (SEQ ID NO: 2815) |
| Latrodectus hesperus | AcSp | GINVDSDIGSVTSLILSGSTLQMTIPAGGDDLSGGYPG GFPAGAQPSGGAPVDFGGPSAGGDVAAKLARSLAST LASSGVFRAAFNSRVSTPVAVQLTDALVQKIASNLGL DYATASKLRKASQAVSKVRMGSDTNAYALAISSALA EVLSSSGKVADANINQIAPQLASGIVLGVSTTAPQFGV DLSSINVNLDISNVARNMQASIQGGPAPITAEGPDFGA GYPGGAPTDLSGLDMGAPSDGSRGGDATAKLLQAL VPALLKSDVFRAIYKRGTRKQVVQYVTNSALQQAAS SLGLDASTISQLQTKATQALSSVSADSDSTAYAKAFG LAIAQVLGTSGQVNDANVNQIGAKLATGILRGSSAV APRLGIDLS (SEQ ID NO: 2816) |
| Argiope trifasciata | AcSp | GAGYTGPSGPSTGPSGYPGPLGGGAPFGQSGFGGSAG PQGGFGATGGASAGLISRVANALANTSTLRTVLRTG VSQQIASSVVQRAAQSLASTLGVDGNNLARFAVQAV SRLPAGSDTSAYAQAFSSALFNAGVLNASNIDTLGSR VLSALLNGVSSAAQGLGINVDSGSVQSDISSSSSFLST SSSSASYSQASASSTS (SEQ ID NO: 2817) |
| Uloborus diversus | AcSp | GASAADIATAIAASVATSLQSNGVLTASNVSQLSNQL ASYVSSGLSSTASSLGIQLGASLGAGFGASAGLSASTD ISSSVEATSASTLSSSASSTSVVSSINAQLVPALAQTAV LNAAFSNINTQNAIRIAELLTQQVGRQYGLSGSDVAT ASSQIRSALYSVQQGSASSAYVSAIVGPLITALSSRGV VNASNSSQIASSLATAILQFTANVAPQFGISIPTSAVQS |

TABLE 1-continued

Samples of Block Sequences

| Species | Silk Type | Representative Block Amino Acid Sequence |
|---|---|---|
| | | DLSTISQSLTAISSQTSSSVDSSTSAFGGISGPSGPSYG PQPSGPTFGPGPSLSGLTGFTATFASSFKSTLASSTQFQ LIAQSNLDVQTRSSLISKVLINALSSLGISASVASSIAAS SSQSLLSVSA (SEQ ID NO: 2818) |
| Euprosthenops australis | MaSp1 | GGQGGQGQGRYGQGAGSSAAAAAAAAAAAAAA (SEQ ID NO: 2819) |
| Tetragnatha kauaiensis | MaSp1 | GGLGGGQGAGQGGQQGAGQGGYGSGLGGAGQGAS AAAAAAAA (SEQ ID NO: 2820) |
| Argiope aurantia | MaSp2 | GGYGPGAGQQGPGSQGPGSGGQQGPGGLGPYGPSA AAAAAAA (SEQ ID NO: 2821) |
| Deinopis spinosa | MaSp2 | GPGGYGGPGQQGPGQGQYGPGTGQQGQGPSGQQGP AGAAAAAAAA (SEQ ID NO: 2822) |
| Nephila clavata | MaSp2 | GPGGYGLGQQGPGQQGPGQQGPAGYGPSGLSGPGG AAAAAAA (SEQ ID NO: 2823) |

Figure 2:
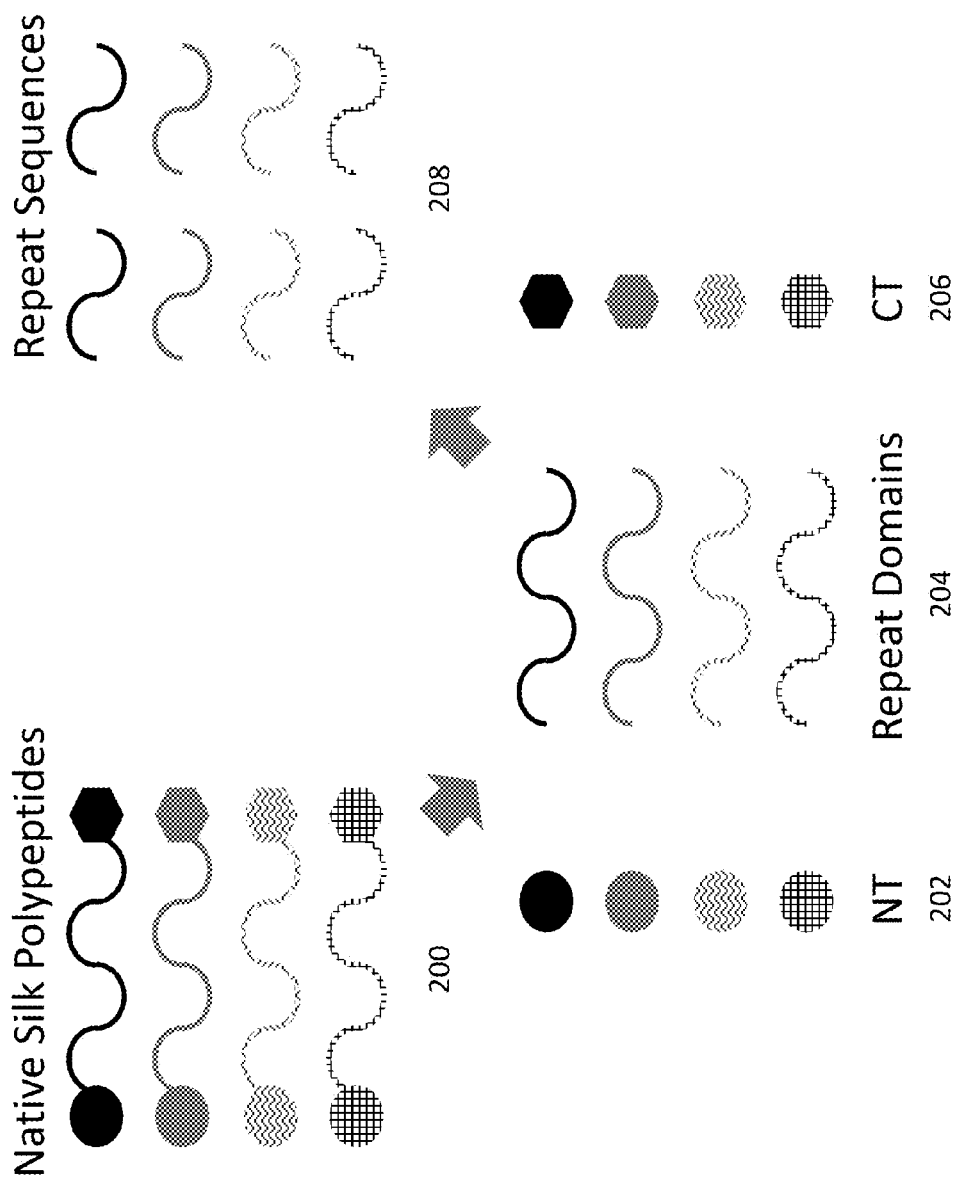
FIG. 2 shows a screening process for silk polypeptide domains and their DNA encoding according to some embodiments of the invention.
Figure 3:
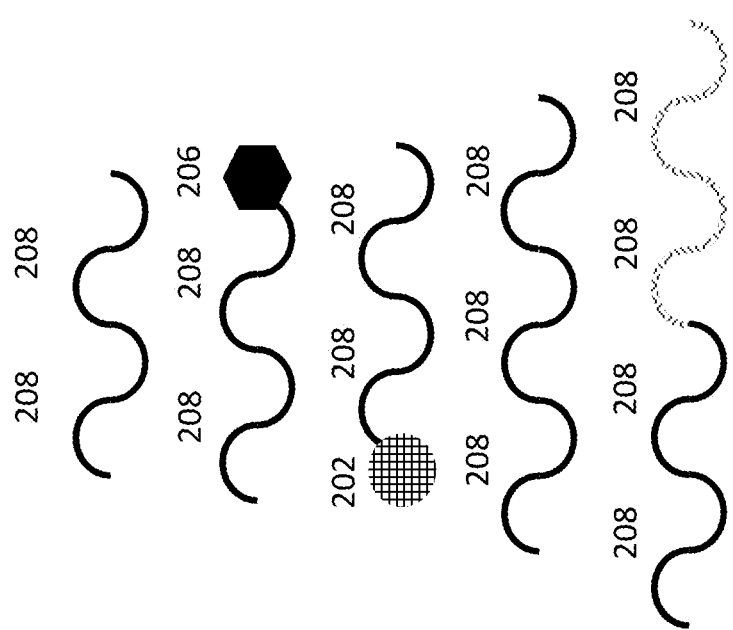
FIG. 3 shows how silk repeat sequences and terminal domains that pass preliminary screening are assembled to create functional block copolymers that can be purified and made into fibers, according to an embodiment of the invention.

The construction of fiber-forming block copolymer polypeptides from the blocks and/or macro-repeat domains, according to certain embodiments of the invention, is shown in FIGS. 2 and 3. FIG. 2 illustrates the division of silk sequences into distinct domains. Natural silk sequences 200 obtained from a protein database such as GenBank or through de novo sequencing are broken up by domain (N-terminal domain 202, repeat domain 204, and C-terminal domain 206). The N-terminal domain 202 and C-terminal domain 206 sequences selected for the purpose of synthesis and assembly into fibers include natural amino acid sequence information and other modifications described herein. The repeat domain 204 is decomposed into repeat sequences 208 containing representative blocks, usually 1-8 depending upon the type of silk, that capture critical amino acid information while reducing the size of the DNA encoding the amino acids into a readily synthesizable fragment. FIG. 3 illustrates how select NT 202, CT 206, and repeat sequences 208 can be assembled to create block copolymer polypeptides that can be purified and made into fibers that recapitulate the functional properties of silk, according to an embodiment of the invention. Individual NT, CT, and repeat sequences that have been verified to express and secrete are assembled into functional block copolymer polypeptides. In some embodiments, a properly formed block copolymer polypeptide comprises at least one repeat domain comprising at least 1 repeat sequence 208, and is optionally flanked by an N-terminal domain 202 and/or a C-terminal domain 206.

In some embodiments, a repeat domain comprises at least one repeat sequence. In some embodiments, the repeat sequence, N-terminal domain sequence, and/or C-terminal domain sequence is selected from SEQ ID NOs: 932-1398. In some embodiments, the repeat sequence is 150-300 amino acid residues. In some embodiments, the repeat sequence comprises a plurality of blocks. In some embodiments, the repeat sequence comprises a plurality of macro-repeats. In some embodiments, a block or a macro-repeat is split across multiple repeat sequences.

In some embodiments, the repeat sequence starts with a Glycine, and cannot end with phenylalanine (F), tyrosine (Y), tryptophan (W), cysteine (C), histidine (H), asparagine (N), methionine (M), or aspartic acid (D) to satisfy DNA assembly requirements. In some embodiments, some of the repeat sequences can be altered as compared to native sequences. In some embodiments, the repeat sequences can be altered such as by addition of a serine to the C terminus of the polypeptide (to avoid terminating in F, Y, W, C, H, N, M, or D). In some embodiments, the repeat sequence can be modified by filling in an incomplete block with homologous sequence from another block. In some embodiments, the repeat sequence can be modified by rearranging the order of blocks or macrorepeats.

In some embodiments, non-repetitive N- and C-terminal domains can be selected for synthesis (See SEQ ID NOs: 1-145). In some embodiments, N-terminal domains can be by removal of the leading signal sequence, e.g., as identified by SignalP (Peterson, T. N., et. Al., SignalP 4.0: discriminating signal peptides from transmembrane regions, *Nat. Methods*, 8:10, pg. 785-786 (2011).

In some embodiments, the N-terminal domain, repeat sequence, or C-terminal domain sequences can be derived from *Agelenopsis aperta, Aliatypus gulosus, Aphonopelma seemanni, Aptostichus* sp. AS217, *Aptostichus* sp. AS220, *Araneus diadematus, Araneus gemmoides, Araneus ventricosus, Argiope amoena, Argiope argentata, Argiope bruennichi, Argiope trifasciata, Atypoides riversi, Avicularia juruensis, Bothriocyrtum californicum, Deinopis Spinosa, Diguetia canities, Dolomedes tenebrosus, Euagrus chisoseus, Euprosthenops australis, Gasteracantha mammosa, Hypochilus thorelli, Kukulcania hibernalis, Latrodectus hesperus, Megahexura fulva, Metepeira grandiosa, Nephila antipodiana, Nephila clavata, Nephila clavipes, Nephila madagascariensis, Nephila pilipes, Nephilengys cruentata, Parawixia bistriata, Peucetia viridans, Plectreurys tristis, Poecilotheria regalis, Tetragnatha kauaiensis,* or *Uloborus diversus*.

In some embodiments, the silk polypeptide nucleotide coding sequence can be operatively linked to an alpha mating factor nucleotide coding sequence. In some embodiments, the silk polypeptide nucleotide coding sequence can be operatively linked to another endogenous or heterologous secretion signal coding sequence. In some embodiments, the silk polypeptide nucleotide coding sequence can be operatively linked to a 3× FLAG nucleotide coding sequence. In some embodiments, the silk polypeptide nucleotide coding sequence is operatively linked to other affinity tags such as 6-8 His residues (SEQ ID NO: 2824).

Expression Vectors

The expression vectors of the present invention can be produced following the teachings of the present specification in view of techniques known in the art. Sequences, for example vector sequences or sequences encoding transgenes, can be commercially obtained from companies such as Integrated DNA Technologies, Coralville, Iowa or DNA 2.0, Menlo Park, Calif. Exemplified herein are expression vectors that direct high-level expression of the chimeric silk polypeptides.

Another standard source for the polynucleotides used in the invention is polynucleotides isolated from an organism (e.g., bacteria), a cell, or selected tissue. Nucleic acids from the selected source can be isolated by standard procedures, which typically include successive phenol and phenol/chloroform extractions followed by ethanol precipitation. After precipitation, the polynucleotides can be treated with a restriction endonuclease which cleaves the nucleic acid molecules into fragments. Fragments of the selected size can be separated by a number of techniques, including agarose or polyacrylamide gel electrophoresis or pulse field gel electrophoresis (Care et al. (1984) Nuc. Acid Res. 12:5647-5664; Chu et al. (1986) Science 234:1582; Smith et al. (1987) Methods in Enzymology 151:461), to provide an appropriate size starting material for cloning.

Another method of obtaining the nucleotide components of the expression vectors or constructs is PCR. General procedures for PCR are taught in MacPherson et al., PCR: A PRACTICAL APPROACH, (IRL Press at Oxford University Press, (1991)). PCR conditions for each application reaction may be empirically determined. A number of parameters influence the success of a reaction. Among these parameters are annealing temperature and time, extension time, Mg2+ and ATP concentration, pH, and the relative concentration of primers, templates and deoxyribonucleotides. Exemplary primers are described below in the Examples. After amplification, the resulting fragments can be detected by agarose gel electrophoresis followed by visualization with ethidium bromide staining and ultraviolet illumination.

Another method for obtaining polynucleotides is by enzymatic digestion. For example, nucleotide sequences can be generated by digestion of appropriate vectors with suitable recognition restriction enzymes. Restriction cleaved fragments may be blunt ended by treating with the large fragment of E. coli DNA polymerase I (Klenow) in the presence of the four deoxynucleotide triphosphates (dNTPs) using standard techniques.

Polynucleotides are inserted into suitable backbones, for example, plasmids, using methods well known in the art. For example, insert and vector DNA can be contacted, under suitable conditions, with a restriction enzyme to create complementary or blunt ends on each molecule that can pair with each other and be joined with a ligase. Alternatively, synthetic nucleic acid linkers can be ligated to the termini of a polynucleotide. These synthetic linkers can contain nucleic acid sequences that correspond to a particular restriction site in the vector DNA. Other means are known and available in the art. A variety of sources can be used for the component polynucleotides.

In some embodiments, expression vectors containing an R, N, or C sequence are transformed into a host organism for expression and secretion. In some embodiments, the expression vectors comprise a secretion signal. In some embodiments, the expression vector comprises a terminator signal. In some embodiments, the expression vector is designed to integrate into a host cell genome and comprises: regions of homology to the target genome, a promoter, a secretion signal, a tag (e.g., a Flag tag), a termination/polyA signal, a selectable marker for Pichia, a selectable marker for E. coli, an origin of replication for E. coli, and restriction sites to release fragments of interest.

Host Cell Transformants

In some embodiments of the present invention, host cells transformed with the nucleic acid molecules or vectors of the present invention, and descendants thereof, are provided. In some embodiments of the present invention, these cells carry the nucleic acid sequences of the present invention on vectors, which may but need not be freely replicating vectors. In other embodiments of the present invention, the nucleic acids have been integrated into the genome of the host cells.

In some embodiments, microorganisms or host cells that enable the large-scale production of block copolymer polypeptides of the invention include a combination of: 1) the ability to produce large (>75 kDa) polypeptides, 2) the ability to secrete polypeptides outside of the cell and circumvent costly downstream intracellular purification, 3) resistance to contaminants (such as viruses and bacterial contaminations) at large-scale, and 4) the existing know-how for growing and processing the organism is large-scale (1-2000 m$^3$) bioreactors.

A variety of host organisms can be engineered/transformed to comprise a block copolymer polypeptide expression system. Preferred organisms for expression of a recombinant silk polypeptide include yeast, fungi, and gram-positive bacteria. In certain embodiments, the host organism is Arxula adeninivorans, Aspergillus aculeatus, Aspergillus awamori, Aspergillus ficuum, Aspergillus fumigatus, Aspergillus japonicus, Aspergillus nidulans, Aspergillus niger, Aspergillus oryzae, Aspergillus sojae, Aspergillus tubigensis, Bacillus alkalophilus, Bacillus amyloliquefaciens, Bacillus anthracia, Bacillus brevis, Bacillus circulans, Bacillus coagulans, Bacillus lautus, Bacillus lentus, Bacillus licheniformis, Bacillus methanolicus, Bacillus stearothermophilus, Bacillus subtilis, Bacillus thuringiensis, Candida boidinii, Chrysosporium lucknowense, Fusarium graminearum, Fusarium venenatum, Kluyveromyces lactis, Kluyveromyces marxianus, Myceliopthora thermophila, Neurospora crassa, Ogataea polymorpha, Penicillium camemberti, Penicillium canescens, Penicillium chrysogenum, Penicillium emersonii, Penicillium funiculosum, Penicillium griseoroseum, Penicillium purpurogenum, Penicillium roqueforti, Phanerochaete chrysosporium, Pichia angusta, Pichia methanolica, Pichia (Komagataella) pastoris, Pichia polymorpha, Pichia stipitis, Rhizomucor miehei, Rhizomucor pusillus, Rhizopus arrhizus, Streptomyces lividans, Saccharomyces cerevisiae, Schwanniomyces occidentalis, Trichoderma harzianum, Trichoderma reesei, or Yarrowia lipolytica.

In preferred aspects, the methods provide culturing host cells for direct product secretion for easy recovery without the need to extract biomass. In some embodiments, the block copolymer polypeptides are secreted directly into the medium for collection and processing.

Polypeptide Purification

The recombinant block copolymer polypeptides based on spider silk sequences produced by gene expression in a recombinant prokaryotic or eukaryotic system can be purified according to methods known in the art. In a preferred embodiment, a commercially available expression/secretion system can be used, whereby the recombinant polypeptide is expressed and thereafter secreted from the host cell, to be easily purified from the surrounding medium. If expression/secretion vectors are not used, an alternative approach involves purifying the recombinant block copolymer polypeptide from cell lysates (remains of cells following disruption of cellular integrity) derived from prokaryotic or eukaryotic cells in which a polypeptide was expressed. Methods for generation of such cell lysates are known to those of skill in the art. In some embodiments, recombinant block copolymer polypeptides are isolated from cell culture supernatant.

Recombinant block copolymer polypeptide may be purified by affinity separation, such as by immunological interaction with antibodies that bind specifically to the recombinant polypeptide or nickel columns for isolation of recombinant polypeptides tagged with 6-8 histidine residues at their N-terminus or C-terminus Alternative tags may comprise the FLAG epitope or the hemagglutinin epitope. Such methods are commonly used by skilled practitioners.

Additionally, the method of the present invention may preferably include a purification method, comprising exposing the cell culture supernatant containing expressed block copolymer polypeptides to ammonium sulphate of 5-60% saturation, preferably 10-40% saturation.

Spinning to Generate Fibers

In some embodiments, a solution of block copolymer polypeptide of the present invention is spun into fibers using elements of processes known in the art. These processes include, for example, wet spinning, dry-jet wet spinning, and dry spinning. In preferred wetspinning embodiments, the filament is extruded through an orifice into a liquid coagulation bath. In one embodiment, the filament can be extruded through an air gap prior to contacting the coagulation bath. In a dry-jet wet spinning process, the spinning solution is attenuated and stretched in an inert, non-coagulating fluid, e.g., air, before entering the coagulating bath. Suitable coagulating fluids are the same as those used in a wetspinning process.

Preferred coagulation baths for wet spinning are maintained at temperatures of 0-90° C., more preferably 20-60° C., and are preferably about 60%, 70%, 80%, 90%, or even 100% alcohol, preferably isopropanol, ethanol, or methanol. In a preferred embodiment, the coagulation bath is 85:15% by volume methanol:water. In alternate embodiments, coagulation baths comprise ammonium sulfate, sodium chloride, sodium sulfate, or other protein precipitating salts at temperature between 20-60° C. Certain coagulant baths can be preferred depending upon the composition of the dope solution and the desired fiber properties. For example, salt based coagulant baths are preferred for an aqueous dope solution. For example, methanol is preferred to produce a circular cross section fiber. Residence times in coagulation baths can range from nearly instantaneous to several hours, with preferred residence times lasting under one minute, and more preferred residence times lasting about 20 to 30 seconds. Residence times can depend on the geometry of the extruded fiber or filament. In certain embodiments, the extruded filament or fiber is passed through more than one coagulation bath of different or same composition. Optionally, the filament or fiber is also passed through one or more rinse baths to remove residual solvent and/or coagulant. Rinse baths of decreasing salt or alcohol concentration up to, preferably, an ultimate water bath, preferably follow salt or alcohol baths.

Following extrusion, the filament or fiber can be drawn. Drawing can improve the consistency, axial orientation and toughness of the filament. Drawing can be enhanced by the composition of a coagulation bath. Drawing may also be performed in a drawing bath containing a plasticizer such as water, glycerol or a salt solution. Drawing can also be performed in a drawing bath containing a crosslinker such as gluteraldehyde or formaldehyde. Drawing can be performed at temperature from 25-100° C. to alter fiber properties, preferably at 60° C. As is common in a continuous process, drawing can be performed simultaneously during the coagulation, wash, plasticizing, and/or crosslinking procedures described previously. Drawing rates depend on the filament being processed. In one embodiment, the drawing rate is preferably about 5x the rate of reeling from the coagulation bath.

In certain embodiments of the invention, the filament is wound onto a spool after extrusion or after drawing. Winding rates are generally 1 to 500 m/min, preferably 10 to 50 m/min.

In other embodiments, to enhance the ease with which the fiber is processed, the filament can be coated with lubricants or finishes prior to winding. Suitable lubricants or finishes can be polymers or wax finishes including but not limited to mineral oil, fatty acids, isobutyl-stearate, tallow fatty acid 2-ethylhexyl ester, polyol carboxylic acid ester, coconut oil fatty acid ester of glycerol, alkoxylated glycerol, a silicone, dimethyl polysiloxane, a polyalkylene glycol, polyethylene oxide, and a propylene oxide copolymer.

The spun fibers produced by the methods of the present invention can possess a diverse range of physical properties and characteristics, dependent upon the initial properties of the source materials, i.e., the dope solution, and the coordination and selection of variable aspects of the present method practiced to achieve a desired final product, whether that product be a soft, sticky, pliable matrix conducive to cellular growth in a medical application or a load-bearing, resilient fiber, such as fishing line or cable. The tensile strength of filaments spun by the methods of the present invention generally range from 0.2 g/denier (or g/(g/9000 m)) to 3 g/denier, with filaments intended for load-bearing uses preferably demonstrating a tensile strength of at least 2 g/denier. In an embodiment, the fibers have a fineness between 0.2-0.6 denier. Such properties as elasticity and elongation at break vary dependent upon the intended use of the spun fiber, but elasticity is preferably 5% or more, and elasticity for uses in which elasticity is a critical dimension, e.g., for products capable of being "tied," such as with sutures or laces, is preferably 10% or more. Water retention of spun fibers preferably is close to that of natural silk fibers, i.e., 10%. The diameter of spun fibers can span a broad range, dependent on the application; preferred fiber diameters range from 5, 10, 20, 30, 40, 50, 60 microns, but substantially thicker fibers may be produced, particularly for industrial applications (e.g., cable). The cross-sectional characteristics of spun fibers can vary; e.g., preferable spun fibers include circular cross-sections, elliptical, starburst cross-sections, and spun fibers featuring distinct core/sheath sections, as well as hollow fibers.

Example 1

Obtaining Silk Sequences

Silk sequences and partial sequences were obtained by searching NCBI's nucleotide database using the following terms to identify spider silks: MaSp, TuSp, CySp, MiSp, AcSp, Flag, major ampullate, minor ampullate, flagelliform, aciniform, tubuliform, cylindriform, spidroin, and spider fibroin. The resulting nucleotide sequences were translated into amino acid sequences, then curated to remove repeated sequences. Sequences that were less than 200-500 amino acids long, depending on the type of silk, were removed. Silk sequences from the above search were partitioned into blocks (e.g., repetitive sequences) and non-repetitive regions.

Repetitive polypeptide sequences (repeat (R) sequences) were selected from each silk sequence, and are listed as SEQ ID NOs: 1077-1393. Some of the R sequences have been altered, e.g., by addition of a serine to the C terminus to avoid terminating the sequence with an F, Y, W, C, H, N, M, or D amino acid. This allows for incorporation into the vector system described below. We also altered incomplete blocks by incorporation of segments from a homologous sequence from another block. For some sequences of SEQ ID NOs: 1077-1393, the order of blocks or macro-repeats has been altered from the sequence found in the NCBI database, and make up quasi-repeat domains Non-repetitive N terminal domain sequences (N sequences) and C terminal domain sequences (C sequences) were also selected from each silk sequence (SEQ ID NOs: 932-1076). The N terminal domain sequences were altered by removal of the leading signal sequence and, if not already present, addition of an N-terminal glycine residue.

A number of embodiments of the invention have been described. Nevertheless, it will be understood that various modifications may be made without departing from the spirit and scope of the invention.

Example 2

Reverse Translation of Silk Polypeptide Sequences to Nucleotide Sequences

R, N, and C amino acid sequences described in Example 1 were reverse translated to nucleotide sequences. To perform reverse translation, 10,000 candidate sequences were generated by using the *Pichia* (*Komagataella*) *pastoris* codon usage to bias random selection of a codon encoding the desired amino acid at each position. Select restriction sites (BsaI, BbsI, BtgZI, AscI, SbfI) were then removed from each sequence; if a site could not be removed, the sequence was discarded. Then, the entropy, longest repeated subsequence, and number of repeated 15-mers were each determined for each sequence.

To choose the optimal sequence to use for synthesis out of each set of 10,000, the following criteria were sequentially applied: keep the sequences with the lowest 25% of longest repeated subsequence, keep the sequences with the highest 10% of sequence entropy, and use the sequence with the lowest number of repeated 15-mers.

Example 3

Screening of Silk Polypeptides from Selected N, C, or R Sequences

The nucleotide sequences from Examples 1 and 2 were flanked with the following sequences during synthesis to enable cloning:

5'-GAAGACTTAGCA-SILK-GGTACGTCTTC-3' (SEQ ID NOS 2825 and 2826) where "SILK" is a polynucleotide sequence selected according to the teachings of Example 2.

Resulting DNA was digested with BbsI and ligated into either Expression Vector RM618 (SEQ ID NO:1399) or Expression Vector RM652 (SEQ ID NO:1400) which had been digested with BtgZI and treated with Calf Intestinal Alkaline Phosphatase. Ligated material was transformed into *E. coli* for clonal isolation and DNA amplification using standard methods. *Pichia* (*Komagataella*) *pastoris*

Expression vectors containing an R, N, or C sequence were transformed into *Pichia* (*Komagataella*) *pastoris* (strain RMs71, which is strain GS115 (NRRL Y15851) with the mutation in the HIS4 gene restored to wild-type via transformation with a fragment of the wild-type genome (NRRLY 11430) and selection on defined medium agar plates lacking histidine) using the PEG method (Cregg, J. M., DNA-mediated transformation, *Methods Mol. Biol.*, 389, pg. 27-42 (2007).). The expression vector consisted of a targeting region (HIS4), a dominant resistance marker (nat-conferring resistance to nourseothricin), a promoter (pGAP), a secretion signal (alpha mating factor leader and pro sequence), and a terminator (pAOX1 pA signal).

Transformants were plated on YPD agar plates containing 25 µg/ml nourseothricin and incubated for 48 hours at 30° C. Two clones from each transformation were inoculated into 400 µl of YPD in a 96-well square-well block, and incubated for 48 hours at 30° C. with agitation at 1000 rpm. Cells were pelleted via centrifugation, and the supernatant was recovered for analysis of silk polypeptide content via western blot. The resulting data demonstrates a variety of expression and secretion phenotypes, ranging from undetectable polypeptide levels in the supernatant to strong signal on the western blot indicative of relatively high titre.

Figure 4:
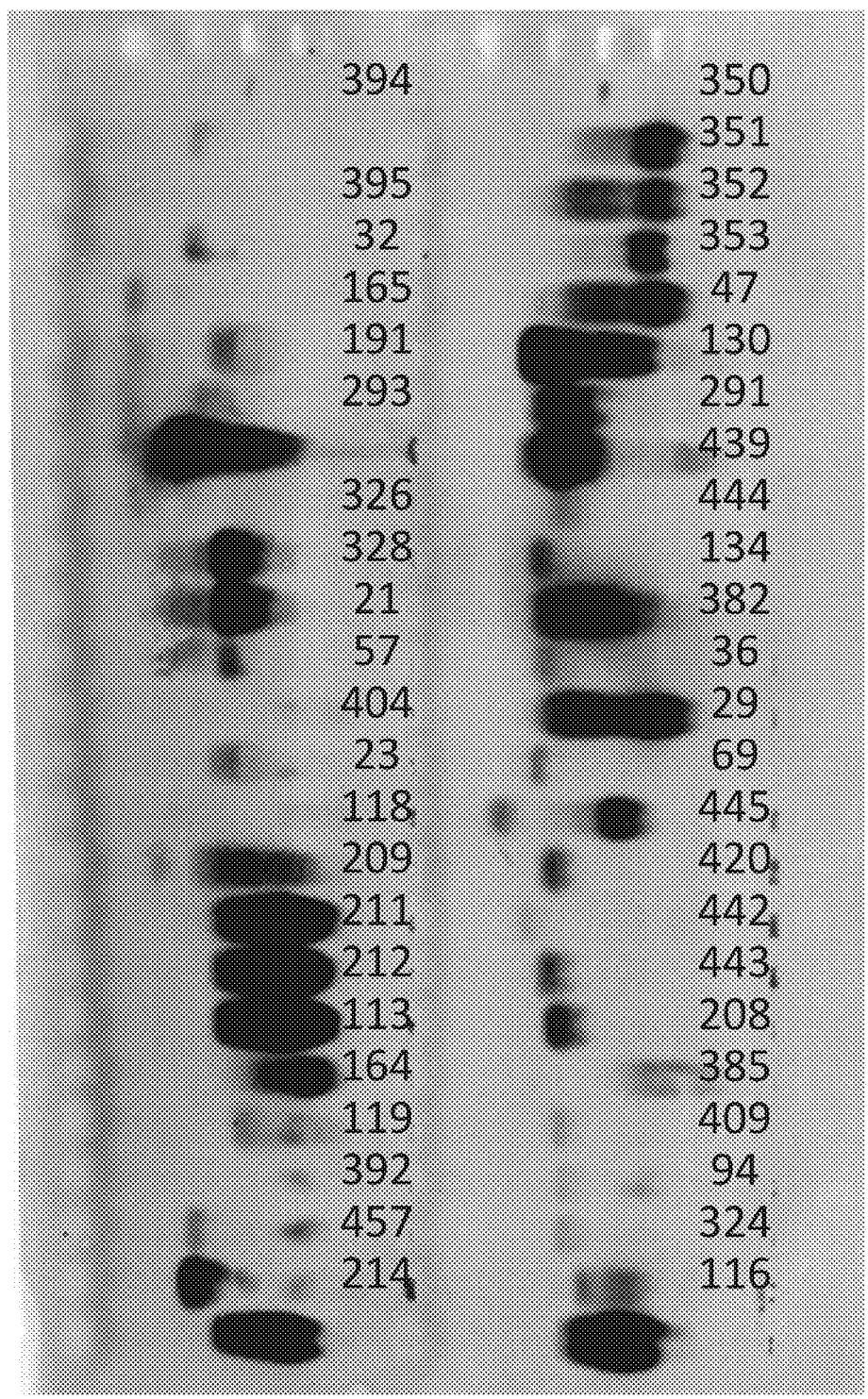
FIG. 4 shows a representative western blot of expressed silk repeat sequences and terminal domain sequences.
Figure 5:
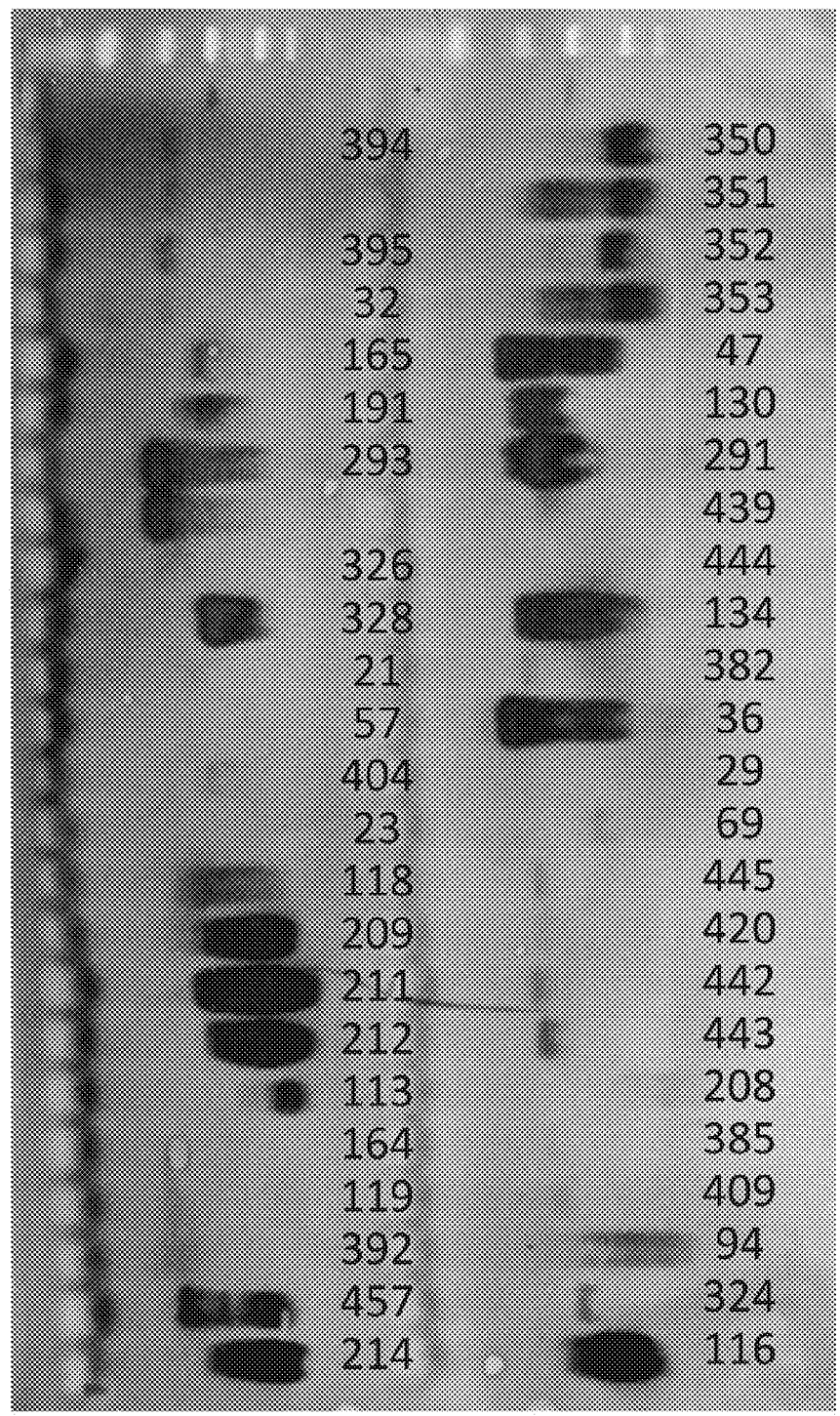
FIG. 5 shows a representative western blot of expressed silk repeat sequences and terminal domain sequences.

Successful polypeptide expression and secretion was judged by western blot. Each western lane was scored as 1: No band 2: Moderate band or 3: Intense band. The higher of the two scores for each clone was recorded. Representative western blots with construct numbers labeled are shown in FIG. 4 and FIG. 5, with additional western blots with representative clones shown in FIG. 14. A complete listing of all R, N, and C sequences tested along with western blot results is shown in Table 2. Silk polypeptides from numerous species expressed successfully, encompassing every category of gland and all domain types.

TABLE 2

Silk polypeptide sequences

| Construct # | Species | N/C/R sequence | Nucleotide SEQ ID NO | Nucleotide with flanking sequences SEQ ID NO: | Amino acid SEQ ID NO: | Western Results (1 = no band 2 = weak band 3 = strong band) |
| --- | --- | --- | --- | --- | --- | --- |
| 1 | *Aliatypus gulosus* | C | 1 | 468 | 932 | no data |
| 2 | *Aptostichus* sp. AS217 | C | 2 | 469 | 933 | 3 |
| 3 | *Aptostichus* sp. AS220 | C | 3 | 470 | 934 | 3 |
| 4 | *Araneus diadematus* | C | 4 | 471 | 935 | 3 |
| 5 | *Araneus diadematus* | C | 5 | 472 | 936 | no data |
| 6 | *Araneus diadematus* | C | 6 | 473 | 937 | no data |
| 7 | *Araneus diadematus* | C | 7 | 474 | 938 | 3 |
| 8 | *Atypoides riversi* | C | 8 | 475 | 939 | 2 |

TABLE 2-continued

Silk polypeptide sequences

| Construct # | Species | N/C/R sequence | Nucleotide SEQ ID NO | Nucleotide with flanking sequences SEQ ID NO: | Amino acid SEQ ID NO: | Western Results (1 = no band 2 = weak band 3 = strong band) |
|---|---|---|---|---|---|---|
| 9 | Bothriocyrtum californicum | C | 9 | 476 | 940 | 2 |
| 10 | Bothriocyrtum californicum | C | 10 | 477 | 941 | 3 |
| 11 | Bothriocyrtum californicum | C | 11 | 478 | 942 | 2 |
| 12 | Deinopis Spinosa | C | 12 | 479 | 943 | 3 |
| 13 | Deinopis Spinosa | C | 13 | 480 | 944 | 3 |
| 14 | Deinopis Spinosa | C | 14 | 481 | 945 | 2 |
| 15 | Dolomedes tenebrosus | C | 15 | 482 | 946 | 2 |
| 16 | Euagrus chisoseus | C | 16 | 483 | 947 | 3 |
| 17 | Plectreurys tristis | C | 17 | 484 | 948 | 3 |
| 18 | Plectreurys tristis | C | 18 | 485 | 949 | 2 |
| 19 | Plectreurys tristis | C | 19 | 486 | 950 | 1 |
| 20 | Plectreurys tristis | C | 20 | 487 | 951 | 3 |
| 21 | Agelenopsis aperta | C | 21 | 488 | 952 | 2 |
| 22 | Araneus gemmoides | C | 22 | 489 | 953 | 3 |
| 23 | Argiope argentata | C | 23 | 490 | 954 | 1 |
| 24 | Argiope aurantia | C | 24 | 491 | 955 | no data |
| 25 | Argiope bruennichi | C | 25 | 492 | 956 | no data |
| 26 | Argiope bruennichi | C | 26 | 493 | 957 | 1 |
| 27 | Atypoides riversi | C | 27 | 494 | 958 | 1 |
| 28 | Avicularia juruensis | C | 28 | 495 | 959 | 1 |
| 29 | Deinopis Spinosa | C | 29 | 496 | 960 | 2 |
| 30 | Latrodectus hesperus | C | 30 | 497 | 961 | 2 |
| 31 | Nephila antipodiana | C | 31 | 498 | 962 | 2 |
| 32 | Nephila clavata | C | 32 | 499 | 963 | 2 |
| 33 | Nephila clavipes | C | 33 | 500 | 964 | 1 |
| 34 | Nephilengys cruentata | C | 34 | 501 | 965 | 3 |
| 35 | Uloborus diversus | C | 35 | 502 | 966 | no data |
| 36 | Araneus ventricosus | C | 36 | 503 | 967 | 3 |
| 37 | Argiope argentata | C | 37 | 504 | 968 | 3 |
| 38 | Deinopis spinosa | C | 38 | 505 | 969 | 2 |
| 39 | Latrodectus hesperus | C | 39 | 506 | 970 | 3 |
| 40 | Metepeira grandiosa | C | 40 | 507 | 971 | 3 |
| 41 | Nephila antipodiana | C | 41 | 508 | 972 | 3 |
| 42 | Nephila clavipes | C | 42 | 509 | 973 | 3 |
| 43 | Nephilengys cruentata | C | 43 | 510 | 974 | 1 |
| 44 | Parawixia bistriata | C | 44 | 511 | 975 | 3 |
| 45 | Uloborus diversus | C | 45 | 512 | 976 | 2 |
| 46 | Araneus ventricosus | C | 46 | 513 | 977 | no data |
| 47 | Argiope trifasciata | C | 47 | 514 | 978 | 3 |
| 48 | Nephila clavipes | C | 48 | 515 | 979 | 3 |
| 49 | Nephilengys cruentata | C | 49 | 516 | 980 | 3 |
| 50 | Nephila madagascariensis | C | 50 | 517 | 981 | 3 |
| 51 | Latrodectus hesperus | C | 51 | 518 | 982 | 2 |
| 52 | Araneus ventricosus | C | 52 | 519 | 983 | 2 |
| 53 | Argiope trifasciata | C | 53 | 520 | 984 | 2 |
| 54 | Parawixia bistriata | C | 54 | 521 | 985 | 3 |
| 55 | Uloborus diversus | C | 55 | 522 | 986 | 1 |
| 56 | Agelenopsis aperta | C | 56 | 523 | 987 | 3 |
| 57 | Aphonopelma seemanni | C | 57 | 524 | 988 | 1 |
| 58 | Araneus bicentenarius | C | 58 | 525 | 989 | 3 |
| 59 | Araneus ventricosus | C | 59 | 526 | 990 | 2 |
| 60 | Argiope amoena | C | 60 | 527 | 991 | 3 |
| 61 | Argiope amoena | C | 61 | 528 | 992 | no data |
| 62 | Argiope amoena | C | 62 | 529 | 993 | 3 |
| 63 | Argiope amoena | C | 63 | 530 | 994 | 2 |
| 64 | Argiope aurantia | C | 64 | 531 | 995 | 2 |
| 65 | Argiope bruennichi | C | 65 | 532 | 996 | 2 |
| 66 | Argiope bruennichi | C | 66 | 533 | 997 | 3 |
| 67 | Argiope trifasciata | C | 67 | 534 | 998 | 3 |
| 68 | Argiope trifasciata | C | 68 | 535 | 999 | 2 |
| 69 | Avicularia juruensis | C | 69 | 536 | 1000 | 2 |
| 70 | Avicularia juruensis | C | 70 | 537 | 1001 | 3 |
| 71 | Avicularia juruensis | C | 71 | 538 | 1002 | 3 |
| 72 | Deinopis spinosa | C | 72 | 539 | 1003 | 1 |
| 73 | Deinopis spinosa | C | 73 | 540 | 1004 | 2 |
| 74 | Deinopis spinosa | C | 74 | 541 | 1005 | no data |
| 75 | Diguetia canities | C | 75 | 542 | 1006 | 2 |
| 76 | Diguetia canities | C | 76 | 543 | 1007 | 3 |
| 77 | Dolomedes tenebrosus | C | 77 | 544 | 1008 | 3 |
| 78 | Euprosthenops australis | C | 78 | 545 | 1009 | 3 |
| 79 | Euprosthenops australis | C | 79 | 546 | 1010 | 2 |
| 80 | Euprosthenops australis | C | 80 | 547 | 1011 | 2 |
| 81 | Gasteracantha mammosa | C | 81 | 548 | 1012 | 3 |

TABLE 2-continued

Silk polypeptide sequences

| Construct # | Species | N/C/R sequence | Nucleotide SEQ ID NO | Nucleotide with flanking sequences SEQ ID NO: | Amino acid SEQ ID NO: | Western Results (1 = no band 2 = weak band 3 = strong band) |
|---|---|---|---|---|---|---|
| 82 | Hypochilus thorelli | C | 82 | 549 | 1013 | 2 |
| 83 | Megahexura fulva | C | 83 | 550 | 1014 | 2 |
| 84 | Nephila antipodiana | C | 84 | 551 | 1015 | 3 |
| 85 | Nephila clavipes | C | 85 | 552 | 1016 | 3 |
| 86 | Nephila clavipes | C | 86 | 553 | 1017 | no data |
| 87 | Nephila madagascariensis | C | 87 | 554 | 1018 | 3 |
| 88 | Nephila madagascariensis | C | 88 | 555 | 1019 | 3 |
| 89 | Nephila pilipes | C | 89 | 556 | 1020 | 3 |
| 90 | Nephila senegalensis | C | 90 | 557 | 1021 | 3 |
| 91 | Nephilengys cruentata | C | 91 | 558 | 1022 | 2 |
| 92 | Parawixia bistriata | C | 92 | 559 | 1023 | 3 |
| 93 | Parawixia bistriata | C | 93 | 560 | 1024 | 2 |
| 94 | Peucetia viridans | C | 94 | 561 | 1025 | 2 |
| 95 | Poecilotheria regalis | C | 95 | 562 | 1026 | 1 |
| 96 | Tetragnatha kauaiensis | C | 96 | 563 | 1027 | 1 |
| 97 | Tetragnatha versicolor | C | 97 | 564 | 1028 | 2 |
| 98 | Uloborus diversus | C | 98 | 565 | 1029 | 3 |
| 99 | Araneus diadematus | C | 99 | 566 | 1030 | 1 |
| 100 | Araneus diadematus | C | 100 | 567 | 1031 | 3 |
| 101 | Araneus diadematus | C | 101 | 568 | 1032 | 2 |
| 102 | Araneus diadematus | C | 102 | 569 | 1033 | 3 |
| 103 | Araneus diadematus | C | 103 | 570 | 1034 | 3 |
| 104 | Araneus diadematus | C | 104 | 571 | 1035 | 3 |
| 105 | Araneus diadematus | C | 105 | 572 | 1036 | 2 |
| 106 | Araneus diadematus | C | 106 | 573 | 1037 | 3 |
| 107 | Araneus diadematus | C | 107 | 574 | 1038 | 3 |
| 108 | Agelenopsis aperta | N | 108 | 575 | 1039 | 3 |
| 109 | Argiope argentata | N | 109 | 576 | 1040 | 3 |
| 110 | Argiope bruennichi | N | 110 | 577 | 1041 | 1 |
| 111 | Argiope bruennichi | N | 111 | 578 | 1042 | 2 |
| 112 | Latrodectus hesperus | N | 112 | 579 | 1043 | 1 |
| 113 | Nephila clavata | N | 113 | 580 | 1044 | 3 |
| 114 | Araneus ventricosus | N | 114 | 581 | 1045 | 3 |
| 115 | Metepeira grandiosa | N | 115 | 582 | 1046 | 3 |
| 116 | Uloborus diversus | N | 116 | 583 | 1047 | 3 |
| 117 | Nephila clavipes | N | 117 | 584 | 1048 | 3 |
| 118 | Nephila madagascariensis | N | 118 | 585 | 1049 | 3 |
| 119 | Latrodectus hesperus | N | 119 | 586 | 1050 | 2 |
| 120 | Latrodectus hesperus | N | 120 | 587 | 1051 | 2 |
| 121 | Agelenopsis aperta | N | 121 | 588 | 1052 | 1 |
| 122 | Argiope bruennichi | N | 122 | 589 | 1053 | 3 |
| 123 | Argiope trifasciata | N | 123 | 590 | 1054 | 3 |
| 124 | Bothriocyrtum californicum | N | 124 | 591 | 1055 | 2 |
| 125 | Deinopis spinosa | N | 125 | 592 | 1056 | 3 |
| 126 | Diguetia canities | N | 126 | 593 | 1057 | 3 |
| 127 | Diguetia canities | N | 127 | 594 | 1058 | 3 |
| 128 | Euprosthenops australis | N | 128 | 595 | 1059 | 3 |
| 129 | Kukulcania hibernalis | N | 129 | 596 | 1060 | 1 |
| 130 | Kukulcania hibernalis | N | 130 | 597 | 1061 | 3 |
| 131 | Nephila clavipes | N | 131 | 598 | 1062 | 3 |
| 132 | Nephila clavipes | N | 132 | 599 | 1063 | 3 |
| 133 | Nephila clavipes | N | 133 | 600 | 1064 | 3 |
| 134 | Nephila madagascariensis | N | 134 | 601 | 1065 | 3 |
| 135 | Araneus diadematus | N | 135 | 602 | 1066 | 3 |
| 136 | Araneus diadematus | N | 136 | 603 | 1067 | 2 |
| 137 | Araneus diadematus | N | 137 | 604 | 1068 | 3 |
| 138 | Araneus diadematus | N | 138 | 605 | 1069 | 2 |
| 139 | Araneus diadematus | N | 139 | 606 | 1070 | 2 |
| 140 | Araneus diadematus | N | 140 | 607 | 1071 | 3 |
| 141 | Araneus diadematus | N | 141 | 608 | 1072 | 1 |
| 142 | Araneus diadematus | N | 142 | 609 | 1073 | 3 |
| 143 | Araneus diadematus | N | 143 | 610 | 1074 | 2 |
| 144 | Araneus diadematus | N | 144 | 611 | 1075 | 2 |
| 145 | Araneus diadematus | N | 145 | 612 | 1076 | 3 |
| 146 | Aliatypus gulosus | R | 146 | 613 | 1077 | 3 |
| 147 | Aliatypus gulosus | R | 147 | 614 | 1078 | 3 |
| 148 | Aliatypus gulosus | R | 148 | 615 | 1079 | 3 |
| 149 | Aliatypus gulosus | R | 149 | 616 | 1080 | 3 |
| 150 | Aliatypus gulosus | R | 150 | 617 | 1081 | 3 |
| 151 | Aliatypus gulosus | R | 151 | 618 | 1082 | 3 |
| 152 | Aliatypus gulosus | R | 152 | 619 | 1083 | 3 |
| 153 | Aptostichus sp. AS217 | R | 153 | 620 | 1084 | 3 |
| 154 | Aptostichus sp. AS217 | R | 154 | 621 | 1085 | 3 |

TABLE 2-continued

Silk polypeptide sequences

| Construct # | Species | N/C/R sequence | Nucleotide SEQ ID NO | Nucleotide with flanking sequences SEQ ID NO: | Amino acid SEQ ID NO: | Western Results (1 = no band 2 = weak band 3 = strong band) |
|---|---|---|---|---|---|---|
| 155 | Aptostichus sp. AS217 | R | 155 | 622 | 1086 | 3 |
| 156 | Aptostichus sp. AS217 | R | 156 | 623 | 1087 | 3 |
| 157 | Aptostichus sp. AS217 | R | 157 | 624 | 1088 | 3 |
| 158 | Aptostichus sp. AS220 | R | 158 | 625 | 1089 | 2 |
| 159 | Aptostichus sp. AS220 | R | 159 | 626 | 1090 | 3 |
| 160 | Aptostichus sp. AS220 | R | 160 | 627 | 1091 | 3 |
| 161 | Araneus diadematus | R | 161 | 628 | 1092 | 3 |
| 162 | Araneus diadematus | R | 162 | 629 | 1093 | 2 |
| 163 | Araneus diadematus | R | 163 | 630 | 1094 | 2 |
| 164 | Araneus diadematus | R | 164 | 631 | 1095 | 2 |
| 165 | Araneus diadematus | R | 165 | 632 | 1096 | 2 |
| 166 | Atypoides riversi | R | 166 | 633 | 1097 | 3 |
| 167 | Atypoides riversi | R | 167 | 634 | 1098 | 3 |
| 168 | Atypoides riversi | R | 168 | 635 | 1099 | 2 |
| 169 | Atypoides riversi | R | 169 | 636 | 1100 | 3 |
| 170 | Atypoides riversi | R | 170 | 637 | 1101 | no data |
| 171 | Atypoides riversi | R | 171 | 638 | 1102 | 1 |
| 172 | Atypoides riversi | R | 172 | 639 | 1103 | 3 |
| 173 | Bothriocyrtum californicum | R | 173 | 640 | 1104 | 3 |
| 174 | Bothriocyrtum californicum | R | 174 | 641 | 1105 | 3 |
| 175 | Bothriocyrtum californicum | R | 175 | 642 | 1106 | 3 |
| 176 | Bothriocyrtum californicum | R | 176 | 643 | 1107 | 3 |
| 177 | Bothriocyrtum californicum | R | 177 | 644 | 1108 | 3 |
| 178 | Bothriocyrtum californicum | R | 178 | 645 | 1109 | 3 |
| 179 | Bothriocyrtum californicum | R | 179 | 646 | 1110 | 3 |
| 180 | Bothriocyrtum californicum | R | 180 | 647 | 1111 | 3 |
| 181 | Bothriocyrtum californicum | R | 181 | 648 | 1112 | 3 |
| 182 | Bothriocyrtum californicum | R | 182 | 649 | 1113 | 3 |
| 183 | Deinopis Spinosa | R | 183 | 650 | 1114 | 3 |
| 184 | Deinopis Spinosa | R | 184 | 651 | 1115 | 2 |
| 185 | Deinopis Spinosa | R | 185 | 652 | 1116 | 3 |
| 186 | Deinopis Spinosa | R | 186 | 653 | 1117 | 3 |
| 187 | Deinopis Spinosa | R | 187 | 654 | 1118 | 3 |
| 188 | Deinopis Spinosa | R | 188 | 655 | 1119 | no data |
| 189 | Deinopis Spinosa | R | 189 | 656 | 1120 | 2 |
| 190 | Deinopis Spinosa | R | 190 | 657 | 1121 | 3 |
| 191 | Dolomedes tenebrosus | R | 191 | 658 | 1122 | 2 |
| 192 | Dolomedes tenebrosus | R | 192 | 659 | 1123 | no data |
| 193 | Dolomedes tenebrosus | R | 193 | 660 | 1124 | 3 |
| 194 | Euagrus chisoseus | R | 194 | 661 | 1125 | 2 |
| 195 | Euagrus chisoseus | R | 195 | 662 | 1126 | 2 |
| 196 | Euagrus chisoseus | R | 196 | 663 | 1127 | 2 |
| 197 | Plectreurys tristis | R | 197 | 664 | 1128 | 3 |
| 198 | Plectreurys tristis | R | 198 | 665 | 1129 | 3 |
| 199 | Plectreurys tristis | R | 199 | 666 | 1130 | 3 |
| 200 | Plectreurys tristis | R | 200 | 667 | 1131 | 2 |
| 201 | Plectreurys tristis | R | 201 | 668 | 1132 | 3 |
| 202 | Plectreurys tristis | R | 202 | 669 | 1133 | 3 |
| 203 | Plectreurys tristis | R | 203 | 670 | 1134 | 2 |
| 204 | Plectreurys tristis | R | 204 | 671 | 1135 | 3 |
| 205 | Plectreurys tristis | R | 205 | 672 | 1136 | 3 |
| 206 | Plectreurys tristis | R | 206 | 673 | 1137 | 3 |
| 207 | Plectreurys tristis | R | 207 | 674 | 1138 | 3 |
| 208 | Plectreurys tristis | R | 208 | 675 | 1139 | 2 |
| 209 | Plectreurys tristis | R | 209 | 676 | 1140 | 3 |
| 210 | Plectreurys tristis | R | 210 | 677 | 1141 | 3 |
| 211 | Plectreurys tristis | R | 211 | 678 | 1142 | 3 |
| 212 | Plectreurys tristis | R | 212 | 679 | 1143 | 3 |
| 213 | Plectreurys tristis | R | 213 | 680 | 1144 | 3 |
| 214 | Plectreurys tristis | R | 214 | 681 | 1145 | 3 |
| 215 | Plectreurys tristis | R | 215 | 682 | 1146 | 3 |
| 216 | Agelenopsis aperta | R | 216 | 683 | 1147 | 3 |
| 217 | Agelenopsis aperta | R | 217 | 684 | 1148 | 3 |
| 218 | Araneus gemmoides | R | 218 | 685 | 1149 | 2 |
| 219 | Araneus gemmoides | R | 219 | 686 | 1150 | 3 |
| 220 | Araneus gemmoides | R | 220 | 687 | 1151 | 2 |
| 221 | Argiope amoena | R | 221 | 688 | 1152 | no data |
| 222 | Argiope amoena | R | 222 | 689 | 1153 | 3 |
| 223 | Argiope argentata | R | 223 | 690 | 1154 | 2 |
| 224 | Argiope argentata | R | 224 | 691 | 1155 | 2 |
| 225 | Argiope argentata | R | 225 | 692 | 1156 | 2 |
| 226 | Argiope aurantia | R | 226 | 693 | 1157 | 2 |
| 227 | Argiope aurantia | R | 227 | 694 | 1158 | 2 |

TABLE 2-continued

Silk polypeptide sequences

| Construct # | Species | N/C/R sequence | Nucleotide SEQ ID NO | Nucleotide with flanking sequences SEQ ID NO: | Amino acid SEQ ID NO: | Western Results (1 = no band 2 = weak band 3 = strong band) |
|---|---|---|---|---|---|---|
| 228 | Argiope aurantia | R | 228 | 695 | 1159 | 2 |
| 229 | Argiope aurantia | R | 229 | 696 | 1160 | 2 |
| 230 | Argiope bruennichi | R | 230 | 697 | 1161 | 2 |
| 231 | Argiope bruennichi | R | 231 | 698 | 1162 | 2 |
| 232 | Argiope bruennichi | R | 232 | 699 | 1163 | 2 |
| 233 | Argiope bruennichi | R | 233 | 700 | 1164 | 2 |
| 234 | Argiope bruennichi | R | 234 | 701 | 1165 | 3 |
| 235 | Argiope bruennichi | R | 235 | 702 | 1166 | 2 |
| 236 | Argiope bruennichi | R | 236 | 703 | 1167 | 2 |
| 237 | Argiope bruennichi | R | 237 | 704 | 1168 | 2 |
| 238 | Argiope bruennichi | R | 238 | 705 | 1169 | 2 |
| 239 | Argiope bruennichi | R | 239 | 706 | 1170 | 3 |
| 240 | Argiope bruennichi | R | 240 | 707 | 1171 | 2 |
| 241 | Argiope bruennichi | R | 241 | 708 | 1172 | 2 |
| 242 | Argiope bruennichi | R | 242 | 709 | 1173 | 3 |
| 243 | Argiope bruennichi | R | 243 | 710 | 1174 | 2 |
| 244 | Argiope bruennichi | R | 244 | 711 | 1175 | 3 |
| 245 | Argiope bruennichi | R | 245 | 712 | 1176 | 2 |
| 246 | Argiope bruennichi | R | 246 | 713 | 1177 | 2 |
| 247 | Argiope bruennichi | R | 247 | 714 | 1178 | 3 |
| 248 | Argiope bruennichi | R | 248 | 715 | 1179 | 2 |
| 249 | Argiope bruennichi | R | 249 | 716 | 1180 | 2 |
| 250 | Atypoides riversi | R | 250 | 717 | 1181 | 2 |
| 251 | Atypoides riversi | R | 251 | 718 | 1182 | 2 |
| 252 | Atypoides riversi | R | 252 | 719 | 1183 | 3 |
| 253 | Atypoides riversi | R | 253 | 720 | 1184 | 1 |
| 254 | Atypoides riversi | R | 254 | 721 | 1185 | 2 |
| 255 | Atypoides riversi | R | 255 | 722 | 1186 | 2 |
| 256 | Atypoides riversi | R | 256 | 723 | 1187 | 2 |
| 257 | Avicularia juruensis | R | 257 | 724 | 1188 | 2 |
| 258 | Avicularia juruensis | R | 258 | 725 | 1189 | 1 |
| 259 | Avicularia juruensis | R | 259 | 726 | 1190 | 1 |
| 260 | Deinopis Spinosa | R | 260 | 727 | 1191 | 3 |
| 261 | Deinopis Spinosa | R | 261 | 728 | 1192 | 3 |
| 262 | Deinopis Spinosa | R | 262 | 729 | 1193 | 2 |
| 263 | Latrodectus hesperus | R | 263 | 730 | 1194 | 3 |
| 264 | Latrodectus hesperus | R | 264 | 731 | 1195 | 3 |
| 265 | Latrodectus hesperus | R | 265 | 732 | 1196 | 2 |
| 266 | Latrodectus hesperus | R | 266 | 733 | 1197 | 1 |
| 267 | Latrodectus hesperus | R | 267 | 734 | 1198 | 1 |
| 268 | Latrodectus hesperus | R | 268 | 735 | 1199 | 2 |
| 269 | Nephila antipodiana | R | 269 | 736 | 1200 | 3 |
| 270 | Nephila clavata | R | 270 | 737 | 1201 | 2 |
| 271 | Nephila clavata | R | 271 | 738 | 1202 | no data |
| 272 | Nephila clavata | R | 272 | 739 | 1203 | 2 |
| 273 | Nephila clavata | R | 273 | 740 | 1204 | 2 |
| 274 | Nephila clavata | R | 274 | 741 | 1205 | 1 |
| 275 | Nephila clavata | R | 275 | 742 | 1206 | 1 |
| 276 | Nephila clavata | R | 276 | 743 | 1207 | 2 |
| 277 | Nephila clavata | R | 277 | 744 | 1208 | 1 |
| 278 | Nephila clavipes | R | 278 | 745 | 1209 | 2 |
| 279 | Nephila clavipes | R | 279 | 746 | 1210 | 2 |
| 280 | Nephilengys cruentata | R | 280 | 747 | 1211 | no data |
| 281 | Uloborus diversus | R | 281 | 748 | 1212 | 3 |
| 282 | Uloborus diversus | R | 282 | 749 | 1213 | 1 |
| 283 | Uloborus diversus | R | 283 | 750 | 1214 | 3 |
| 284 | Uloborus diversus | R | 284 | 751 | 1215 | 1 |
| 285 | Araneus ventricosus | R | 285 | 752 | 1216 | 2 |
| 286 | Araneus ventricosus | R | 286 | 753 | 1217 | 3 |
| 287 | Araneus ventricosus | R | 287 | 754 | 1218 | 2 |
| 288 | Araneus ventricosus | R | 288 | 755 | 1219 | 2 |
| 289 | Araneus ventricosus | R | 289 | 756 | 1220 | 3 |
| 290 | Araneus ventricosus | R | 290 | 757 | 1221 | 2 |
| 291 | Araneus ventricosus | R | 291 | 758 | 1222 | 3 |
| 292 | Araneus ventricosus | R | 292 | 759 | 1223 | 3 |
| 293 | Argiope argentata | R | 293 | 760 | 1224 | 3 |
| 294 | Deinopis spinosa | R | 294 | 761 | 1225 | 2 |
| 295 | Latrodectus hesperus | R | 295 | 762 | 1226 | 3 |
| 296 | Latrodectus hesperus | R | 296 | 763 | 1227 | 3 |
| 297 | Metepeira grandiosa | R | 297 | 764 | 1228 | 2 |
| 298 | Metepeira grandiosa | R | 298 | 765 | 1229 | 3 |
| 299 | Nephila antipodiana | R | 299 | 766 | 1230 | 2 |
| 300 | Nephila clavipes | R | 300 | 767 | 1231 | 3 |

TABLE 2-continued

Silk polypeptide sequences

| Construct # | Species | N/C/R sequence | Nucleotide SEQ ID NO | Nucleotide with flanking sequences SEQ ID NO: | Amino acid SEQ ID NO: | Western Results (1 = no band 2 = weak band 3 = strong band) |
|---|---|---|---|---|---|---|
| 301 | Nephila clavipes | R | 301 | 768 | 1232 | 3 |
| 302 | Nephila clavipes | R | 302 | 769 | 1233 | 2 |
| 303 | Nephila clavipes | R | 303 | 770 | 1234 | 3 |
| 304 | Nephilengys cruentata | R | 304 | 771 | 1235 | 2 |
| 305 | Nephilengys cruentata | R | 305 | 772 | 1236 | 3 |
| 306 | Nephilengys cruentata | R | 306 | 773 | 1237 | 3 |
| 307 | Nephilengys cruentata | R | 307 | 774 | 1238 | no data |
| 308 | Nephilengys cruentata | R | 308 | 775 | 1239 | 3 |
| 309 | Nephilengys cruentata | R | 309 | 776 | 1240 | 2 |
| 310 | Nephilengys cruentata | R | 310 | 777 | 1241 | 3 |
| 311 | Nephilengys cruentata | R | 311 | 778 | 1242 | 3 |
| 312 | Nephilengys cruentata | R | 312 | 779 | 1243 | 2 |
| 313 | Parawixia bistriata | R | 313 | 780 | 1244 | 3 |
| 314 | Parawixia bistriata | R | 314 | 781 | 1245 | 3 |
| 315 | Uloborus diversus | R | 315 | 782 | 1246 | 3 |
| 316 | Uloborus diversus | R | 316 | 783 | 1247 | 3 |
| 317 | Uloborus diversus | R | 317 | 784 | 1248 | 3 |
| 318 | Uloborus diversus | R | 318 | 785 | 1249 | 2 |
| 319 | Araneus ventricosus | R | 319 | 786 | 1250 | 2 |
| 320 | Argiope trifasciata | R | 320 | 787 | 1251 | 3 |
| 321 | Argiope trifasciata | R | 321 | 788 | 1252 | 3 |
| 322 | Argiope trifasciata | R | 322 | 789 | 1253 | 3 |
| 323 | Nephila clavipes | R | 323 | 790 | 1254 | 2 |
| 324 | Nephila clavipes | R | 324 | 791 | 1255 | 3 |
| 325 | Nephila clavipes | R | 325 | 792 | 1256 | 3 |
| 326 | Nephila clavipes | R | 326 | 793 | 1257 | 3 |
| 327 | Nephila clavipes | R | 327 | 794 | 1258 | 3 |
| 328 | Nephila clavipes | R | 328 | 795 | 1259 | 3 |
| 329 | Nephilengys cruentata | R | 329 | 796 | 1260 | 3 |
| 330 | Nephilengys cruentata | R | 330 | 797 | 1261 | 2 |
| 331 | Nephilengys cruentata | R | 331 | 798 | 1262 | 1 |
| 332 | Nephila madagascariensis | R | 332 | 799 | 1263 | 2 |
| 333 | Nephila madagascariensis | R | 333 | 800 | 1264 | 3 |
| 334 | Nephila madagascariensis | R | 334 | 801 | 1265 | 2 |
| 335 | Nephila madagascariensis | R | 335 | 802 | 1266 | 3 |
| 336 | Nephila madagascariensis | R | 336 | 803 | 1267 | 1 |
| 337 | Nephila madagascariensis | R | 337 | 804 | 1268 | no data |
| 338 | Nephila madagascariensis | R | 338 | 805 | 1269 | 2 |
| 339 | Nephila madagascariensis | R | 339 | 806 | 1270 | 2 |
| 340 | Latrodectus hesperus | R | 340 | 807 | 1271 | 3 |
| 341 | Latrodectus hesperus | R | 341 | 808 | 1272 | 2 |
| 342 | Latrodectus hesperus | R | 342 | 809 | 1273 | 3 |
| 343 | Latrodectus hesperus | R | 343 | 810 | 1274 | 2 |
| 344 | Latrodectus hesperus | R | 344 | 811 | 1275 | no data |
| 345 | Latrodectus hesperus | R | 345 | 812 | 1276 | 2 |
| 346 | Latrodectus hesperus | R | 346 | 813 | 1277 | 3 |
| 347 | Latrodectus hesperus | R | 347 | 814 | 1278 | 3 |
| 348 | Latrodectus hesperus | R | 348 | 815 | 1279 | 3 |
| 349 | Latrodectus hesperus | R | 349 | 816 | 1280 | 2 |
| 350 | Argiope amoena | R | 350 | 817 | 1281 | 3 |
| 351 | Argiope amoena | R | 351 | 818 | 1282 | 3 |
| 352 | Argiope amoena | R | 352 | 819 | 1283 | 3 |
| 353 | Argiope amoena | R | 353 | 820 | 1284 | 3 |
| 354 | Araneus ventricosus | R | 354 | 821 | 1285 | 3 |
| 355 | Araneus ventricosus | R | 355 | 822 | 1286 | 3 |
| 356 | Araneus ventricosus | R | 356 | 823 | 1287 | 3 |
| 357 | Araneus ventricosus | R | 357 | 824 | 1288 | 3 |
| 358 | Araneus ventricosus | R | 358 | 825 | 1289 | 3 |
| 359 | Araneus ventricosus | R | 359 | 826 | 1290 | 3 |
| 360 | Araneus ventricosus | R | 360 | 827 | 1291 | 3 |
| 361 | Araneus ventricosus | R | 361 | 828 | 1292 | 3 |
| 362 | Argiope trifasciata | R | 362 | 829 | 1293 | 3 |
| 363 | Argiope trifasciata | R | 363 | 830 | 1294 | 3 |
| 364 | Argiope trifasciata | R | 364 | 831 | 1295 | 3 |
| 365 | Argiope trifasciata | R | 365 | 832 | 1296 | 3 |
| 366 | Argiope trifasciata | R | 366 | 833 | 1297 | 3 |
| 367 | Argiope trifasciata | R | 367 | 834 | 1298 | 3 |
| 368 | Argiope trifasciata | R | 368 | 835 | 1299 | 3 |
| 369 | Argiope trifasciata | R | 369 | 836 | 1300 | 3 |
| 370 | Parawixia bistriata | R | 370 | 837 | 1301 | 3 |
| 371 | Parawixia bistriata | R | 371 | 838 | 1302 | 3 |
| 372 | Uloborus diversus | R | 372 | 839 | 1303 | 3 |
| 373 | Uloborus diversus | R | 373 | 840 | 1304 | 3 |

TABLE 2-continued

Silk polypeptide sequences

| Construct # | Species | N/C/R sequence | Nucleotide SEQ ID NO | Nucleotide with flanking sequences SEQ ID NO: | Amino acid SEQ ID NO: | Western Results (1 = no band 2 = weak band 3 = strong band) |
|---|---|---|---|---|---|---|
| 374 | Uloborus diversus | R | 374 | 841 | 1305 | 3 |
| 375 | Uloborus diversus | R | 375 | 842 | 1306 | 3 |
| 376 | Agelenopsis aperta | R | 376 | 843 | 1307 | 3 |
| 377 | Agelenopsis aperta | R | 377 | 844 | 1308 | 3 |
| 378 | Agelenopsis aperta | R | 378 | 845 | 1309 | 2 |
| 379 | Agelenopsis aperta | R | 379 | 846 | 1310 | 2 |
| 380 | Aphonopelma seemanni | R | 380 | 847 | 1311 | 3 |
| 381 | Araneus ventricosus | R | 381 | 848 | 1312 | 3 |
| 382 | Argiope aurantia | R | 382 | 849 | 1313 | 3 |
| 383 | Argiope bruennichi | R | 383 | 850 | 1314 | 3 |
| 384 | Argiope bruennichi | R | 384 | 851 | 1315 | 3 |
| 385 | Argiope bruennichi | R | 385 | 852 | 1316 | 3 |
| 386 | Argiope bruennichi | R | 386 | 853 | 1317 | 3 |
| 387 | Argiope bruennichi | R | 387 | 854 | 1318 | 3 |
| 388 | Argiope bruennichi | R | 388 | 855 | 1319 | 3 |
| 389 | Argiope bruennichi | R | 389 | 856 | 1320 | 3 |
| 390 | Argiope bruennichi | R | 390 | 857 | 1321 | 3 |
| 391 | Argiope bruennichi | R | 391 | 858 | 1322 | 3 |
| 392 | Argiope bruennichi | R | 392 | 859 | 1323 | 3 |
| 393 | Argiope bruennichi | R | 393 | 860 | 1324 | 3 |
| 394 | Argiope trifasciata | R | 394 | 861 | 1325 | 3 |
| 395 | Argiope trifasciata | R | 395 | 862 | 1326 | 3 |
| 396 | Argiope trifasciata | R | 396 | 863 | 1327 | 1 |
| 397 | Argiope trifasciata | R | 397 | 864 | 1328 | 2 |
| 398 | Argiope trifasciata | R | 398 | 865 | 1329 | 1 |
| 399 | Argiope trifasciata | R | 399 | 866 | 1330 | 3 |
| 400 | Argiope trifasciata | R | 400 | 867 | 1331 | 1 |
| 401 | Avicularia juruensis | R | 401 | 868 | 1332 | 3 |
| 402 | Avicularia juruensis | R | 402 | 869 | 1333 | no data |
| 403 | Avicularia juruensis | R | 403 | 870 | 1334 | 3 |
| 404 | Deinopis spinosa | R | 404 | 871 | 1335 | 3 |
| 405 | Deinopis spinosa | R | 405 | 872 | 1336 | 2 |
| 406 | Deinopis spinosa | R | 406 | 873 | 1337 | 3 |
| 407 | Deinopis spinosa | R | 407 | 874 | 1338 | 2 |
| 408 | Deinopis spinosa | R | 408 | 875 | 1339 | no data |
| 409 | Deinopis spinosa | R | 409 | 876 | 1340 | 3 |
| 410 | Diguetia canities | R | 410 | 877 | 1341 | 3 |
| 411 | Diguetia canities | R | 411 | 878 | 1342 | 3 |
| 412 | Diguetia canities | R | 412 | 879 | 1343 | 3 |
| 413 | Dolomedes tenebrosus | R | 413 | 880 | 1344 | 2 |
| 414 | Dolomedes tenebrosus | R | 414 | 881 | 1345 | 3 |
| 415 | Dolomedes tenebrosus | R | 415 | 882 | 1346 | 3 |
| 416 | Euprosthenops australis | R | 416 | 883 | 1347 | 2 |
| 417 | Euprosthenops australis | R | 417 | 884 | 1348 | 1 |
| 418 | Euprosthenops australis | R | 418 | 885 | 1349 | 3 |
| 419 | Euprosthenops australis | R | 419 | 886 | 1350 | 2 |
| 420 | Euprosthenops australis | R | 420 | 887 | 1351 | 3 |
| 421 | Euprosthenops australis | R | 421 | 888 | 1352 | 3 |
| 422 | Euprosthenops australis | R | 422 | 889 | 1353 | 3 |
| 423 | Euprosthenops australis | R | 423 | 890 | 1354 | 3 |
| 424 | Euprosthenops australis | R | 424 | 891 | 1355 | 3 |
| 425 | Gasteracantha mammosa | R | 425 | 892 | 1356 | 1 |
| 426 | Hypochilus thorelli | R | 426 | 893 | 1357 | 3 |
| 427 | Hypochilus thorelli | R | 427 | 894 | 1358 | 3 |
| 428 | Kukulcania hibernalis | R | 428 | 895 | 1359 | 3 |
| 429 | Kukulcania hibernalis | R | 429 | 896 | 1360 | 3 |
| 430 | Megahexura fulva | R | 430 | 897 | 1361 | no data |
| 431 | Megahexura fulva | R | 431 | 898 | 1362 | 3 |
| 432 | Megahexura fulva | R | 432 | 899 | 1363 | no data |
| 433 | Megahexura fulva | R | 433 | 900 | 1364 | 3 |
| 434 | Megahexura fulva | R | 434 | 901 | 1365 | 3 |
| 435 | Megahexura fulva | R | 435 | 902 | 1366 | 3 |
| 436 | Nephila clavipes | R | 436 | 903 | 1367 | 1 |
| 437 | Nephila clavipes | R | 437 | 904 | 1368 | 3 |
| 438 | Nephila clavipes | R | 438 | 905 | 1369 | 3 |
| 439 | Nephila clavipes | R | 439 | 906 | 1370 | 3 |
| 440 | Nephila clavipes | R | 440 | 907 | 1371 | 1 |
| 441 | Nephila madagascariensis | R | 441 | 908 | 1372 | 3 |
| 442 | Nephila madagascariensis | R | 442 | 909 | 1373 | 3 |
| 443 | Nephila madagascariensis | R | 443 | 910 | 1374 | 3 |
| 444 | Nephila madagascariensis | R | 444 | 911 | 1375 | 3 |
| 445 | Nephila madagascariensis | R | 445 | 912 | 1376 | 2 |
| 446 | Nephila madagascariensis | R | 446 | 913 | 1377 | 2 |

TABLE 2-continued

Silk polypeptide sequences

| Construct # | Species | N/C/R sequence | Nucleotide SEQ ID NO | Nucleotide with flanking sequences SEQ ID NO: | Amino acid SEQ ID NO: | Western Results (1 = no band 2 = weak band 3 = strong band) |
|---|---|---|---|---|---|---|
| 447 | Nephila madagascariensis | R | 447 | 914 | 1378 | 2 |
| 448 | Nephila madagascariensis | R | 448 | 915 | 1379 | 2 |
| 449 | Nephila madagascariensis | R | 449 | 916 | 1380 | 2 |
| 450 | Nephila pilipes | R | 450 | 917 | 1381 | no data |
| 451 | Nephilengys cruentata | R | 451 | 918 | 1382 | 3 |
| 452 | Nephilengys cruentata | R | 452 | 919 | 1383 | 2 |
| 453 | Parawixia bistriata | R | 453 | 920 | 1384 | 2 |
| 454 | Parawixia bistriata | R | 454 | 921 | 1385 | 2 |
| 455 | Parawixia bistriata | R | 455 | 922 | 1386 | 3 |
| 456 | Parawixia bistriata | R | 456 | 923 | 1387 | 2 |
| 457 | Peucetia viridans | R | 457 | 924 | 1388 | 3 |
| 458 | Poecilotheria regalis | R | 458 | 925 | 1389 | 2 |
| 459 | Poecilotheria regalis | R | 459 | 926 | 1390 | 2 |
| 460 | Poecilotheria regalis | R | 460 | 927 | 1391 | no data |
| 461 | Tetragnatha kauaiensis | R | 461 | 928 | 1392 | 2 |
| 462 | Uloborus diversus | R | 462 | 929 | 1393 | 1 |
| RM409 | Argiope bruennichi | R | 463 | 930 | 1394 | no data |
| RM410 | Argiope bruennichi | R | 464 | 931 | 1395 | no data |
| RM411 | Argiope bruennichi | R | 465 | N/A | 1396 | no data |
| RM434 | Argiope bruennichi | R | 466 | N/A | 1397 | no data |
| RM439 | Argiope bruennichi | R | 467 | N/A | 1398 | 3 |

Example 4

Amplification of N, R, and C Sequences for Insertion into an Assembly Vector

The DNA for N, R, and C sequences were PCR amplified from the expression vector and ligated into assembly vectors using AscI/SbfI restriction sites.

The forward primer consisted of the sequence: 5'-CTAAGAGGCGCGCCTAAGCGATGGTCTCAA-3' (SEQ ID NO: 2827)+the first 19 bp of the N, R, or C sequence.

The reverse primer consisted of the last 17 bp of the N, R, or C sequence+3'-GGTACGTCTTCATCGCTATCCTGCAGGCTACGT-5' (SEQ ID NO: 2828).

For example, for sequence:

(SEQ ID NO: 4)
GGTGCAGGTGCAAGGGCTGCTGGAGGCTACGGTGGAGGATACGGTGCCGG

TGCGGGTGCAGGAGCCGGCGCCGCAGCTTCCGCCGGAGCCTCCGGTGGAT

ACGGAGGTGGATATGGTGGCGGAGCTGGTGCTGGTGCCGTAGCAGGTGCC

TCAGCTGGAAGCTACGGAGGTGCTGTTAATAGACTGAGTTCCGCAGGTGC

AGCCTCTAGAGTGTCGTCCAACGTCGCAGCCATTGCATCTGCTGGTGCTG

CCGCTTTGCCCAACGTTATTTCCAACATCTATAGTGGTGTTCTTTCATCT

GGCGTGTCATCCTCCGAAGCACTTATTCAGGCTTTGTTAGAAGTAATCAG

TGCTTTAATTCATGTCTTAGGATCAGCTTCTATCGGCAACGTTTCATCTG

TTGGTGTTAATTCCGCACTTAATGCTGTGCAAAACGCCGTAGGCGCCTAT

GCCGGA the primers used were:

Fwd:
(SEQ ID NO: 2829)
5'-CTAAGAGGCGCGCCTAAGCGATGGTCTCAAGGTGCAGGTGCAAGGG
CTG-3'

Rev:
(SEQ ID NO: 2830)
3'-TAGGCGCCTATGCCGGAGGTACGTCTTCATCGCTATCCTGCAGGCTA
CGT-5'

The PCR reaction solution consisted of 12.5 μL 2×KOD Extreme Buffer, 0.25 μl KOD Extreme Hot Start Polymerase, 0.5 μl 10 μM Fwd oligo, 0.5 μl 10 μM Rev oligo, 5 ng template DNA (expression vector), 0.5 μl of 10 mM dNTPs, and ddH2O added to final volume of 25 μl. The reaction was then thermocycled according to the program:

1. Denature at 94° C. for 5 minutes
2. Denature at 94° C. for 30 seconds
3. Anneal at 55° C. for 30 seconds
4. Extend at 72° C. for 30 seconds
5. Repeat steps 2-4 for 29 additional cycles
6. Final extension at 72° C. for 5 minutes Resulting PCR products were digested with restriction enzymes AscI and SbfI, and ligated into an assembly vector (see description in Example 5), one of KC (RM396, SEQ ID NO:1402), KA (RM397, SEQ ID NO:1403), AC (RM398, SEQ ID NO:1404), AK (RM399, SEQ ID NO:1405), CA (RM400, SEQ ID NO:1406), or CK (RM401, SEQ ID NO:1407) that had been digested with the same enzymes to release an unwanted insert using routine methods.

Example 5

Synthesis of Silk from Argiope bruennichi MaSp2 Blocks (RM439, "18B")

Using the algorithm described in Example 2, a set of 6 repeat blocks (or block co-polymer) from Argiope bruennichi MaSp2 were selected and divided into 2 R sequences consisting of 3 blocks each. The two 3-block R sequences were then synthesized from short oligonucleotides as follows:

Synthesis of RM409 Sequence:

The Argiope bruennichi MaSp2 block sequences were generated using methodology distinct from that employed in Example 3. Oligos RM2919-RM2942 (SEQ ID NOs: 1468-1491) in Table 3 were combined into a single mixture with equal amounts of each oligo, 100 µM in total. The oligos were phosphorylated in a phosphorylation reaction prepared plasmid isolation, and sequence verification according to known techniques.

The resulting oligonucleotide has a 5' to 3' nucleotide sequence of SEQ ID NO: 930 and is identified as RM409.

TABLE 3

Oligo sequences for generating RM409 silk repeat domain (with flanking sequences for cloning) (SEQ ID NO: 930)

| SEQ ID NO: | ID | 5' to 3' Nucleotide Sequence |
|---|---|---|
| 1469 | RM2919 | CGCGCCTTAGCGATGGTCTCAAGGTGGTTACGGTCCAGGCGCTGGTCAACAAGGTCCA |
| 1470 | RM2920 | GGAAGTGGTGGTCAACAAGGACCTGGCGGTCAAGGACCCTACGGTAGTGG |
| 1471 | RM2921 | CCAACAAGGTCCAGGTGGAGCAGGACAGCAGGGTCCGGGAGGCCAAGGAC |
| 1472 | RM2922 | CTTACGGACCAGGTGCTGCTGCTGCCGCCGCTGCCGCTGCCGGAGGTTACGGT |
| 1473 | RM2923 | CCAGGAGCCGGACAACAGGGTCCAGGTGGAGCTGGACAACAAGGTCC |
| 1474 | RM2924 | AGGATCACAAGGTCCTGGTGGACAAGGTCCATACGGTCCTGGTGCTGGTC |
| 1475 | RM2925 | AACAGGGACCAGGTAGTCAAGGACCTGGTTCAGGTGGTCAGCAGGGTCCAG |
| 1476 | RM2926 | GAGGACAGGGTCCTTACGGCCCTTCTGCCGCTGCAGCAGCAGCCGCTG |
| 1477 | RM2927 | CCGCAGGAGGATACGGACCTGGTGCTGGACAACGATCTCAAGGACCAGG |
| 1478 | RM2928 | AGGACAAGGTCCTTATGGACCTGGCGCTGGCCAACAAGGACCTGGTTCT |
| 1479 | RM2929 | CAGGGTCCAGGTTCAGGAGGCCAACAAGGCCCAGGAGGTCAAGGACCAT |
| 1480 | RM2930 | ACGGACCATCCGCTGCGGCAGCTGCAGCTGCTGCAGGTACGTCTTCATCGCTATCCTGCA |
| 1481 | RM2931 | ACTTCCTGGACCTTGTTGACCAGCGCCTGGACCGTAACCACCTTGAGACCATCGCTAAGG |
| 1482 | RM2932 | TGTTGGCCACTACCGTAGGGTCCTTGACCGCCAGGTCCTTGTTGACCACC |
| 1483 | RM2933 | CGTAAGGTCCTTGGCCTCCCGGACCCTGCTGTCCTGCTCCACCTGGACCT |
| 1484 | RM2934 | TCCTGGACCGTAACCTCCGGCAGCGGCAGCGGCGGCAGCAGCAGCACCTGGTC |
| 1485 | RM2935 | GATCCTGGACCTTGTTGTCCAGCTCCACCTGGACCCTGTTGTCCGGC |
| 1486 | RM2936 | CCTGTTGACCAGCACCAGGACCGTATGGACCTTGTCCACCAGGACCTTGT |
| 1487 | RM2937 | GTCCTCCTGGACCCTGCTGACCACCTGAACCAGGTCCTTGACTACCTGGTC |
| 1488 | RM2938 | CTGCGGCAGCGGCTGCTGCTGCAGCGGCAGAAGGGCCGTAAGGACCCT |
| 1489 | RM2939 | TGTCCTCCTGGTCCTTGAGATCGTTGTCCAGCACCAGGTCCGTATCCTC |
| 1490 | RM2940 | ACCCTGAGAACCAGGTCCTTGTTGGCCAGCGCCAGGTCCATAAGGACCT |
| 1491 | RM2941 | GTCCGTATGGTCCTTGACCTCCTGGGCCTTGTTGGCCTCCTGAACCTGG |
| 1492 | RM2942 | GGATAGCGATGAAGACGTACCTGCAGCAGCTGCAGCTGCCGCAGCGGATG | by combining 1 µl 10×NEB T4 DNA ligase buffer, 1 µl 100 µM pooled oligos, 1 µl NEB T4 Polynucleotide Kinase (10,000 U/ml), and 7 µl ddH2O and incubating for 1 hour at 37° C. The oligos were then annealed by mixing 4 µl of the phosphorylation reaction with 16 µl of ddH2O, heating the mixture to 95° C. for 5 minutes, and then cooling the mixture to 25° C. at a rate of 0.1° C./sec. The oligos were then ligated together into a vector by combining 4 µl of the annealed oligos with 5 nmol vector backbone (RM396 [SEQ ID NO: 1405], digested with AscI and SbfI), 1 µl NEB T4 DNA ligase (400,000 U/ml), 1 µl 10×NEB T4 DNA ligase buffer, and ddH2O to 10 µl. The ligation solution was incubated for 30 minutes at room temperature. The entirety of the ligation reaction was transformed into E. coli for clonal selection, Synthesis of RM410 Sequence:
Oligos RM2999-RM3014 (SEQ ID NOs: 1492-1507) in Table 4 were combined into a single mixture at a concentration of 100 µM of each oligo. The oligos were phosphorylated in a phosphorylation reaction prepared by combining 1 µl 10×NEB T4 DNA ligase buffer, 1 µl 100 µM pooled oligos, 1 µl NEB T4 Polynucleotide Kinase (10,000 U/ml), and 7 µl ddH2O and incubating for 1 hour at 37° C. The oligos were then annealed by mixing 4 µl of the phosphorylation reaction with 16 µl of ddH2O, heating the mixture to 95° C. for 5 minutes, and then cooling the mixture to 25° C. at a rate of 0.1° C./sec. The oligos were then ligated together into a vector by combining 4 µl of the annealed oligos with 5 nmol vector backbone (RM400 [SEQ ID NO: 1406], digested with AscI and SbfI), 1 µl NEB T4 DNA ligase (400,000 U/ml), 1 µl 10×NEB T4 DNA ligase buffer, and ddH2O to 10 µl. The ligation solution was incubated for 30 minutes at room temperature. The entirety of the ligation reaction was transformed into E. coli for clonal selection, plasmid isolation, and sequence verification according to known techniques.

The resulting oligonucleotide has a 5' to 3' nucleotide sequence of SEQ ID NO: 931 and is identified as RM410.

lin (AmpR). The order (relative position) of the resistance genes matters, such that AmpR/KanR is distinct from KanR/AmpR for the purpose of DNA assembly. The 6 assembly vectors are shown in Table 5, are named based on the two resistance markers in each (C for CamR, K for KanR, and A for AmpR). The 6 assembly vectors are as follows: KC (RM396, SEQ ID NO:1402), KA (RM397, SEQ ID NO:1403), AC (RM398, SEQ ID NO:1404), AK (RM399,

TABLE 4

Oligo sequences for generating RM410 silk repeat domain (with flanking sequences for cloning) (SEQ ID NO: 931)

| SEQ ID NO: | ID | 5' to 3' Nucleotide Sequence |
|---|---|---|
| 1493 | RM2999 | CGCGCCTTAGCGATGGTCTCAAGGTGGATATGGCCCAGGAGCCGGACAACAGGGTCCT |
| 1494 | RM3000 | GGTTCACAAGGTCCAGGATCTGGTGGTCAACAGGGACCAGGCGGCCAGGGAC |
| 1495 | RM3001 | CTTATGGTCCAGGAGCCGCTGCAGCAGCAGCAGCTGTTGGAGGTTACGGCC |
| 1496 | RM3002 | CTGGTGCCGGTCAACAAGGCCCAGGATCTCAGGGTCCTGGATCTGGAGGAC |
| 1497 | RM3003 | AACAAGGTCCTGGAGGTCAGGGTCCATACGGACCTTCAGCAGCAGCTGCTGC |
| 1498 | RM3004 | TGCAGCCGCTGGTGGTTATGGACCTGGTGCTGGTCAACAAGGACCGGGTT |
| 1499 | RM3005 | CTCAGGGTCCGGGTTCAGGAGGTCAGCAGGGCCCTGGTGGACAAGGACCTT |
| 1500 | RM3006 | ATGGACCTAGTGCGGCTGCAGCAGCTGCCGCCGCAGGTACGTCTTCATCGCTATCCTGCA |
| 1501 | RM3007 | TGAACCAGGACCCTGTTGTCCGGCTCCTGGGCCATATCCACCTTGAGACCATCGCTAAGG |
| 1502 | RM3008 | CATAAGGTCCCTGGCCGCCTGGTCCCTGTTGACCACCAGATCCTGGACCTTG |
| 1503 | RM3009 | CACCAGGGCCGTAACCTCCAACAGCTGCTGCTGCTGCAGCGGCTCCTGGAC |
| 1504 | RM3010 | CTTGTTGTCCTCCAGATCCAGGACCCTGAGATCCTGGGCCTTGTTGACCGG |
| 1505 | RM3011 | GCTGCAGCAGCAGCTGCTGCTGAAGGTCCGTATGGACCCTGACCTCCAGGAC |
| 1506 | RM3012 | CCTGAGAACCCGGTCCTTGTTGACCAGCACCAGGTCCATAACCACCAGCG |
| 1507 | RM3013 | GTCCATAAGGTCCTTGTCCACCAGGGCCCTGCTGACCTCCTGAACCCGGAC |
| 1508 | RM3014 | GGATAGCGATGAAGACGTACCTGCGGCGGCAGCTGCTGCAGCCGCACTAG |

Assembly and Assay of Argiope bruennichi MaSp2, "18B"

Figure 6:
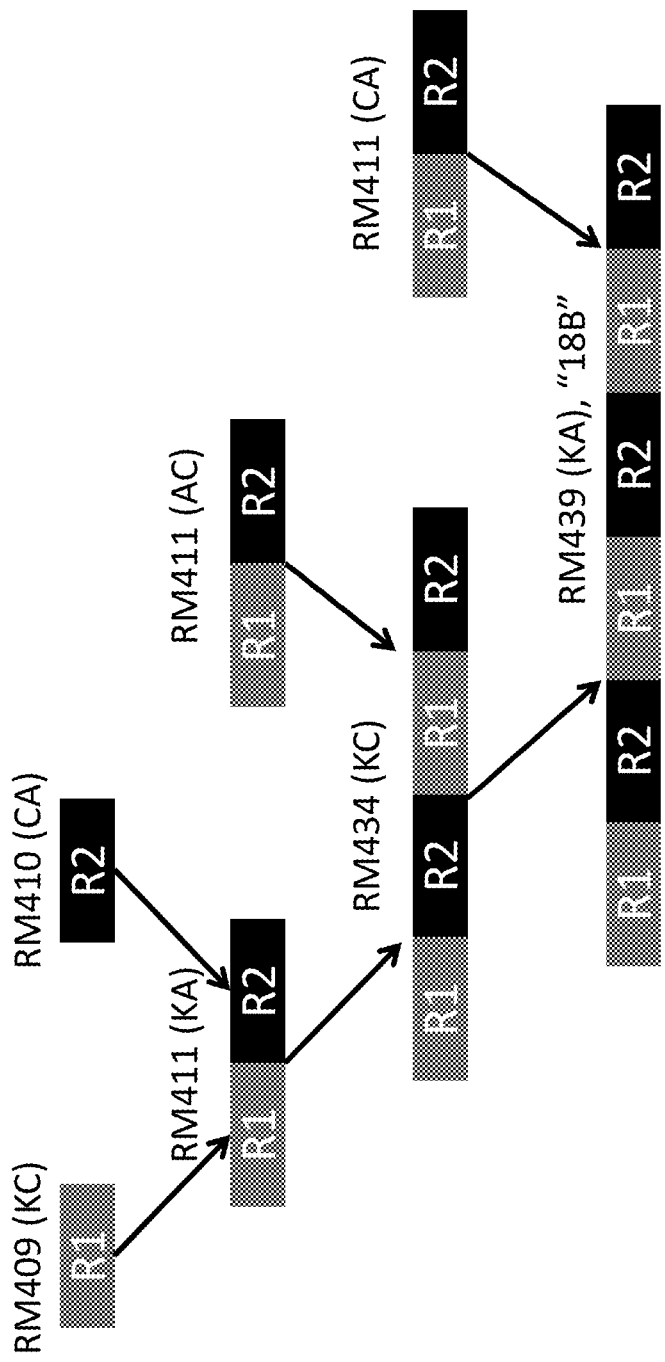
FIG. 6 depicts assembly of a block copolymer 18B silk polynucleotide from repeat sequences R1, R2, according to an embodiment of the invention.

RM409 (SEQ ID NO: 930) and RM410 (SEQ ID NO: 931) oligonucleotide sequences synthesized according to the method described above were assembled according to the diagram shown in FIG. 6 to generate RM439 silk nucleotide sequence (e.g., "18B").

Figure 7:
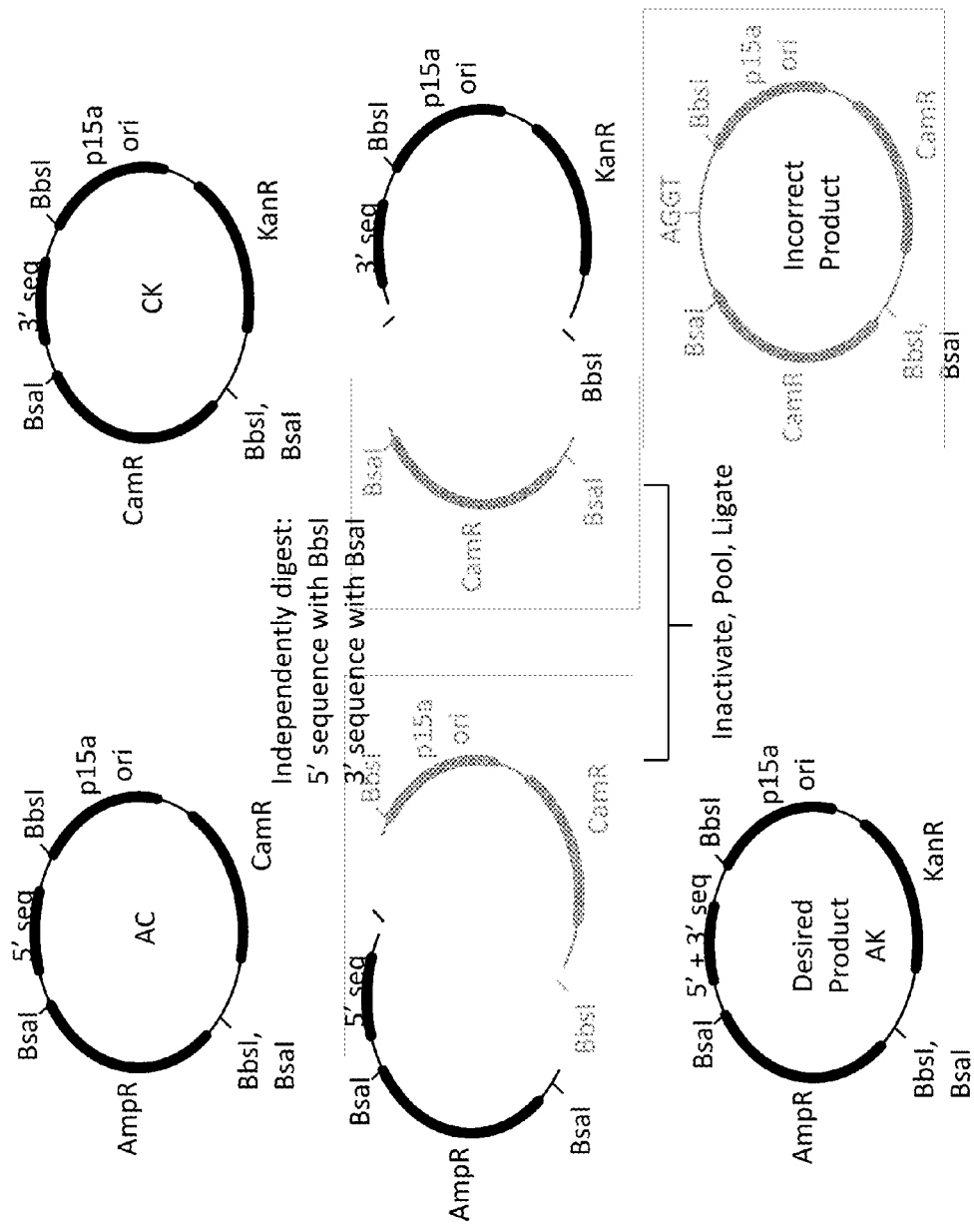
FIG. 7 depicts assembly vectors used to assemble silk polynucleotide segments, according to an embodiment of the invention.
Figure 8:
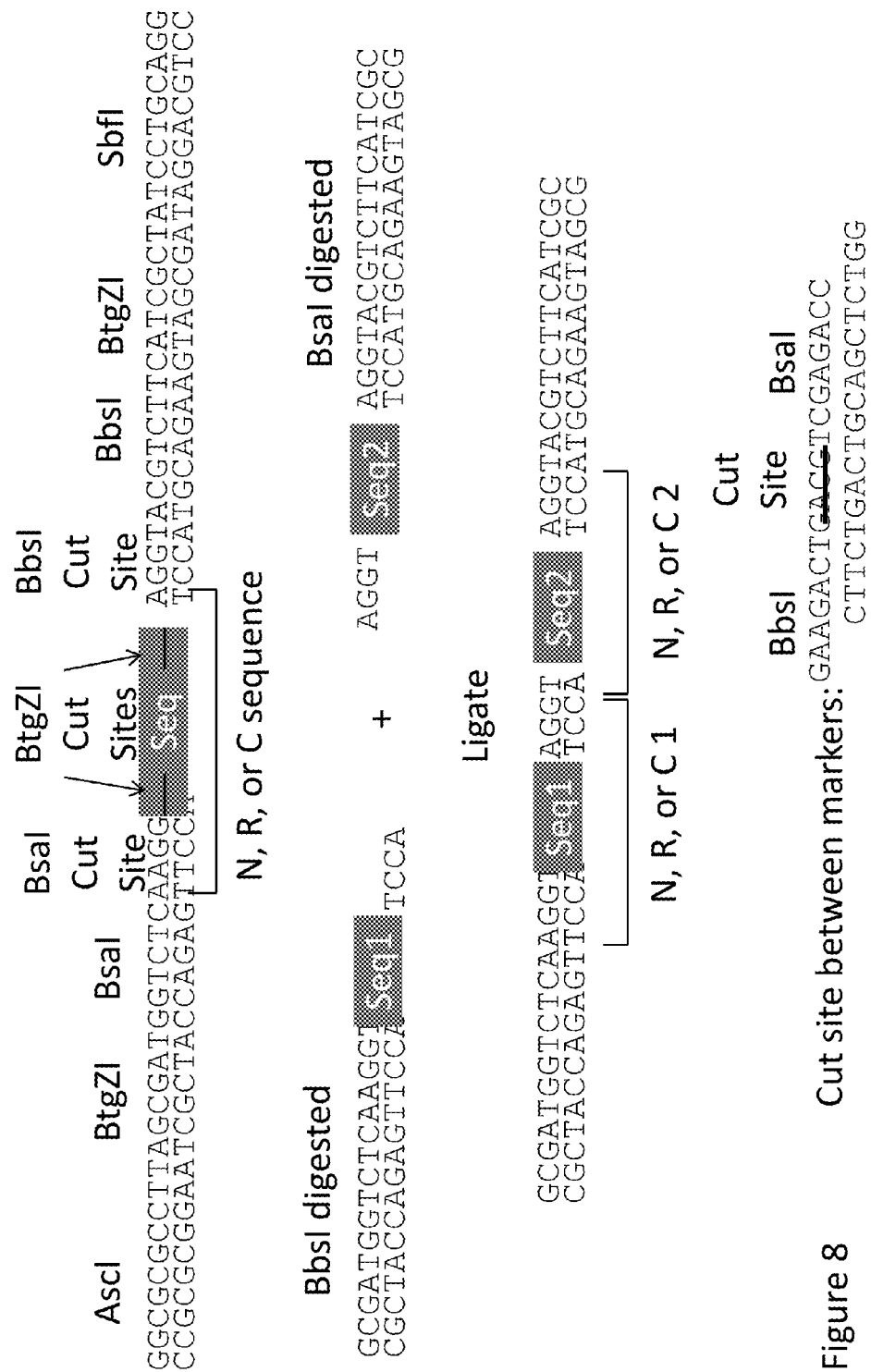
FIG. 8 shows ligation of 2 sequences to form a part of a silk polynucleotide sequence, according to an embodiment of the invention.

RM409 (SEQ ID NO: 930) and RM410 (SEQ ID NO: 931) in assembly vectors were digested and ligated according to the diagrams shown in FIG. 7 and FIG. 8. Silk N, R, and C domains, as well as additional elements including the alpha mating factor pre-pro sequence and a 3× FLAG tag, were assembled using a pseudo-scarless 2 antibiotic (2ab) method (Leguia, M., et al., 2ab assembly: a methodology for automatable, high-throughput assembly of standard biological parts, J. Biol. Eng., 7:1 (2013); and Kodumal, S. J., et al., Total synthesis of long DNA sequences: synthesis of a contiguous 32-kb polyketide synthase gene cluster, Proc. Natl. Acad. Sci. U.S.A., 101:44, pg. 15573-15578 (2004)).

2ab assembly relies on the use of 6 assembly vectors that are identical except for the identity and relative position of 2 selectable markers. Each vector is resistant to exactly 2 of: chloramphenicol (CamR), kanamycin (KanR), and ampicil- SEQ ID NO:1405), CA (RM400, SEQ ID NO:1406), and CK (RM401, SEQ ID NO:1407). Assembly vectors are shown in Table 5. Sequences for the vectors include those of SEQ ID NOs: 1399-1410.

TABLE 5

Expression and assembly vectors

| Vector ID | Vector Type | Description | SEQ ID NO: |
|---|---|---|---|
| RM618 | Expression Vector (dummy insert) | circular, double stranded DNA | 1399 |
| RM652 | Expression Vector (dummy insert) | circular, double stranded DNA | 1400 |
| RM468 | Expression Vector (dummy insert) | circular, double stranded DNA | 1401 |
| RM396 | Assembly Vector (dummy insert) | circular, double stranded DNA | 1402 |
| RM397 | Assembly Vector (dummy insert) | circular, double stranded DNA | 1403 |
| RM398 | Assembly Vector (dummy insert) | circular, double stranded DNA | 1404 |
| RM399 | Assembly Vector (dummy insert) | circular, double stranded DNA | 1405 |
| RM400 | Assembly Vector (dummy insert) | circular, double stranded DNA | 1406 |

TABLE 5-continued

Expression and assembly vectors

| Vector ID | Vector Type | Description | SEQ ID NO: |
|---|---|---|---|
| RM401 | Assembly Vector (dummy insert) | circular, double stranded DNA | 1407 |
| RM529 | Assembly Vector, alpha mating factor special case | circular, double stranded DNA | 1408 |

FIG. 7 shows a single assembly reaction performed with two compatible vectors, AC (RM398 SEQ ID NO:1404) and CK (RM401 SEQ ID NO:1407), one containing a sequence destined for the 5' end of the target composite sequence and one destined for the 3' end of the target composite sequence. The plasmid bearing the 5' sequence is independently digested with BbsI, while the plasmid bearing the 3' sequence is independently digested with BsaI.

After inactivation of the enzymes, the two digested plasmids are pooled and ligated. The desired product resides in an AK vector, which is distinct from all input vectors and undesired byproducts. This enables selection for the desired product after transformation into E. coli.

The DNA sequence of the cloning sites during this process is shown in FIG. 8. By selecting the 4 bp overhang generated by the type IIs enzymes to be AGGT, assembly of DNA fragments generates scarless junctions in the desired encoded polypeptide provided that the polypeptide starts with a glycine (coded by GGT) and terminates with a codon ending in an A (all except F, Y, W, C, H, N, M, and D).

The assembly of RM409 (SEQ ID NO: 930) and RM410 (SEQ ID NO: 931) in KC and CA assembly vectors, respectively, generated RM411 (SEQ ID NO: 465) in KA, as shown in FIG. 6. The RM411 (SEQ ID NO: 465) sequence was transferred to AC and CA using AscI and SbfI. The RM411 (SEQ ID NO: 465) KA and AC sequences were digested and ligated according to the procedure described above to generate RM434 (SEQ ID NO: 466) in KC. Finally, RM434 (SEQ ID NO: 466) in KC was digested and ligated with RM411 (SEQ ID NO: 465) in CA to generate the final silk polypeptide coding sequence, RM439 (SEQ ID NO: 467) (aka, "18B").

Transfer of "18B" Silk Polypeptide Coding Sequence (RM439) to the RM468 Expression Vector:

The RM468 (SEQ ID NO: 1401) expression vector contains an alpha mating factor sequence and a 3× FLAG sequence (SEQ ID NO: 1409). The 18B silk polypeptide coding sequence RM439 (SEQ ID NO: 467) was transferred to the RM468 (SEQ ID NO: 1401) expression vector via BtgZI restriction enzymes and Gibson reaction kits. The RM439 vector was digested with BtgZI, and the polynucleotide fragment containing the silk sequence isolated by gel electrophoresis. The expression vector, RM468, exclusive of an unwanted dummy insert, was amplified by PCR using primers RM3329 and RM3330, using the conditions described in Example 4. The resulting PCR product and isolated silk fragment were combined using a Gibson reaction kit according to the manufacturers instructions. Gibson reaction kits are commercially available (https://www.neb.com/products/e2611-gibson-assembly-master-mix), and are described in a U.S. Pat. No. 5,436,149 and in Gibson, D. G. et al., Enzymatic assembly of DNA molecules up to several hundred kilobases, Nat. Methods, 6:5, pg. 343-345 (2009).

The resulting expression vector containing RM439 (SEQ ID NO: 467) was transformed into Pichia (Komagataella) pastoris. Clones of the resulting cells were cultured according to the following conditions: The culture was grown in a minimal basal salt media, similar to one described in [http://tools.invitrogen.com/content/sfs/manuals/pichiaferm_prot.pdf] with 50 g/L of glycerol as a starting feedstock. Growth was in a stirred fermentation vessel controlled at 30 C, with 1 VVM of air flow and 2000 rpm agitation. pH was controlled at 3 with the on-demand addition of ammonium hydroxide. Additional glycerol was added as needed based on sudden increases in dissolved oxygen. Growth was allowed to continue until dissolved oxygen reached 15% of maximum at which time the culture was harvested, typically at 200-300 OD of cell density.

Figure 9:
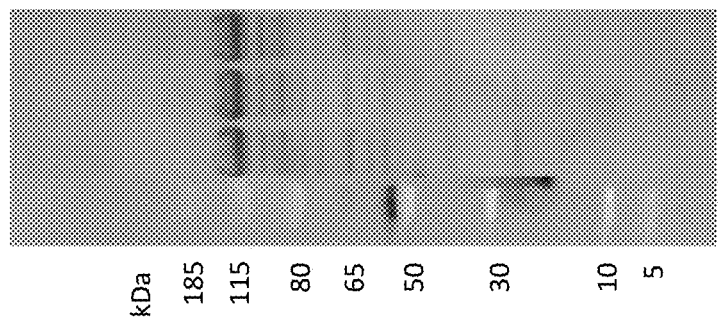
FIG. 9 is a western blot comprising block copolymer silk polypeptides isolated from a culture expressing an 18B silk polypeptide.

The broth from the fermenter was decellularized by centrifugation. The supernatant from the Pichia (Komagataella) pastoris culture was collected. Low molecular weight components were removed from the supernatant using ultrafiltration to remove particles smaller than the block copolymer polypeptides. The filtered culture supernatant was then concentrated up to 50×. The polypeptides in the supernatant were precipitated and analyzed via a western blot. The product is shown in the western blot in FIG. 9. The predicted molecular weight of processed 18B is 82 kDa. The product observed in the western blot in FIG. 9 exhibited a higher MW of ~120 kDa. While the source of this discrepancy is unknown, other silk polypeptides have been observed to appear at a higher than expected molecular weight.

Figure 10:
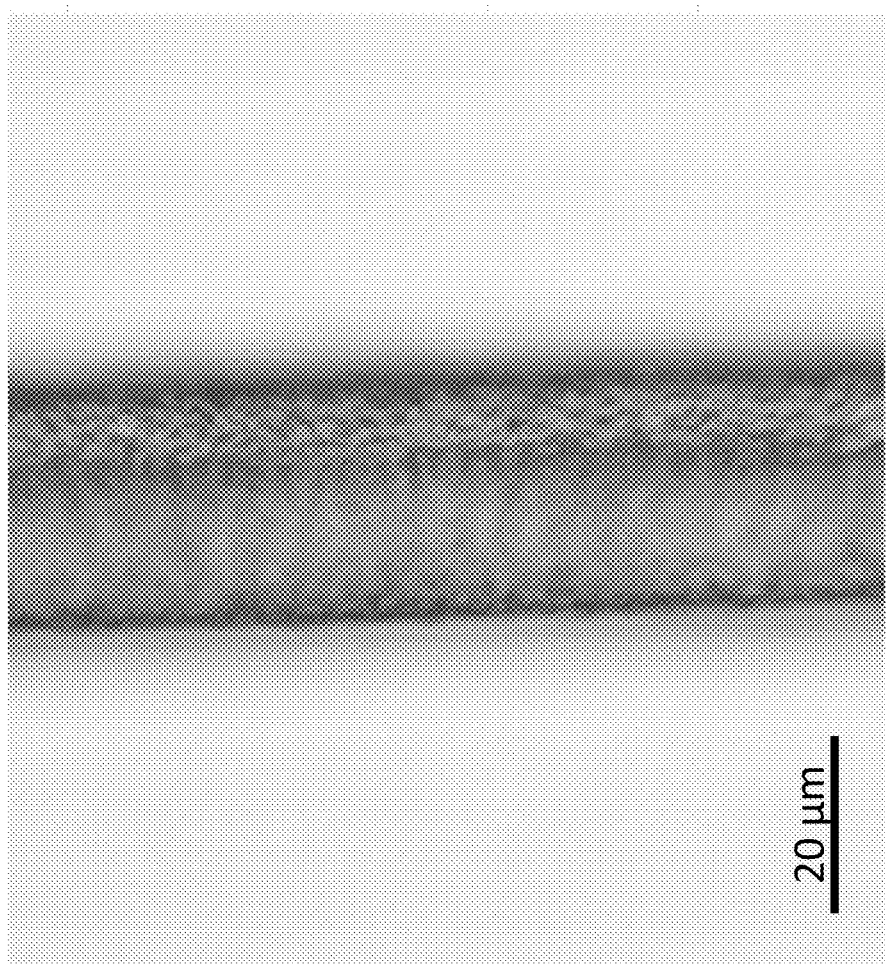
FIG. 10 is a light microscopy magnified view of a block copolymer fiber produced by methods described herein.

The 18B block copolymer polypeptide was purified and processed into a fiber spinnable solution. The fiber spinnable solution was prepared by dissolving the purified and dried polypeptide in a spinning solvent. The polypeptide is dissolved in the selected solvent at 20 to 30% by weight. The fiber spinnable solution was then extruded through a 150 micron diameter orifice into a coagulation bath comprising 90% methanol/10% water by volume. Fibers were removed from the coagulation and drawn from 1 to 5 times their length, and subsequently allowed to dry. The resulting fiber is shown in FIG. 10.

Figure 11:
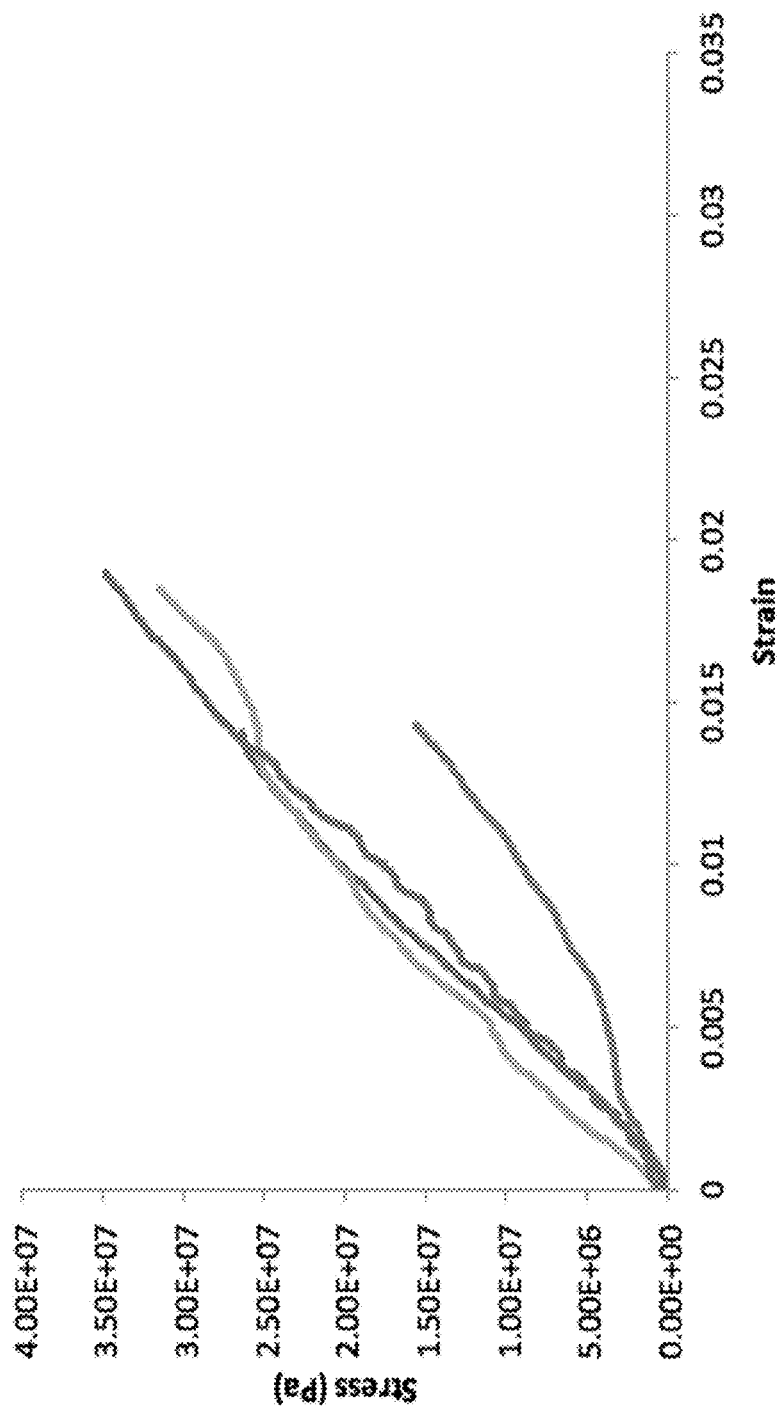
FIG. 11 shows a graph of stress v. strain for several block copolymer fibers produced according to methods described herein.

Mechanical testing was performed on the 18B block copolymer polypeptide that was secreted, purified, dissolved, and turned into a fiber as described above. Fibers were tested for mechanical properties on a custom-built tensile tester, using common processes. Test samples were mounted with a gauge length of 5.75 mm and tested at a strain rate of 1%. The resultant forces were normalized to the fiber diameter, as measured by microscopy. Results of stress vs strain are shown in FIG. 11 in which each stress-strain curve represents a replicate measurement from a fiber from a single spinning experiment, from a single batch.

Example 6

Assembly and Assay of 4× Repeat R Sequences

Figure 12:
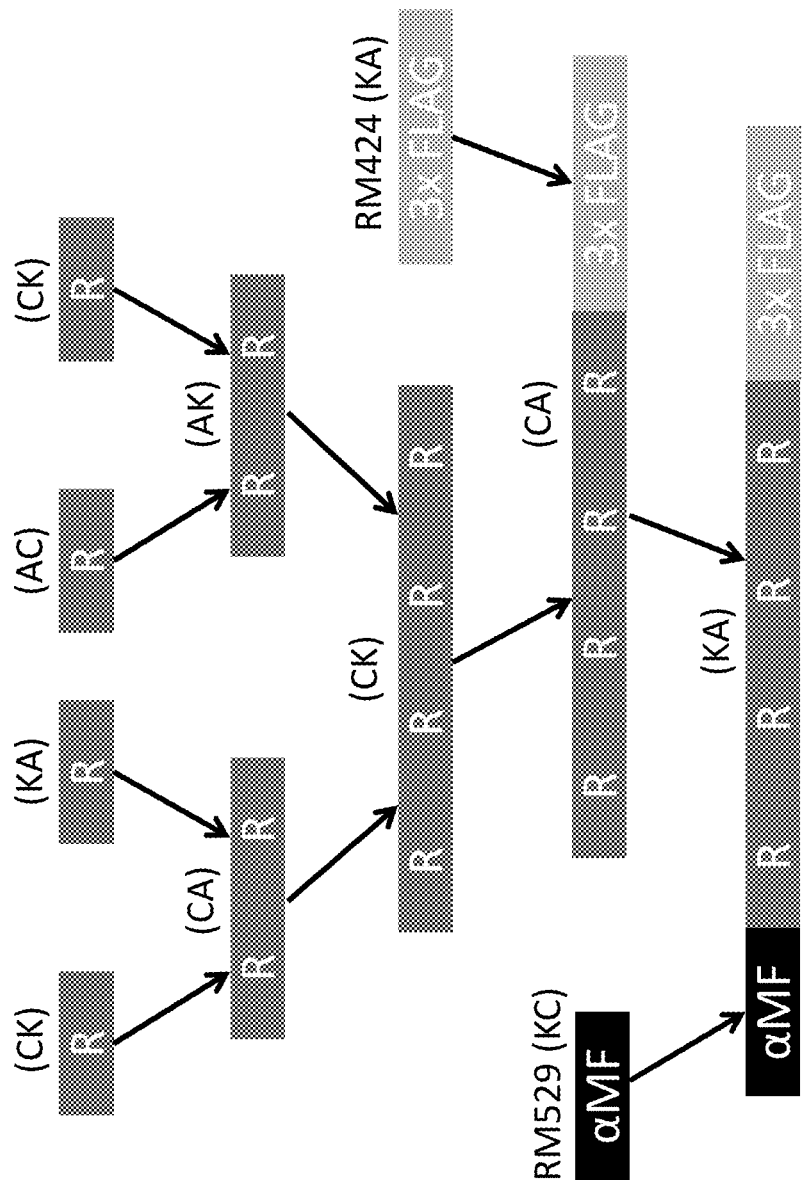
FIG. 12 is an assembly diagram of several silk R domains to form a block copolymer polynucleotide, according to an embodiment of the invention.
Figure 13:
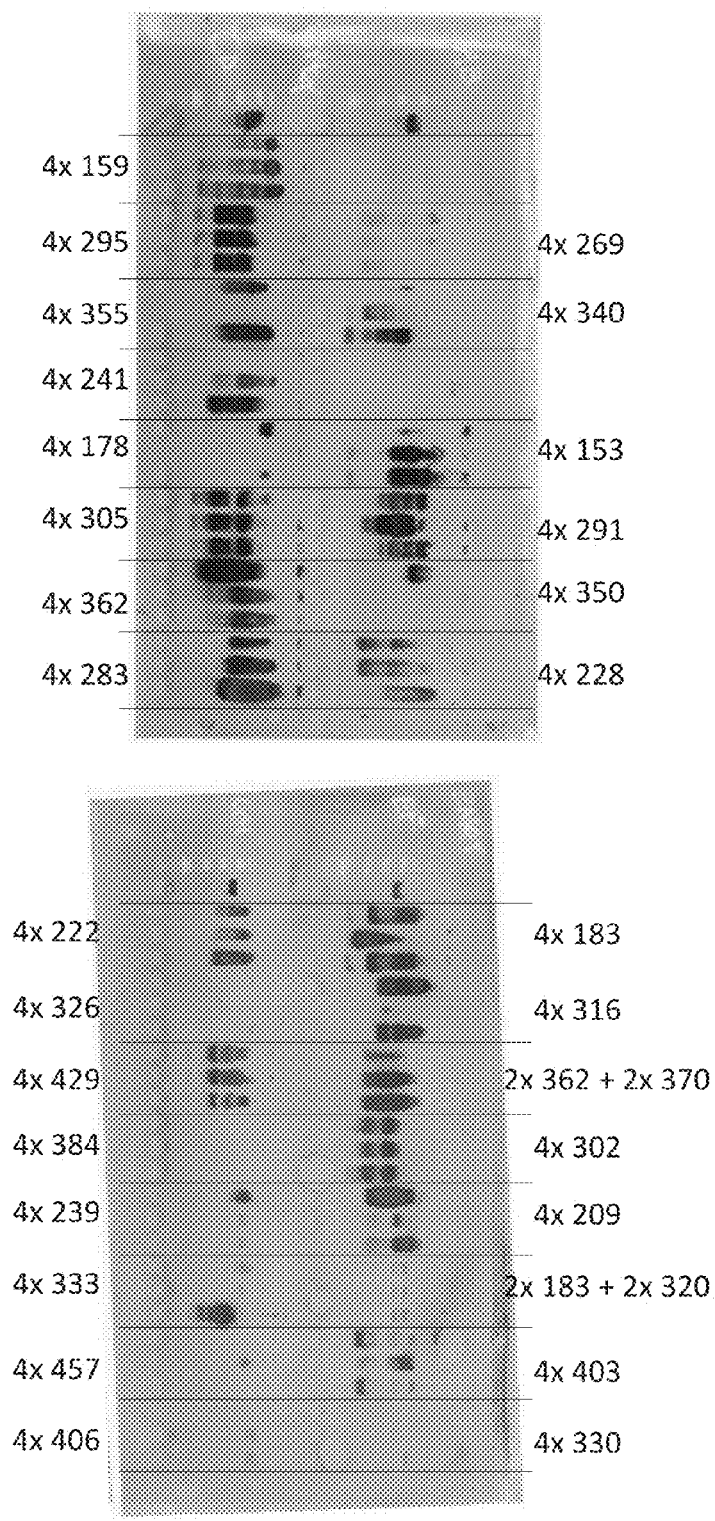
FIG. 13 shows a western blot of expressed block copolymer polypeptides each polypeptide being a concatemer of four copies of the indicated silk repeat sequences.

Selected R domains from SEQ ID NOs: 1-1398 that expressed and secreted well were concatenated into 4× repeat domains using the assembly scheme shown in FIG. 12. The concatenation was performed as described in Example 4 and shown in FIGS. 7 and 8. Selected sequences from this ligation of R sequences are shown in Table 6. Sequences for these silk constructs include those full-length silk construct sequences of SEQ ID NOs: 1411-1468. The resulting products comprising 4 repeat sequences, an alpha mating factor, and a 3× FLAG domain were digested with AscI and SbfI to release the desired silk sequence and ligated into expression vector RM652 (SEQ ID NO: 1400) that had been digested with AscI and SbfI to release an unwanted dummy insert. After clonal isolation from E. coli, vectors were then transformed into Pichia pastoris. Transformants were plated on YPD agar plates containing 25 μg/ml nourseothricin and incubated for 48 hours at 30° C. Three clones from each transformation were inoculated into 400 μl of BMGY in a 96-well square-well block, and incubated for 48 hours at 30° C. with agitation at 1000 rpm. Cells were pelleted via centrifugation, and the supernatant was recovered for analysis of block copolymer polypeptide content via western blot (FIG. 13). Of the 28 constructs transformed with 4× identical repeat sequences, most (18/28) had at least one clone with a substantial signal on the western blot, and only 1 showed no signal at all. Of two constructs composed of 2 repeats each of 2 distinct repeat sequences, one showed a strong western blot signal, while the other showed a modest western signal. This confirms that assembling larger block copolymer-expressing polynucleotides from smaller, well-expressed polynucleotides generally leads to functionally expressed block copolymer polypeptides. Streakiness, multiple bands, and clone-to-clone variation are evident on the western. While the specific source of these variations has not been identified, they are generally consistent with typically observed phenomena, including polypeptide degradation, post-translational modification (e.g., glycosylation), and clonal variation following genomic integration. Modified and degraded polypeptide products can be incorporated into fibers without adversely affecting the utility of the fibers depending on their intended use.

TABLE 6

Full length block copolymer silk constructs with alpha mating factor, 4X repeat domains, and 3X FLAG domains.

| Construct ID | R/N/C | Amino acid SEQ ID NO | Nucleotide SEQ ID NO: | Western Results (1 = no band 2 = weak band 3 = strong band) |
|---|---|---|---|---|
| 4x 269 | R | 1411 | 1440 | 2 |
| 4x 340 | R | 1412 | 1441 | 3 |
| 4x 153 | R | 1413 | 1442 | 3 |
| 4x 291 | R | 1414 | 1443 | 3 |
| 4x 350 | R | 1415 | 1444 | 3 |
| 4x 228 | R | 1416 | 1445 | 2 |
| 4x 159 | R | 1417 | 1446 | 3 |
| 4x 295 | R | 1418 | 1447 | 3 |
| 4x 355 | R | 1419 | 1448 | 3 |
| 4x 241 | R | 1420 | 1449 | 3 |
| 4x 178 | R | 1421 | 1450 | 3 |
| 4x 305 | R | 1422 | 1451 | 3 |
| 4x 362 | R | 1423 | 1452 | 2 |
| 4x 283 | R | 1424 | 1453 | 3 |
| 4x 183 | R | 1425 | 1454 | 3 |
| 4x 316 | R | 1426 | 1455 | 3 |
| 2x 362 + 2x 370 | R | 1509 | 2802 | 3 |
| 4x 302 | R | 1427 | 1456 | 3 |
| 4x 209 | R | 1428 | 1457 | 3 |
| 2x 183 + 2x 320 | R | 1511 | 1510 | 2 |
| 4x 403 | R | 1430 | 1459 | 3 |
| 4x 330 | R | 1431 | 1460 | 2 |
| 4x 222 | R | 1432 | 1461 | 3 |
| 4x 326 | R | 1433 | 1462 | 2 |
| 4x 429 | R | 1434 | 1463 | 3 |
| 4x 384 | R | 1435 | 1464 | 1 |
| 4x 239 | R | 1436 | 1465 | 2 |
| 4x 333 | R | 1437 | 1466 | 3 |
| 4x 457 | R | 1438 | 1467 | 2 |
| 4x 406 | R | 1439 | 1468 | 2 |

Example 7

Expression of 18B from *Bacillus subtilis*

An *E. coli/B. subtilis* shuttle and expression plasmid is first constructed. The polynucleotide encoding 18B is transferred, using a Gibson reaction, to plasmid pBE-S (Takara Bio Inc.). Plasmid pBE-S (SEQ ID NO: 1512) is amplified using primers BES-F (5'-AAGACGATGACGATAAGGAC-TATAAAGATGATGACGACAAATAATGCGGTAGTT TATCAC-3') (SEQ ID NO: 2831) and BES-R (5'-CCA-GCGCCTGGACCGTAACCCGGCCGCAGCCTGCGCA-GACATGTTGCTGAACGC CATCGT-3') (SEQ ID NO: 2832) in a PCR reaction. The reaction mixture consists of 1 μl of 10 μM BES-F, 1 μl of 10 μM BES-R, 0.5 μg of pBE-S DNA (in 1 μl volume), 22 μl of deionized H2O, and 25 μl of Phusion High-Fidelity PCR Master Mix (NEB catalog M0531S). The mixture is thermocycled according to the following program:
1) Denature for 5 minutes at 95° C.
2) Denature for 30 seconds at 95° C.
3) Anneal for 30 seconds at 55° C.
4) Extend for 6 minutes at 72° C.
5) Repeat steps 2-4 for 29 additional cycles
6) Perform a final extension for 5 minutes at 72° C.

The product is subjected to gel electrophoresis, and the product of approximately 6000 bp is isolated, then extracted using a Zymoclean Gel DNA Recovery Kit (Zymo Research) according to the manufacturer's instructions. The polynucleotide encoding 18B is isolated by digestion of 18B in the KA assembly vector using restriction enzyme BtgZI, followed by gel electrophoresis, fragment isolation, and gel extraction. The pBE-S and 18B fragments are joined together using Gibson Assembly Master Mix (New England Biolabs) according to the manufacturer's instructions, and the resulting plasmid transformed into *E. coli* using standard techniques for subsequent clonal isolation, DNA amplification, and DNA purification. The resulting plasmid, pBE-S-18B (SEQ ID NO: 1513), is then diversified by insertion of various signal peptides (the "SP DNA mixture") according to the manufacturer's instructions. A mixture of pBE-S-18B plasmids containing different secretion signal peptides is then transformed into *B. subtilis* strain RIK1285 according to the manufacturer's instructions. 96 of the resulting colonies are incubated in TY medium (10 g/L tryptone, 5 g/L yeast extract, 5 g/L NaCl) for 48 hours, at which point the cells are pelleted and the supernatant is analyzed by western blot for expression of the 18B polypeptide.

Example 8

Expression of 18B from *Chlamydomonas reinhardtii*

An *E. coli* vector bearing an excisable *C. reinhardtii* expression cassette, pChlamy (SEQ ID NO: 1514), is first constructed using commercial DNA synthesis and standard techniques. The cassette is described in detail in Rasala, B. A., Robust expression and secretion of Xylanase1 in *Chlamydomonas reinhardtii* by fusion to a selection gene and processing with the FMDV 2A peptide, *PLoS One*, 7:8 (2012). The polypeptide encoding 18B, a 3× FLAG tag, and a stop codon is reverse translated using the codon preference of *C. reinhardtii* (available, for example, at http://www.kazusa.or.jp/codon/cgi-bin/showcodon.cgi?species=3055) and synthesized using commercial synthesis. During synthesis, flanking BbsI sites are included to allow release of the 18B-3× FLAG polynucleotide. The polynucleotide resulting from PCR amplification of the pChlamy plasmid using primers designed to generate a linear fragment including the entire plasmid sequence except 5'-ATGTTTTAA-3' and also including 40 bp of homology to the 18B-3× FLAG coding sequence on each end is joined with the 18B-3× FLAG polynucleotide liberated by digestion with BbsI using a Gibson reaction, and transformed into *E. coli* for clonal selection, DNA amplification, and plasmid isolation. The resulting plasmid is digested with BsaI to release the 18B expression cassette, which is isolated by gel purification. The digested fragment is electroporated into strain cc3395, which is then selected on 15 μg/ml zeocin. Several clones are grown up in liquid culture, the cells pelleted by centrifugation, and the supernatant analyzed by western blot for protein expression.

Example 9

Additional Silk and Silk-Like Sequences

Additional silk and silk-like sequences and partial sequences were obtained from NCBI's sequence database by search for the term "silk" while excluding "spidroin" "*bombyx*" and "*latrodectus*". A subset of the resulting nucleotide sequences were translated into amino acid sequences, then curated to remove repeated sequences. Short sequences, generally less than 200-500 amino acids long, were removed. Further, primary sequences for select polypeptides known to form structural elements were obtained from public databases. Amino acid sequences so obtained, in addition to the sequences described in Example 1, were used to search for additional silk and silk-like sequences by homology. Resulting silk and silk-like sequences were curated, then partitioned into repetitive and non-repetitive regions.

Repetitive polypeptide sequences (repeat (R) sequences) were selected from each silk sequence and include SEQ ID NOs: 2157-2690 (SEQ ID NOs: 2157-2334 are nucleotide sequences, SEQ ID NOs: 2335-2512 are nucleotide sequences with flanking sequences for cloning, and SEQ ID NOs: 2513-2690 are amino acid sequences). Some of the R sequences have been altered, e.g., by addition of a serine to the C terminus to avoid terminating the sequence with an F, Y, W, C, H, N, M, or D amino acid. This allows for incorporation into the vector system described above. Incomplete blocks may also have been altered by incorporation of segments from a homologous sequence from another block.

Non-repetitive N terminal domain sequences (N sequences) and C terminal domain sequences (C sequences) were also selected from some silk and silk-like sequences (SEQ ID NOs: 2157-2690). The N terminal domain sequences were altered by removal of the leading signal sequence and, if not already present, addition of an N-terminal glycine residue. In some cases, the N and/or C domains were not separated from the R sequence(s) before further processing. R, N, and C amino acid sequences were reverse translated to nucleotide sequences as described in Example 2. The resulting nucleotide sequences were flanked with the following sequences during synthesis to enable cloning:

5'-GAAGACTTAA-SILK-GGTACGTCTTC-3' (SEQ ID NOS 2833 and 2826) where "SILK" is a polynucleotide sequence selected according to the teachings above.

Resulting linear DNA was digested with BbsI and ligated into vector RM747 (SEQ ID NO: 2696) which had been digested with BsmBI to release a dummy insert. Ligated material was transformed into *E. coli* for clonal isolation, DNA amplification, and sequence verification using standard methods. Resulting plasmids were digested with BsaI and BbsI, and the fragment encoding a silk or silk-like polypeptide isolated by gel electrophoresis, fragment excision, and gel extraction. The fragment was subsequently ligated into Expression Vector RM1007 (SEQ ID NO: 2707) which had been digested with BsmBI and treated with Calf Intestinal Alkaline Phosphatase. Ligated material was transformed into *E. coli* for clonal isolation, DNA amplification, and sequence verification using standard methods.

Expression vectors containing R, N, and/or C sequences were transformed into *Pichia* (*Komagataella*) *pastoris* (strain RMs71, described in Example 3) using the PEG method (Cregg, J. M. et al., DNA-mediated transformation, *Methods Mol. Biol.*, 389, pg. 27-42 (2007)). The expression vector consisted of a targeting region and promoter (pGAP), a dominant resistance marker (nat-conferring resistance to nourseothricin), a secretion signal (alpha mating factor leader and pro sequence), a C-terminal 3× FLAG epitope, and a terminator (pAOX1 pA signal).

Transformants were plated on Yeast Extract Peptone Dextrose Medium (YPD) agar plates containing 25 μg/ml nourseothricin and incubated for 48 hours at 30° C. Two clones from each transformation were inoculated into 400 μl of Buffered Glycerol-complex Medium (BMGY) in a 96-well square-well block, and incubated for 48 hours at 30° C. with agitation at 1000 rpm. Cells were pelleted via centrifugation, and the supernatant was recovered for analysis of block copolymer polypeptide content via western blot analysis of the 3× FLAG epitope.

Figure 14:
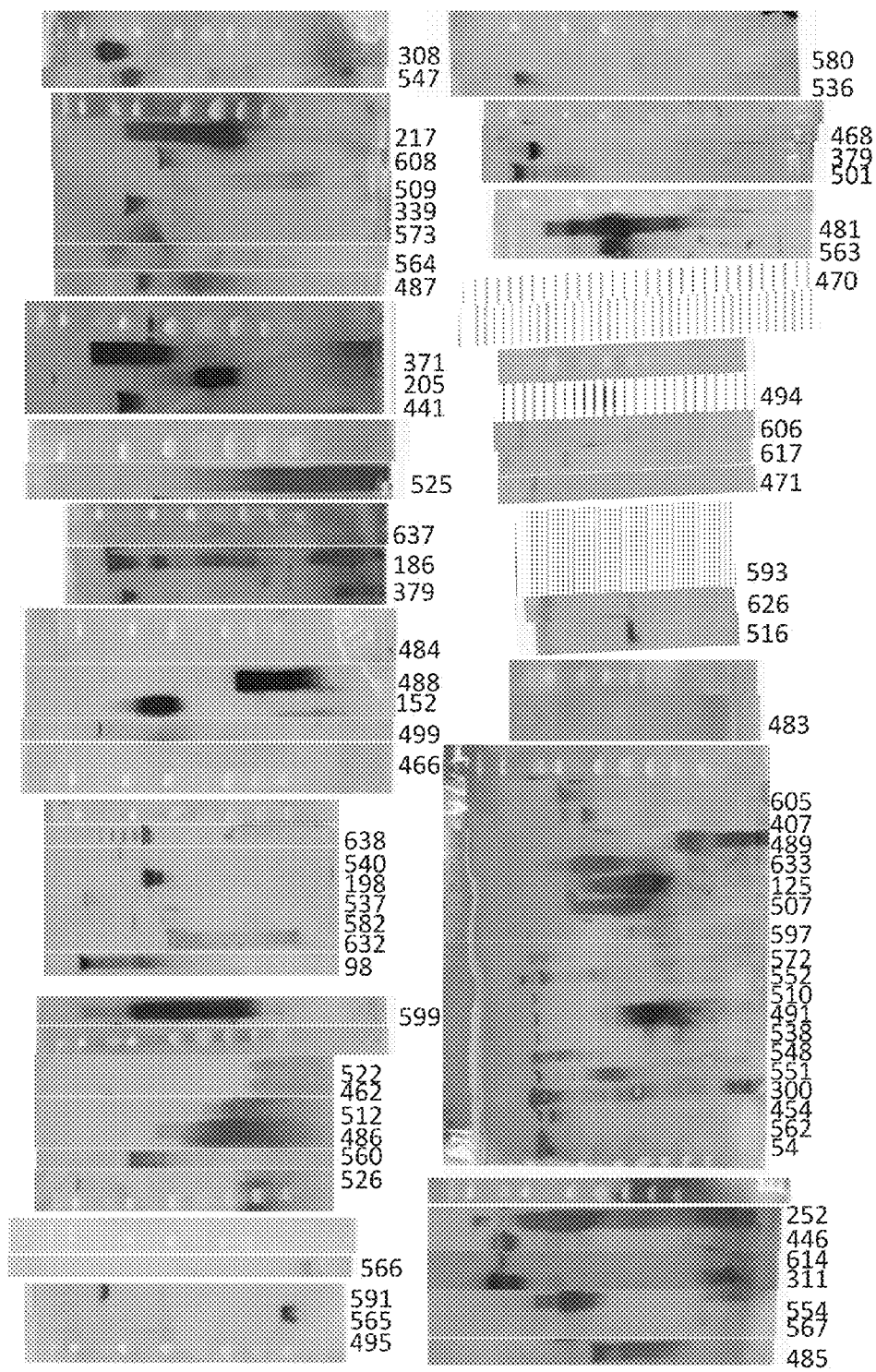
FIG. 14 shows representative western blots of additional expressed block copolymer polypeptides built using silk repeat sequences and expressed silk terminal domain sequences.

Successful polypeptide expression and secretion was judged by western blot. Each western lane was scored as 1: No band 2: Moderate band or 3: Intense band. The higher of the two scores for each clone was recorded. Representative western blot data are shown in FIG. 14. A complete listing of all R, N, and C sequences tested along with western blot results is shown in Table 7. Silk and silk-like block copolymer polypeptides from numerous species expressed successfully, encompassing diverse species and diverse polypeptide structures.

A number of embodiments of the invention have been described. Nevertheless, it will be understood that various modifications may be made without departing from the spirit and scope of the invention.

TABLE 7

Additional silk polypeptide sequences

| Construct # | Species | N/C/R sequence | Nucleotide SEQ ID NO | Nucleotide with flanking sequences SEQ ID NO: | Amino Acid SEQ ID NO: | Western Results (1 = no band 2 = weak band 3 = strong band) |
|---|---|---|---|---|---|---|
| 463 | Ceratitis capitata | R | 2157 | 2335 | 2513 | no data |
| 464 | Archimantis monstrosa | NRC | 2158 | 2336 | 2514 | no data |
| 465 | Archimantis monstrosa | NRC | 2159 | 2337 | 2515 | no data |
| 466 | Pseudomantis albofimbriata | NRC | 2160 | 2338 | 2516 | 1 |
| 467 | Pseudomantis albofimbriata | NRC | 2161 | 2339 | 2517 | no data |
| 468 | Tenodera australasiae | NRC | 2162 | 2340 | 2518 | 2 |

TABLE 7-continued

Additional silk polypeptide sequences

| Construct # | Species | N/C/R sequence | Nucleotide SEQ ID NO | Nucleotide with flanking sequences SEQ ID NO: | Amino Acid SEQ ID NO: | Western Results (1 = no band 2 = weak band 3 = strong band) |
|---|---|---|---|---|---|---|
| 469 | Tenodera australasiae | NRC | 2163 | 2341 | 2519 | no data |
| 470 | Hydropsyche angustipennis | R | 2164 | 2342 | 2520 | 1 |
| 471 | Hydropsyche angustipennis | R | 2165 | 2343 | 2521 | no data |
| 472 | Hydropsyche angustipennis | N | 2166 | 2344 | 2522 | no data |
| 473 | Hydropsyche angustipennis | C | 2167 | 2345 | 2523 | no data |
| 474 | Hydropsyche sp. T20 | R | 2168 | 2346 | 2524 | no data |
| 475 | Rhyacophila obliterata | R | 2169 | 2347 | 2525 | no data |
| 476 | Rhyacophila obliterata | R | 2170 | 2348 | 2526 | no data |
| 477 | Rhyacophila obliterata | C | 2171 | 2349 | 2527 | no data |
| 478 | Rhyacophila obliterata | N | 2172 | 2350 | 2528 | no data |
| 479 | Limnephilus decipiens | R | 2173 | 2351 | 2529 | no data |
| 480 | Chironomus pallidivittatus | NRC | 2174 | 2352 | 2530 | no data |
| 481 | Chironomus pallidivittatus | R | 2175 | 2353 | 2531 | 3 |
| 482 | Chironomus pallidivittatus | R | 2176 | 2354 | 2532 | no data |
| 483 | Chironomus thummi | R | 2177 | 2355 | 2533 | 3 |
| 484 | Stenopsyche marmorata | R | 2178 | 2356 | 2534 | 1 |
| 485 | Mallada signata | R | 2179 | 2357 | 2535 | 3 |
| 486 | Mallada signata | N | 2180 | 2358 | 2536 | 3 |
| 487 | Mallada signata | C | 2181 | 2359 | 2537 | 3 |
| 488 | Mallada signata | R | 2182 | 2360 | 2538 | 3 |
| 489 | Mallada signata | R | 2183 | 2361 | 2539 | 3 |
| 490 | Mallada signata | N | 2184 | 2362 | 2540 | no data |
| 491 | Mallada signata | C | 2185 | 2363 | 2541 | 3 |
| 492 | Mallada signata | R | 2186 | 2364 | 2542 | no data |
| 493 | Haploembia solieri | R | 2187 | 2365 | 2543 | no data |
| 494 | Culex quinquefasciatus | R | 2188 | 2366 | 2544 | no data |
| 495 | Culex quinquefasciatus | R | 2189 | 2367 | 2545 | 1 |
| 496 | Oecophylla smaragdina | NRC | 2190 | 2368 | 2546 | no data |
| 497 | Oecophylla smaragdina | NRC | 2191 | 2369 | 2547 | no data |
| 498 | Oecophylla smaragdina | NRC | 2192 | 2370 | 2548 | no data |
| 499 | Oecophylla smaragdina | NRC | 2193 | 2371 | 2549 | 2 |
| 500 | Myrmecia forficata | NRC | 2194 | 2372 | 2550 | no data |
| 501 | Myrmecia forficata | NRC | 2195 | 2373 | 2551 | 2 |
| 502 | Myrmecia forficata | NRC | 2196 | 2374 | 2552 | no data |
| 503 | Myrmecia forficata | NRC | 2197 | 2375 | 2553 | no data |
| 504 | Bombus terrestris | NRC | 2198 | 2376 | 2554 | no data |
| 505 | Bombus terrestris | NRC | 2199 | 2377 | 2555 | no data |
| 506 | Bombus terrestris | NRC | 2200 | 2378 | 2556 | no data |
| 507 | Bombus terrestris | NRC | 2201 | 2379 | 2557 | 3 |
| 508 | Bombus terrestris | NRC | 2202 | 2380 | 2558 | no data |
| 509 | Vespa simillima xanthoptera | R | 2203 | 2381 | 2559 | 3 |
| 510 | Vespa simillima xanthoptera | R | 2204 | 2382 | 2560 | 2 |
| 511 | Vespa simillima xanthoptera | R | 2205 | 2383 | 2561 | no data |
| 512 | Vespa simillima xanthoptera | NRC | 2206 | 2384 | 2562 | 3 |
| 513 | Vespa simillima xanthoptera | NRC | 2207 | 2385 | 2563 | no data |
| 514 | Vespa simillima xanthoptera | NRC | 2208 | 2386 | 2564 | no data |
| 515 | Apis mellifera | NRC | 2209 | 2387 | 2565 | no data |
| 516 | Apis mellifera | NRC | 2210 | 2388 | 2566 | no data |
| 517 | Apis mellifera | NRC | 2211 | 2389 | 2567 | no data |
| 518 | Apis mellifera | NRC | 2212 | 2390 | 2568 | no data |
| 519 | Cotesia glomerata | R | 2213 | 2391 | 2569 | no data |
| 520 | Aposthonia gurneyi | R | 2214 | 2392 | 2570 | no data |
| 521 | Hilara sp. TDS-2007 | R | 2215 | 2393 | 2571 | no data |
| 522 | Hilara sp. TDS-2007 | R | 2216 | 2394 | 2572 | 1 |
| 523 | Hilara sp. TDS-2007 | R | 2217 | 2395 | 2573 | no data |
| 524 | Apotrechus illawarra | NRC | 2218 | 2396 | 2574 | no data |
| 525 | Apotrechus illawarra | R | 2219 | 2397 | 2575 | 3 |
| 526 | Cricula trifenestrata | R | 2220 | 2398 | 2576 | 2 |
| 527 | Antheraea yamamai | N | 2221 | 2399 | 2577 | no data |
| 528 | Antheraea yamamai | C | 2222 | 2400 | 2578 | no data |
| 529 | Antheraea yamamai | R | 2223 | 2401 | 2579 | no data |
| 530 | Antheraea yamamai | R | 2224 | 2402 | 2580 | no data |
| 531 | Antheraea yamamai | R | 2225 | 2403 | 2581 | no data |
| 532 | Antheraea yamamai | R | 2226 | 2404 | 2582 | no data |
| 533 | Antheraea pernyi | N | 2227 | 2405 | 2583 | no data |
| 534 | Antheraea pernyi | C | 2228 | 2406 | 2584 | no data |
| 535 | Antheraea pernyi | R | 2229 | 2407 | 2585 | no data |
| 536 | Antheraea pernyi | R | 2230 | 2408 | 2586 | 2 |
| 537 | Antheraea mylitta | R | 2231 | 2409 | 2587 | 2 |
| 538 | Saturnia japonica | N | 2232 | 2410 | 2588 | 2 |
| 539 | Saturnia japonica | R | 2233 | 2411 | 2589 | no data |
| 540 | Saturnia japonica | R | 2234 | 2412 | 2590 | 2 |
| 541 | Saturnia japonica | R | 2235 | 2413 | 2591 | no data |

TABLE 7-continued

Additional silk polypeptide sequences

| Construct # | Species | N/C/R sequence | Nucleotide SEQ ID NO | Nucleotide with flanking sequences SEQ ID NO: | Amino Acid SEQ ID NO: | Western Results (1 = no band 2 = weak band 3 = strong band) |
|---|---|---|---|---|---|---|
| 542 | Rhodinia fugax | N | 2236 | 2414 | 2592 | no data |
| 543 | Rhodinia fugax | R | 2237 | 2415 | 2593 | no data |
| 544 | Rhodinia fugax | R | 2238 | 2416 | 2594 | no data |
| 545 | Rhodinia fugax | R | 2239 | 2417 | 2595 | no data |
| 546 | Rhodinia fugax | R | 2240 | 2418 | 2596 | no data |
| 547 | Galleria mellonella | N | 2241 | 2419 | 2597 | 3 |
| 548 | Galleria mellonella | C | 2242 | 2420 | 2598 | 2 |
| 549 | Galleria mellonella | R | 2243 | 2421 | 2599 | no data |
| 550 | Galleria mellonella | R | 2244 | 2422 | 2600 | no data |
| 551 | Bombyx mori | N | 2245 | 2423 | 2601 | 3 |
| 552 | Bombyx mori | C | 2246 | 2424 | 2602 | 2 |
| 553 | Bombyx mori | R | 2247 | 2425 | 2603 | no data |
| 554 | Bombyx mori | R | 2248 | 2426 | 2604 | 2 |
| 555 | Bombyx mori | R | 2249 | 2427 | 2605 | no data |
| 556 | Anagasta kuehniella | N | 2250 | 2428 | 2606 | no data |
| 557 | Anagasta kuehniella | C | 2251 | 2429 | 2607 | no data |
| 558 | Anagasta kuehniella | R | 2252 | 2430 | 2608 | no data |
| 559 | Anagasta kuehniella | R | 2253 | 2431 | 2609 | no data |
| 560 | Antheraea pernyi | R | 2254 | 2432 | 2610 | 2 |
| 561 | Antheraea pernyi | C | 2255 | 2433 | 2611 | no data |
| 562 | Bacillus cereus | R | 2256 | 2434 | 2612 | 2 |
| 563 | Bacillus cereus | R | 2257 | 2435 | 2613 | 3 |
| 564 | Bacillus cereus | R | 2258 | 2436 | 2614 | 2 |
| 565 | Bacillus thuringiensis | R | 2259 | 2437 | 2615 | 2 |
| 566 | Bacillus licheniformis | R | 2260 | 2438 | 2616 | 2 |
| 567 | Bacillus licheniformis | R | 2261 | 2439 | 2617 | 1 |
| 568 | Neospora caninum | R | 2262 | 2440 | 2618 | no data |
| 569 | Danio rerio | R | 2263 | 2441 | 2619 | no data |
| 570 | Danio rerio | R | 2264 | 2442 | 2620 | no data |
| 571 | Danio rerio | R | 2265 | 2443 | 2621 | no data |
| 572 | Atta cephalotes | R | 2266 | 2444 | 2622 | 2 |
| 573 | Ureaplasma urealyticum | R | 2267 | 2445 | 2623 | 1 |
| 574 | Bombus terrestris | R | 2268 | 2446 | 2624 | no data |
| 575 | Bombus terrestris | R | 2269 | 2447 | 2625 | no data |
| 576 | Bombus impatiens | R | 2270 | 2448 | 2626 | no data |
| 577 | Bombus impatiens | R | 2271 | 2449 | 2627 | no data |
| 578 | Bombus impatiens | R | 2272 | 2450 | 2628 | no data |
| 579 | Bombus impatiens | R | 2273 | 2451 | 2629 | no data |
| 580 | Bombus impatiens | R | 2274 | 2452 | 2630 | 1 |
| 581 | Drosophila yakuba | R | 2275 | 2453 | 2631 | no data |
| 582 | Drosophila yakuba | R | 2276 | 2454 | 2632 | 2 |
| 583 | Pseudomonas syringae | R | 2277 | 2455 | 2633 | no data |
| 584 | Phytophthora infestans | R | 2278 | 2456 | 2634 | no data |
| 585 | Phytophthora sojae | R | 2279 | 2457 | 2635 | no data |
| 586 | Polysphondylium pallidum | R | 2280 | 2458 | 2636 | no data |
| 587 | Rhipicephalus pulchellus | R | 2281 | 2459 | 2637 | no data |
| 588 | Culex quinquefasciatus | R | 2282 | 2460 | 2638 | no data |
| 589 | Tribolium castaneum | R | 2283 | 2461 | 2639 | no data |
| 590 | Tribolium castaneum | R | 2284 | 2462 | 2640 | no data |
| 591 | Streptococcus pyogenes | R | 2285 | 2463 | 2641 | 2 |
| 592 | Candidatus Microthrix parvicella | R | 2286 | 2464 | 2642 | no data |
| 593 | Amphimedon queenslandica | R | 2287 | 2465 | 2643 | no data |
| 594 | Acyrthosiphon pisum | R | 2288 | 2466 | 2644 | no data |
| 595 | Acyrthosiphon pisum | R | 2289 | 2467 | 2645 | no data |
| 596 | Caenorhabditis brenneri | R | 2290 | 2468 | 2646 | no data |
| 597 | Caenorhabditis brenneri | R | 2291 | 2469 | 2647 | 2 |
| 598 | Burkholderia pseudomallei | R | 2292 | 2470 | 2648 | no data |
| 599 | Mustela putorius furo | R | 2293 | 2471 | 2649 | 3 |
| 600 | Candida parapsilosis | R | 2294 | 2472 | 2650 | no data |
| 601 | Candida parapsilosis | R | 2295 | 2473 | 2651 | no data |
| 602 | Candida parapsilosis | R | 2296 | 2474 | 2652 | no data |
| 603 | Paenibacillus sp | R | 2297 | 2475 | 2653 | no data |
| 604 | Xenopus (Silurana) tropicalis | R | 2298 | 2476 | 2654 | no data |
| 605 | Xenopus (Silurana) tropicalis | R | 2299 | 2477 | 2655 | 2 |
| 606 | Anopheles darlingi | R | 2300 | 2478 | 2656 | no data |
| 607 | Anopheles darlingi | R | 2301 | 2479 | 2657 | no data |
| 608 | Drosophila melanogaster | R | 2302 | 2480 | 2658 | 2 |
| 609 | Drosophila melanogaster | R | 2303 | 2481 | 2659 | no data |
| 610 | Synechococcus phage P60 | R | 2304 | 2482 | 2660 | no data |
| 611 | Amblyomma variegatum | R | 2305 | 2483 | 2661 | no data |
| 612 | Kazachstania naganishii | R | 2306 | 2484 | 2662 | no data |
| 613 | Drosophila ananassae | R | 2307 | 2485 | 2663 | no data |
| 614 | Tetrapisispora blattae | R | 2308 | 2486 | 2664 | 2 |

TABLE 7-continued

Additional silk polypeptide sequences

| Construct # | Species | N/C/R sequence | Nucleotide SEQ ID NO | Nucleotide with flanking sequences SEQ ID NO: | Amino Acid SEQ ID NO: | Western Results (1 = no band 2 = weak band 3 = strong band) |
|---|---|---|---|---|---|---|
| 615 | Tetrapisispora blattae | R | 2309 | 2487 | 2665 | no data |
| 616 | Monodelphis domestica | R | 2310 | 2488 | 2666 | no data |
| 617 | Amblyomma variegatum | R | 2311 | 2489 | 2667 | no data |
| 618 | Amblyomma variegatum | R | 2312 | 2490 | 2668 | no data |
| 619 | Latrodectus hesperus | R | 2313 | 2491 | 2669 | no data |
| 620 | Danaus plexippus | R | 2314 | 2492 | 2670 | no data |
| 621 | Encephalitozoon intestinalis | R | 2315 | 2493 | 2671 | no data |
| 622 | Encephalitozoon intestinalis | R | 2316 | 2494 | 2672 | no data |
| 623 | Psychromonas ingrahamii | R | 2317 | 2495 | 2673 | no data |
| 624 | Drosophila melanogaster | R | 2318 | 2496 | 2674 | no data |
| 625 | Chironomus tentans | R | 2319 | 2497 | 2675 | no data |
| 626 | Acyrthosiphon pisum | R | 2320 | 2498 | 2676 | 1 |
| 627 | Megachile rotundata | R | 2321 | 2499 | 2677 | no data |
| 628 | Megachile rotundata | R | 2322 | 2500 | 2678 | no data |
| 629 | Acyrthosiphon pisum | R | 2323 | 2501 | 2679 | no data |
| 630 | Pseudomonas syringae | R | 2324 | 2502 | 2680 | no data |
| 631 | Nematostella vectensis | R | 2325 | 2503 | 2681 | no data |
| 632 | Dasypus novemcinctus | R | 2326 | 2504 | 2682 | 3 |
| 633 | Trichoderma harzianum | R | 2327 | 2505 | 2683 | 3 |
| 634 | Nematostella vectensis | R | 2328 | 2506 | 2684 | no data |
| 635 | Nematostella vectensis | R | 2329 | 2507 | 2685 | no data |
| 636 | Caenorhabditis elegans | R | 2330 | 2508 | 2686 | no data |
| 637 | Leishmania mexicana | R | 2331 | 2509 | 2687 | no data |
| 638 | Chelonia mydas | R | 2332 | 2510 | 2688 | 2 |
| 639 | Nasonia vitripennis | R | 2333 | 2511 | 2689 | no data |
| 640 | Euprymna scolopes | NRC | 2334 | 2512 | 2690 | no data |

Example 10

Circularly Permuted Variants of *Argiope bruennichi* MaSp2 Polypeptides

Figure 15:
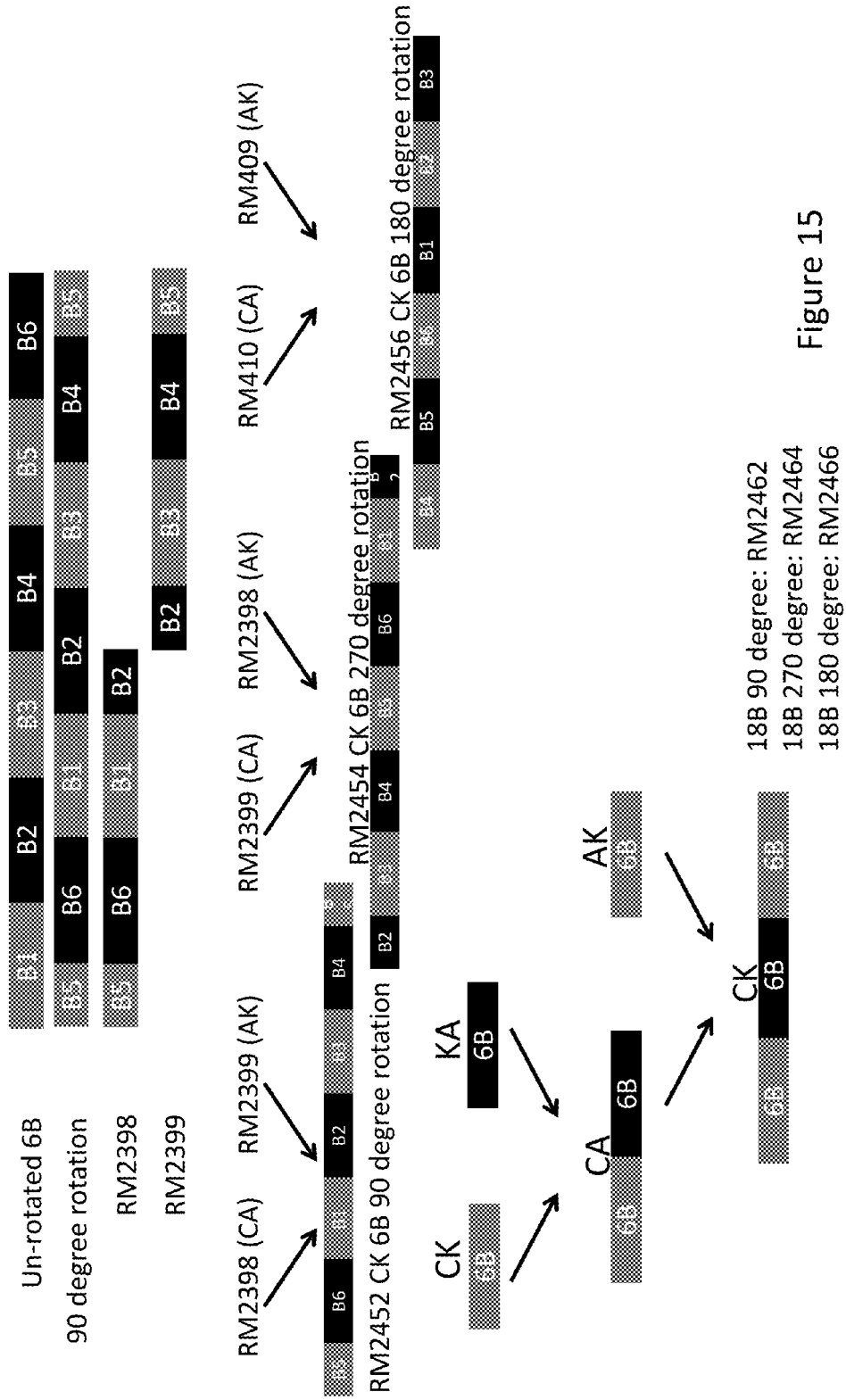
FIG. 15 illustrates the assembly of circularly permuted variants of an 18B polypeptide, according to embodiments of the invention.

The 6 repeat blocks (block co-polymer) from *Argiope bruennichi* MaSp2 identified in Example 5 were circularly permuted by approximately 90 degrees (by moving ~1.5 blocks from the end of the six blocks to the beginning), then divided into 2 R sequences consisting of ~3 blocks each, RM2398 (SEQ ID NO: 2708) and RM2399 (SEQ ID NO: 2709). These 3-block sequences were subsequently used to generate 6-block sequences rotated by ~90 and ~270 degrees from the original 6-block sequence, and existing 3-block sequences (RM409 and RM410) were used to generate a 6-block sequence rotated by ~180 degrees. Each 6-block sequence was then assembled into 18-block sequences. The assembly process and rotated sequences are depicted in FIG. 15.

Figure 16:
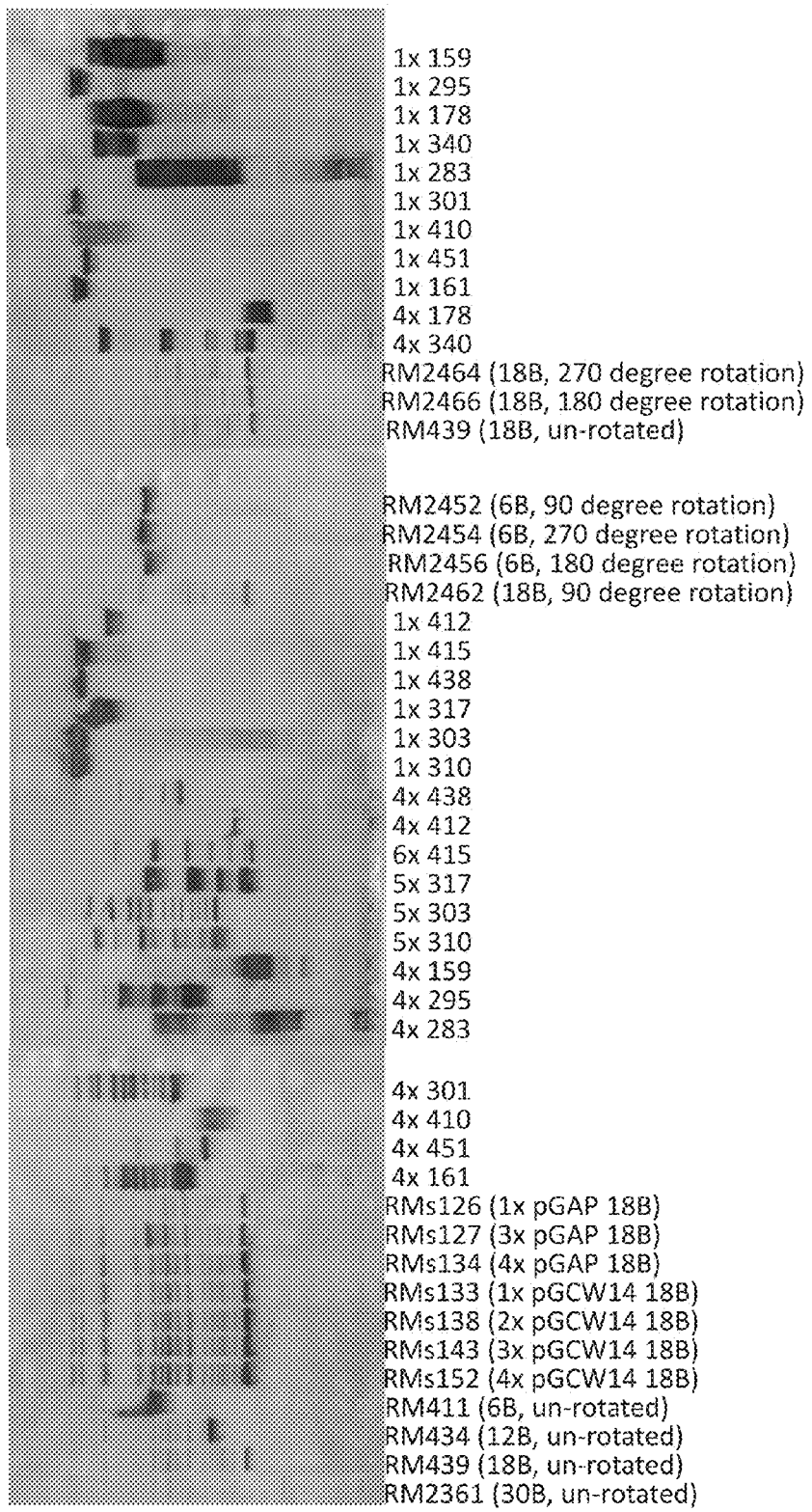
FIG. 16 shows a western blot of expressed block copolymer peptides build using silk repeat domains consisting of between 1 and 6 R domains, including circularly permuted variants and variants expressed by different promoters or different copy numbers.

To generate RM2398 and RM2399, plasmid RM439 (SEQ ID NO: 467) was amplified by PCR using either primers RM2398F (5'-CTAAGAGGTCTCACAGGTAGT-CAAGGACCTGGTTCAGG-3') (SEQ ID NO: 2834) and RM2398R (5'-TTCAGTGGTCTCTACCTTGTTGTCCTC-CAGATCCAG-3') (SEQ ID NO: 2835) or RM2399F (5'-CTAAGAGGTCTCACAGGTCCTGGAGGTCAGGGTC-CAT-3') (SEQ ID NO: 2836) and RM2399R (5'-TTCAGTGGTCTCTACCTGGTCCCTGTTGACCAG-CACCAGGA-3') (SEQ ID NO: 2837). Each reaction consisted of 12.5 μL 2×KOD Extreme Buffer, 0.25 μl KOD Extreme Hot Start Polymerase, 0.5 μl 10 μM Fwd oligo, 0.5 μl 10 μM Rev oligo, 5 ng template DNA (RM439), 0.5 μl of 10 mM dNTPs, and ddH2O added to final volume of 25 μl. Each reaction was then thermocycled according to the program:
1. Denature at 94° C. for 5 minutes
2. Denature at 94° C. for 30 seconds
3. Anneal at 55° C. for 30 seconds
4. Extend at 72° C. for 60 seconds
5. Repeat steps 2-4 for 29 additional cycles
6. Final extension at 72° C. for 5 minutes Resulting linear DNA was digested with BsaI and ligated into assembly vectors RM2086 (SEQ ID NO: 2693) and RM2089 (SEQ ID NO: 2695) that had been digested with BsmBI. Ligated material was transformed into *E. coli* for clonal isolation, DNA amplification, and sequence verification using standard methods. Using the 2ab assembly process described in Example 5 (with minor modifications to the assembly vectors to shift the BtgZI cut sites further away from the silk sequences), the 3-block fragments were assembled into two different 6-block fragments, one with RM2398 proceeding RM2399 (producing RM2452-SEQ ID NO: 2710), and one with RM2399 proceeding RM2398 (producing RM2454-SEQ ID NO: 2712). Additionally, RM409 (SEQ ID NO 463) and RM410 (SEQ ID NO 464) were digested out of the assembly vector RM396 with BbsI and BsaI, and ligated into vector RM2105 (SEQ ID NO: 2691) that had been digested with BbsI and BsaI and treated with Calf Intestinal Alkaline Phosphatase. Ligated material was transformed into *E. coli* for clonal isolation, DNA amplification, and sequence verification using standard methods. The resulting plasmids were subsequently digested with AscI and SbfI and the fragments encoding a silk isolated by gel electrophoresis, fragment excision, and gel extraction. The fragments were subsequently ligated into assembly vectors RM2086 and RM2089 that had been digested with AscI and SbfI. Ligated material was transformed into *E. coli* for clonal isolation, DNA amplification, and sequence verification using standard methods. Using 2ab assembly, a 6-block fragment consisting of RM410 proceeding RM409 was generated (producing RM2456-SEQ ID NO: 2711). RM2452, RM2454, and RM2456 were digested from assembly vector RM2081 (SEQ ID NO: 2692) with AscI and SbfI, and ligated into assembly vectors RM2088 and RM2089 that had been digested with AscI and SbfI. Ligated material was transformed into E. coli for clonal isolation, DNA amplification, and sequence verification using standard methods. Using 2ab assembly, 18-block sequences were generated from each of the three 6-block fragments, resulting in sequences RM2462 (SEQ ID NO: 2713), RM2464 (SEQ ID NO: 2715), and RM2466 (SEQ ID NO: 2714). Each of the 6-block and 18-block sequences was then digested from the assembly vector using BsaI and BbsI, and the fragments encoding a silk isolated by gel electrophoresis, fragment excision, and gel extraction. The fragments were subsequently ligated expression vector RM1007 (SEQ ID NO: 2707) that had been digested with BsmBI and treated with Calf Intestinal Alkaline Phosphatase. Ligated material was transformed into E. coli for clonal isolation, DNA amplification, and sequence verification using standard methods. Resulting plasmids were linearized with BsaI and used to transform Pichia (Komagataella) pastoris (strain RMs71, described in Example 3) using the PEG method (Cregg, J. M. et al., DNA-mediated transformation, Methods Mol. Biol., 389, pg. 27-42 (2007)). Transformants were plated on Yeast Extract Peptone Dextrose Medium (YPD) agar plates containing 25 μg/ml nourseothricin and incubated for 48 hours at 30° C. Two clones from each transformation were inoculated into 400 μl of Buffered Glycerol-complex Medium (BMGY) in a 96-well square-well block, and incubated for 48 hours at 30° C. with agitation at 1000 rpm. Cells were pelleted via centrifugation, and the supernatant was recovered for analysis of silk polypeptide content via western blot analysis of the 3× FLAG epitope. Western blot data for a representative clone of each polypeptide is shown in FIG. 16. Expression and secretion of each of the circularly permuted polypeptides appears comparable to its un-rotated counterpart. This suggests that any number of starting positions can be selected for identifying blocks in repeated silk or silk-like polypeptides without consequence on the expression or secretion of polypeptides composed of those blocks.

Example 11

Changing Expression of an Argiope bruennichi MaSp2 Polynucleotide Through Control of Copy Number and Promoter Strength The degree of transcription of an exogenously introduced polynucleotide is known to affect the amount of polypeptide produced (see e.g. Liu, H., et al., Direct evaluation of the effect of gene dosage on secretion of protein from yeast Pichia pastoris by expressing EGFP, J. Microbiol. Biotechnol., 24:2, pg. 144-151 (2014); and Hohenblum, H., et al., Effects of gene dosage, promoters, and substrates on unfolded protein stress of recombinant Pichia pastoris, Biotechnol. Bioeng., 85:4, pg. 367-375 (2004)). In Pichia (Komagataella) pastoris, the degree of transcription is commonly controlled either by increasing the number of copies of a polynucleotide that are integrated into the host genome or by selecting an appropriate promoter to drive transcription (see e.g. Hartner, F. S., et al., Promoter library designed for fine-tuned gene expression in Pichia pastoris, Nucleic Acids Res., 36:12 (2008); Zhang, A. L., et al., Recent advances on the GAP promoter derived expression system of Pichia pastoris, Mol. Biol. Rep., 36:6, pg. 1611-1619 (2009); Ruth, C., et al., Variable production windows for porcine trypsinogen employing synthetic inducible promoter variants in Pichia pastoris, Syst. Synth. Biol., 4:3, pg. 181-191 (2010); Stadlmayr, G., et al., Identification and characterisation of novel Pichia pastoris promoters for heterologous protein production, J. Biotechnol., 150:4, pg. 519-529 (2010)). A relatively recent addition to the set of promoters used for heterologous protein expression is pGCW14 (Liang, S., Identification and characterization of P GCW14: a novel, strong constitutive promoter of Pichia pastoris, Biotechnol. Lett. 35:11, pg. 1865-1871 (2013)), which is reported to be 5-10 times stronger than pGAP. To validate that the expression and secretion of silk and silk-like polypeptides can also be influenced by copy number, strains containing 1, 3, or 4 copies of pGAP driving expression of 18B (described in Example 5) and strains containing 1, 2, 3, or 4 copies of pGCW14 driving expression of 18B were generated and tested. The strains are described in Table 8.

TABLE 8

Strains with multiple polynucleotide sequences or different promoters

| Strain ID | Description | Derived From | Newly incorporated sequence(s) | Selection |
|---|---|---|---|---|
| RMs126 | 1x pGAP 18B | GS115 (NRRL Y15851) | RM439 in RM630 | Minimal Dextrose |
| RMs127 | 3x pGAP 18B | RMs126 | RM439 in RM632 and RM633 | nourseothricin, hygromycin B |
| RMs134 | 4x pGAP 18B | RMs127 | RM439 in RM631 | G418 |
| RMs133 | 1x pGCW14 18B | GS115 (NRRL Y15851) | RM439 in RM812 | Minimal Dextrose |
| RMs138 | 2x pGCW14 18B | RMs133 | RM439 in RM814 | nourseothricin |
| RMs143 | 3x pGCW14 18B | RMs138 | RM439 in RM815 | hygromycin B |
| RMs152 | 4x pGCW14 18B | RMs143 | RM439 in RM837 | G418 |

The polynucleotide sequence encoding alpha mating factor+18B+3× FLAG tag was digested from the plasmid described in Example 5 (RM468, SEQ ID NO: 1401, with RM439, SEQ ID NO: 467 cloned in) using restriction enzyme AscI and SbfI. The fragment encoding alpha mating factor+18B+3× FLAG tag was isolated by gel electrophoresis, fragment excision, and gel extraction. The resulting linear DNA was ligated into expression vectors RM630 (SEQ ID NO: 2697), RM631 (SEQ ID NO: 2698), RM632 (SEQ ID NO: 2699), RM633 (SEQ ID NO: 2700), RM812 (SEQ ID N: 2701), RM837 (SEQ ID NO: 2702), RM814 (SEQ ID N: 2703), and RM815 (SEQ ID NO: 2704) that had been digested with AscI and SbfI. Key attributes of the expression vectors are summarized in Table 9, and sequences include SEQ ID NOs: 2691-2707. Ligated material was transformed into E. coli for clonal isolation, DNA amplification, and sequence verification using standard methods.

TABLE 9

Additional vectors

| Vector ID | SEQ ID NO: | Description |
|---|---|---|
| RM2105 | 2691 | Vector for receiving silks before transfer to some assembly vectors. p15a origin, gentamycin resistance |
| RM2081 | 2692 | CK assembly vector with revised BtgZI targeting, p15a origin |
| RM2086 | 2693 | CA assembly vector with revised BtgZI targeting, p15a origin |
| RM2088 | 2694 | KA assembly vector with revised BtgZI targeting, p15a origin |
| RM2089 | 2695 | AK assembly vector with revised BtgZI targeting, p15a origin |

TABLE 9-continued

Additional vectors

| Vector ID | SEQ ID NO: | Description |
|---|---|---|
| RM747 | 2696 | Vector for receiving silks before transfer to some assembly vectors. p15a origin, gentamycin resistance |
| RM630 | 2697 | Expression vector. Integrates into HIS4 locus. pGAP promoter. |
| RM631 | 2698 | Expression vector. Integrates into AOX2 locus. pGAP promoter. Confers G418 resistance |
| RM632 | 2699 | Expression vector. Integrates into HSP82 locus. pGAP promoter. Confers nourseothricin resistance |
| RM633 | 2700 | Expression vector. Integrates into TEF1 locus. pGAP promoter. Confers hygromycin B resistance |
| RM812 | 2701 | Expression vector. Integrates into HIS4 locus. pGCW14 promoter. |
| RM837 | 2702 | Expression vector. Integrates into AOX2 locus. pGCW14 promoter. Confers G418 resistance |
| RM814 | 2703 | Expression vector. Integrates into HSP82 locus. pGCW14 promoter. Confers nourseothricin resistance |
| RM815 | 2704 | Expression vector. Integrates into TEF1 locus. pGCW14 promoter. Confers hygromycin B resistance |
| RM785 | 2705 | Expression vector. Integrates into pGAP locus. pGAP promoter. Confers nourseothricin resistance |
| RM793 | 2706 | Expression vector. Integrates into HSP82 locus. pGAP promoter. Confers nourseothricin resistance |
| RM1007 | 2707 | Expression vector. Integrates into pGAP locus. pGAP promoter. Confers nourseothricin resistance |

The polynucleotide encoding 18B in expression vector RM630 was linearized with BsaI and transformed into *Pichia (Komagataella) pastoris* (strain GS115-NRRL Y15851) using the PEG method (Cregg, J. M. et al., DNA-mediated transformation, *Methods Mol. Biol.*, 389, pg. 27-42 (2007)). Transformants were plated on Minimal Dextrose (MD) agar plates (no added amino acids) and incubated for 48 hours at 30° C. This resulted in creation of strain RMs126, 1xpGAP 18B.

RMs126 was subsequently co-transformed with the polynucleotide encoding 18B in expression vectors RM632 and RM633 (linearized with BsaI) using the electroporation method (Wu., S., and Letchworth, G. J., High efficiency transformation by electroporation of *Pichia pastoris* pretreated with lithium acetate and dithiothreitol, *Biotechniques*, 36:1, pg. 152-154 (2004)). Transformants were plated on Yeast Extract Peptone Dextrose Medium (YPD) agar plates containing 25 µg/ml nourseothricin and 100 ug/ml hygromycin B and incubated for 48 hours at 30° C. This resulted in creation of strain RMs127, 3xpGAP 18B.

RMs127 was subsequently transformed with the polynucleotide encoding 18B in expression vector RM631 (linearized with BsaI) using the PEG method. Transformants were plated on Yeast Extract Peptone Dextrose Medium (YPD) agar plates containing 300 µg/ml G418 and incubated for 48 hours at 30° C. This resulted in creation of strain RMs134, 4xpGAP 18B.

To generate strains RMs133, RMs138, RMs143, and RMs152 (1x, 2x, 3x, and 4x p754 18B, respectively), strain GS115 (NRRL Y15851) was serially transformed with the polynucleotide encoding 18B in expression vectors RM812, RM814, RM815, and RM837 (after linearizing with BsaI) using the PEG method.

A clone of each strain was inoculated into 400 µl of Buffered Glycerol-complex Medium (BMGY) in a 96-well square-well block, and incubated for 48 hours at 30° C. with agitation at 1000 rpm. Cells were pelleted via centrifugation, and the supernatant was recovered for analysis of block copolymer polypeptide content via western blot analysis of the 3x FLAG epitope. Western blot data for a representative clone of each polypeptide is shown in FIG. 16. Increasing band intensities suggest that higher transcription resulted in the expression and secretion of additional block copolymer polypeptide, confirming that the strategy of increasing transcription functions on block copolymer based on silk and silk-like polypeptide repeat units.

Example 12

Comparing Expression and Secretion of Single R Domains to Homopolymers of R Domains Additional selected R domains from SEQ ID NOs: 1-1398 that expressed and secreted well were concatenated into 4 to 6x repeat domains using the 2ab assembly (described in Example 5). Additionally, 2ab assembly was used to concatenate a 12B sequence with an 18B sequence (from Example 5), resulting in a 30B sequence. The resulting products were transferred into an expression vector, such that each silk sequence is flanked by alpha mating domain on the 5' end and a 3x FLAG domain on the 3' end and driven by a pGAP promoter. The sequences generated are described in Table 10, and the sequences include SEQ ID NOs: 2734-2748.

TABLE 10

Additional full-length block copolymer constructs with alpha mating factor, multiple repeat domains, and 3X FLAG domains

| Construct ID | DNA (with alpha mating factor and 3x FLAG) SEQ ID NO: | Amino acid (with alpha mating factor and 3x FLAG) SEQ ID NO: | Predicted Molecular Weight of Secreted Product (kDa) | Expression Vector |
|---|---|---|---|---|
| 4x 438 | 2724 | 2734 | 63.4 | RM652 |
| 4x 412 | 2725 | 2735 | 77.1 | RM1007 |
| 6x 415 | 2726 | 2736 | 75.9 | RM1007 |
| 5x 317 | 2727 | 2737 | 70.1 | RM1007 |
| 5x 303 | 2728 | 2738 | 62.0 | RM1007 |
| 5x 310 | 2729 | 2739 | 62.7 | RM1007 |
| 4x 301 | 2730 | 2740 | 47.3 | RM793 |
| 4x 410 | 2731 | 2741 | 52.3 | RM793 |
| 4x 451 | 2732 | 2742 | 57.7 | RM793 |
| 4x 161 | 2733 | 2743 | 44.9 | RM785 |
| RM2361 (30B) | 2744 | 2745 | 135.1 | RM1007 |
| RM411 (6B) | 2746 | 2749 | 29.5 | RM1007 |
| RM434 (12B) | 2747 | 2750 | 55.9 | RM1007 |
| RM439 (18B) | 2748 | 2751 | 82.31 | RM1007 |

The block copolymer expression vectors were then transformed into *Pichia (Komagataella) pastoris* (strain RMs71, described in Example 3) using the PEG method (Cregg, J. M. et al., DNA-mediated transformation, *Methods Mol. Biol.*, 389, pg. 27-42 (2007)). Transformants were plated on YPD agar plates containing 25 µg/ml nourseothricin and incubated for 48 hours at 30° C. Three clones from each transformation were picked into 400 µl of BMGY in a 96-well square-well block, and incubated for 48 hours at 30° C. with agitation at 1000 rpm. Cells were pelleted via centrifugation, and the supernatant was recovered for analysis of silk polypeptide content via western blot. A representative clone for each block copolymer construct, as well as the 1xR domain counterpart and 4xR domain constructs from Example 6, are show in FIG. 16. As observed in Example 6, streakiness and multiple bands are evident on the western blot. While the specific source of these variations has not been identified, they are generally consistent with typically observed phenomena, including polypeptide degradation and post-translational modification (e.g. glycosylation). Further, the band intensity of 4-6×R domain polypeptides appears to be weaker than the corresponding 1×R domain constructs. This is also evident in the 6B, 12B, 18B, and 30B series of *Argiope bruennichi* MaSp2 polypeptides. This suggests that longer block copolymers comprising silk repeat sequences are generally less well expressed and secreted than shorter block copolymer sequences comprising the same or different repeat sequences.

Example 13

Measuring Productivity of Strains Expressing and Secreting Silks

Table 11 lists the volumetric and specific productivities of strains expressing the polypeptides described in Example 10, Example 11, and Example 12.

TABLE 11

Productivity of strains producing silk polypeptides

| Construct ID | Volumetric productivity (mg silk/liter/hour) | Volumetric productivity error (SD, n = 3) | Specific productivity (mg silk/g DCW/hour) | Specific productivity error (SD, n = 3) |
|---|---|---|---|---|
| 1x 159 | 5.82 | 0.29 | 1.70 | 0.18 |
| 1x 295 | 5.47 | 0.27 | 1.64 | 0.17 |
| 1x 179 | 3.90 | 0.92 | 1.16 | 0.33 |
| 1x 340 | 4.94 | 0.05 | 1.45 | 0.10 |
| 1x 283 | 7.57 | 0.48 | 2.28 | 0.26 |
| 1x 301 | 3.75 | 0.27 | 1.11 | 0.14 |
| 1x 410 | 4.31 | 0.28 | 1.34 | 0.03 |
| 1x 451 | 6.69 | 0.36 | 2.16 | 0.11 |
| 1x 161 | 4.55 | 0.09 | 1.45 | 0.22 |
| 4x 478 | 1.08 | 0.17 | 0.34 | 0.09 |
| 4x 340 | 4.91 | 0.59 | 1.58 | 0.41 |
| RM2464 (18B, 270 degree rotation) | 19.13 | 0.14 | 5.25 | 0.64 |
| RM2466 (18B, 180 degree rotation) | 15.70 | 0.60 | 4.48 | 0.61 |
| RM439 (18B, unrotated) | 19.22 | 0.84 | 5.53 | 0.68 |
| RM2452 (6B, 90 degree rotation) | 9.28 | 0.07 | 2.63 | 0.15 |
| RM2454 (6B, 180 degree rotation) | 10.76 | 0.40 | 3.18 | 0.22 |
| RM2456 (6B, 180 degree rotation) | 10.21 | 0.23 | 2.99 | 0.22 |
| RM2462 (18B, 90 degree rotation) | 15.25 | 0.56 | 4.69 | 0.33 |
| 1x 412 | 2.95 | 0.53 | 0.96 | 0.22 |
| 1x 415 | 7.67 | 0.69 | 2.18 | 0.04 |
| 1x 438 | 5.69 | 0.57 | 1.59 | 0.26 |
| 1x 317 | 4.61 | 0.09 | 1.25 | 0.13 |
| 1x 303 | 5.41 | 0.11 | 1.52 | 0.15 |
| 1x 310 | 6.65 | 0.06 | 1.93 | 0.19 |
| 4x 438 | 1.68 | 0.24 | 0.50 | 0.03 |
| 4x 412 | 1.29 | 0.14 | 0.35 | 0.01 |
| 6x 415 | 0.50 | 0.15 | 0.14 | 0.03 |
| 5x 317 | 5.15 | 0.28 | 1.43 | 0.07 |
| 5x 303 | 0.63 | 0.07 | 0.19 | 0.03 |
| 5x 310 | 0.52 | 0.07 | 0.15 | 0.03 |
| 4x 159 | 24.81 | 2.38 | 7.72 | 0.82 |
| 4x 295 | 4.92 | 0.56 | 1.60 | 0.26 |
| 4x 283 | 18.70 | 0.58 | 5.87 | 0.57 |
| 4x 301 | 0.45 | 0.06 | 0.14 | 0.01 |
| 4x 410 | 1.49 | 0.05 | 0.47 | 0.05 |
| 4x 451 | 2.13 | 0.12 | 0.68 | 0.05 |
| 4x 161 | 1.80 | 0.14 | 0.57 | 0.03 |
| RMs126 (1x pGAP 18B) | 14.21 | 1.11 | 4.56 | 0.63 |
| RMs127 (3x pGAP 18B) | 28.61 | 2.05 | 8.81 | 0.80 |
| RMs134 (4x pGAP 18B) | 30.89 | 1.48 | 9.73 | 0.83 |
| RMs133 (1x pGCW14 18B) | 36.90 | 2.43 | 12.14 | 1.39 |
| RMs138 (2x pGCW14 18B) | 47.31 | 3.66 | 16.42 | 1.45 |
| RMs143 (3x pGCW14 18B) | 56.49 | 0.97 | 20.96 | 0.72 |
| RMs152 (4x pGCW14 18B) | 58.06 | 4.31 | 20.97 | 3.74 |
| RM411 (6B, un-rotated) | 12.01 | 1.16 | 3.76 | 0.31 |
| RM434 (12B, un-rotated) | 17.57 | 1.47 | 5.50 | 0.22 |
| RM439 (18B, un-rotated) | 14.36 | 1.25 | 4.56 | 0.21 |
| RM2361 (30B, un-rotated) | 8.81 | 0.58 | 2.87 | 0.39 |

To measure productivity, 3 clones of each strain were inoculated into 400 μl of Buffered Glycerol-complex Medium (BMGY) in a 96-well square-well block, and incubated for 48 hours at 30° C. with agitation at 1000 rpm. Following the 48-hour incubation, 4 μl of each culture was used to inoculate a fresh 400 μl of BMGY in a 96-well square-well block, which was then incubated for 24 hours 30° C. with agitation at 1000 rpm. Cells were then pelleted by centrifugation, the supernatant removed, and the cells resuspended in 400 μl of fresh BMGY. The cells were again pelleted by centrifugation, the supernatant removed, and the cells resuspended in 800 μl of fresh BMGY. From that 800 μl, 400 μl was aliquoted into a 96-well square-well block, which was then incubated for 2 hours at 30° C. with agitation at 1000 rpm. After the 2 hours, the OD600 of the cultures was recorded, and the cells were pelleted by centrifugation and the supernatant collected for further analysis. The concentration of block copolymer polypeptide in each supernatant was determined by direct enzyme-linked immunosorbent assay (ELISA) analysis quantifying the 3× FLAG epitope.

The relative productivities of each strain confirm qualitative observations made based on western blot data. The circularly permuted polypeptides express at similar levels to un-rotated silks, stronger promoters or more copies lead to higher block copolymer expression and secretion, and longer block copolymer polypeptides comprising silk repeat sequences generally express less well than shorter block copolymers comprising the same or different repeat sequences. Interestingly, the grams of 12B (55.9 kDa) produced exceeds the grams of 6B (29.5 kDa) produced, suggesting that the factors leading to decreased expression of larger block copolymers comprising silk repeat sequences may not become dominant until expression of block copolymers closer to the size of 18B (82.2 kDa) Importantly, most of the block copolymer polypeptides have a relatively high specific productivity (>0.1 mg silk/g Dry Cell Weight (DCW)/hour. In some embodiments, the productivity is above 2 mg silk/g DCW/hour. In further embodiments, the productivity is above 5 mg silk/g DCW/hour), before any optimization of the level of polypeptide transcription. Additional transcription improved the productivity of 18B by approximately 5-fold to 20 (almost 21) mg polypeptide/g DCW/hour.

Example 14

Measuring Mechanical Properties of Silk Fiber

The block copolymer polypeptide produced in Example 5 was spun into a fiber and tested for various mechanical properties. First, a fiber spinning solution was prepared by dissolving the purified and dried block copolymer polypeptide in a formic acid-based spinning solvent, using standard techniques. Spin dopes were incubated at 35° C. on a rotational shaker for three days with occasional mixing. After three days, the spin dopes were centrifuged at 16000 rcf for 60 minutes and allowed to equilibrate to room temperature for at least two hours prior to spinning.

Figure 17:
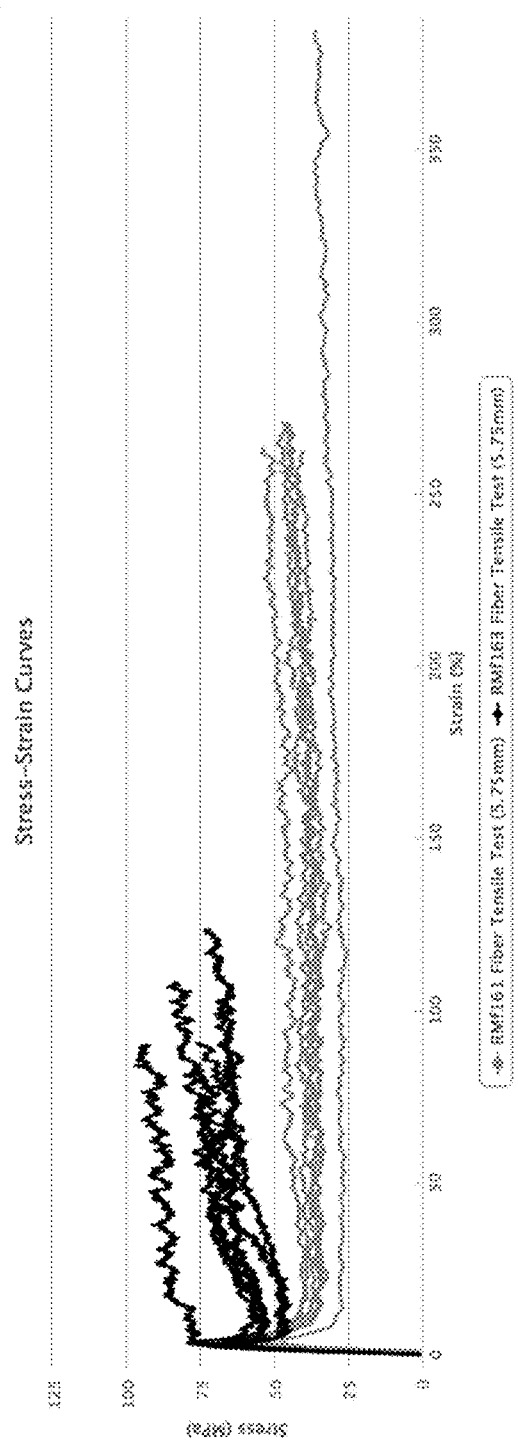
FIG. 17 are stress-strain curves showing the effect of draw ratio of block copolymer fibers of an 18B polypeptide.

The spin dope was extruded through a 50-200 μm diameter orifice into a standard alcohol-based coagulation bath. Fibers were pulled out of the coagulation bath under tension, drawn from 1 to 5 times their length, and subsequently allowed to dry. At least five fibers were randomly selected from the at least 10 meters of spun fibers. These fibers were tested for tensile mechanical properties using an instrument including a linear actuator and calibrated load cell. Fibers were pulled at 1% strain until failure. Fiber diameters were measured with light microscopy at 20× magnification using image processing software. The mean maximum stress ranged from 54-310 MPa. The mean yield stress ranged from 24-172 MPa. The mean maximum strain ranged from 2-200%. The mean initial modulus ranged from 1617-5820 MPa. The effect of the draw ratio is illustrated in Table 12 and FIG. 17. Also, the average toughness of three fibers was measured at 0.5 MJ m$^{-3}$ (standard deviation of 0.2), 20 MJ m$^{-3}$ (standard deviation of 0.9), and 59.2 MJ m$^{-3}$ (standard deviation of 8.9)

TABLE 12

Effect of draw ratio

|  | 2.5x | 5x |
|---|---|---|
| Mean Maximum Stress (MPa) | 58 | 80 |
| Mean Yield Stress (Mpa) | 53 | 61 |
| Mean max strain (%) | 277 | 94 |
| Mean initial modulus (MPa) | 1644 | 2719 |

Fiber diameters were determined as the average of at least 4-8 fibers selected randomly from at least 10 m of spun fibers. For each fiber, six measurements were made over the span of 0.57 cm. The diameters ranged from 4.48-12.7 μm. Fiber diameters were consistent within the same sample. Samples ranged over various average diameters: 10.3 μm (standard deviation of 0.4 μm), 13.47 μm (standard deviation of 0.36 μm), 12.05 μm (standard deviation of 0.67), 14.69 μm (standard deviation of 0.76 μm), and 9.85 μm (standard deviation of 0.38 μm).

Figure 18:
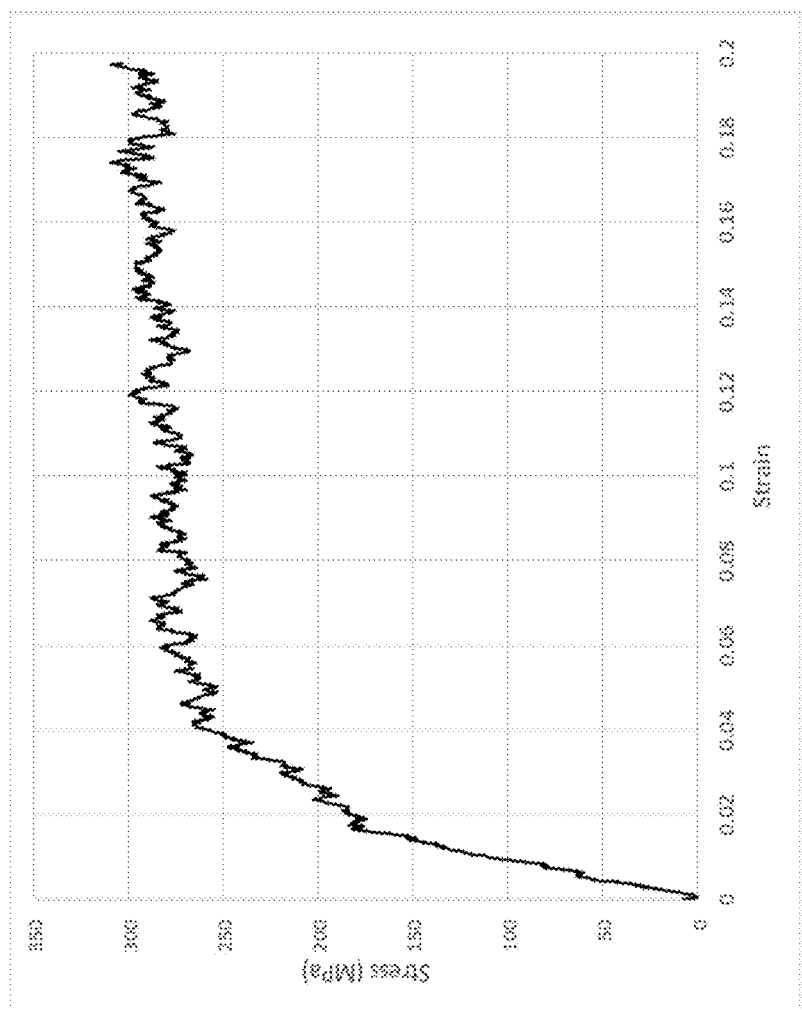
FIG. 18 is a stress-strain curve for a block copolymer fiber comprising SEQ ID NO: 1398.

One particularly effective fiber which was spun from block copolymer material that was generated from an optimized recovery and separations protocol had a maximum ultimate tensile strength of 310 MPa, a mean diameter of 4.9 μm (standard deviation of 0.8), and a max strain of 20%. Fiber tensile test results are shown in FIG. 18.

Figure 19:
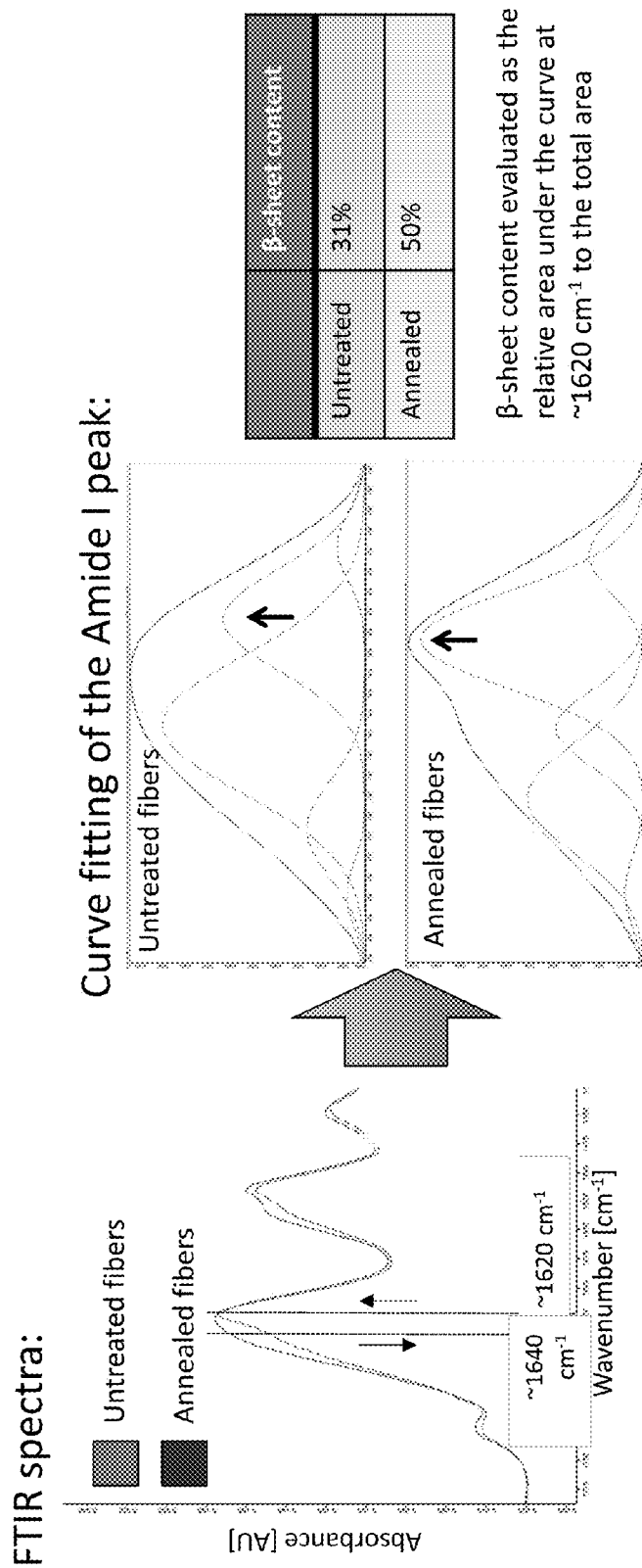
FIG. 19 shows the results of FTIR spectra for untreated and annealed block copolymer fibers.

Fibers were dried overnight at room temperature. FTIR spectra were collected with a diamond ATR module from 400 cm$^{-1}$ to 4000 cm$^{-1}$ with 4 cm$^{-1}$ resolution (FIG. 19). The amide I region (1600 cm$^{-1}$ to 1700 cm$^{-1}$) was baselined and curve fitted with Gaussian profiles at 5-6 location determined by peak locations from the second derivative of the original curve. The β-sheet content was determined as the area under the Gaussian profile at ~1620 cm$^{-1}$ and ~1690 cm$^{-1}$ divided by the total area of the amide I region. Annealed and untreated fibers were tested. For annealing, fibers were incubated within a humidified vacuum chamber at 1.5 Torr for at least six hours. Untreated fibers were found to contain 31% β-sheet content, and annealed fibers were found to contain 50% β-sheet content.

Figure 20:
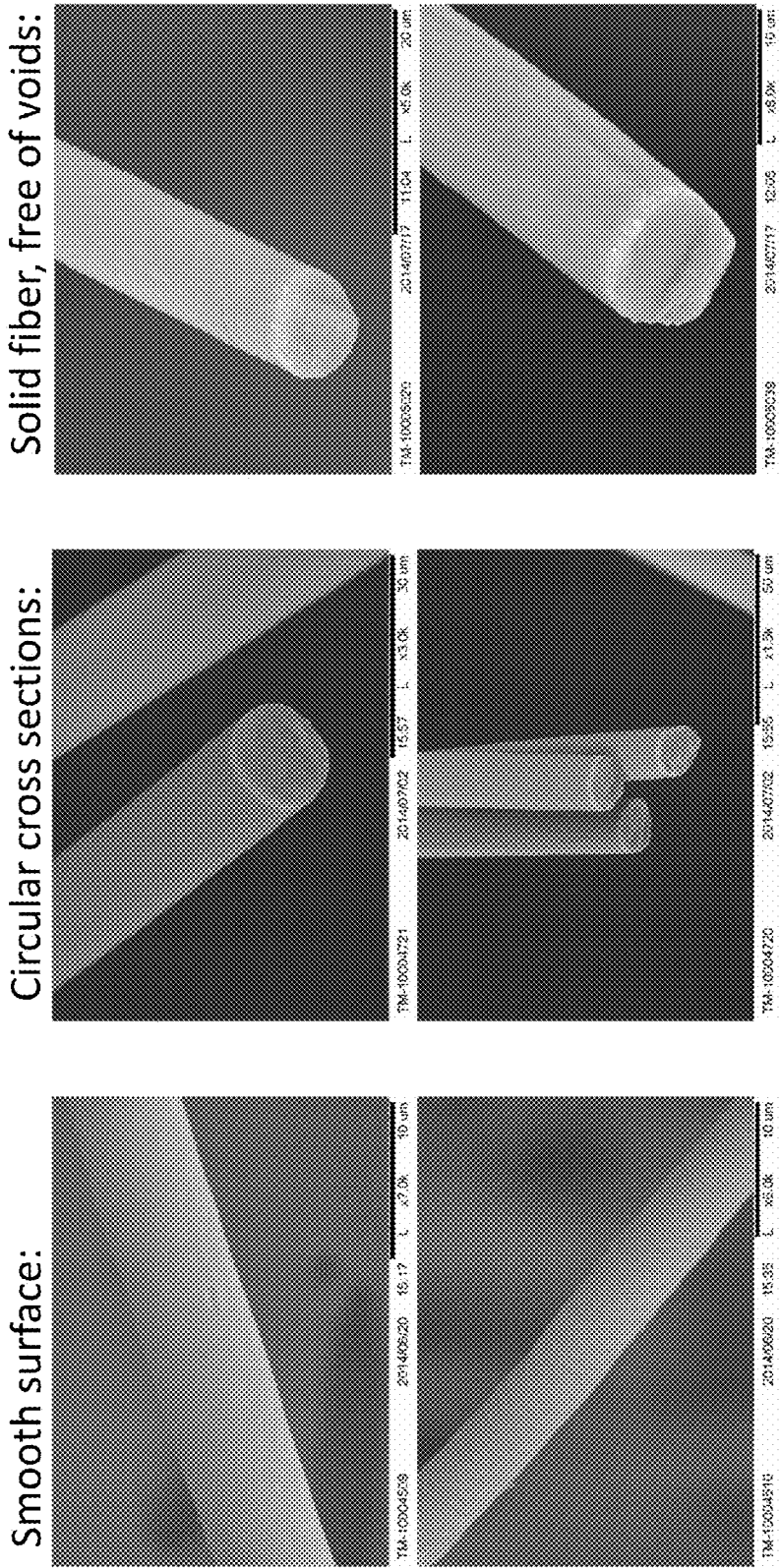
FIG. 20 shows scanning electron micrographs of block copolymer fibers of the invention.

Fiber cross-sections were examined by freeze fracture using liquid nitrogen. Samples were sputter coated with platinum/palladium and imaged with a Hitachi TM-1000 at 5 kV accelerating voltage. FIG. 20 shows that the fibers have smooth surfaces, circular cross sections, and are solid and free of voids. In some embodiments Example 15

Production of Optimal Fibers

An R domain of MaSp2-like silks is selected from those listed in Tables 13a and 13b, and the R domain is concatenated into 4× repeat domains flanked by alpha mating factor on the 5' end and 3× FLAG on the 3' end using the assembly scheme shown in FIG. 12. The concatenation is performed as described in Example 4 and shown in FIG. 7 and FIG. 8. The resulting polynucleotide sequence and corresponding polypeptide sequences are listed in Tables 13a and 13b.

Figure 21:
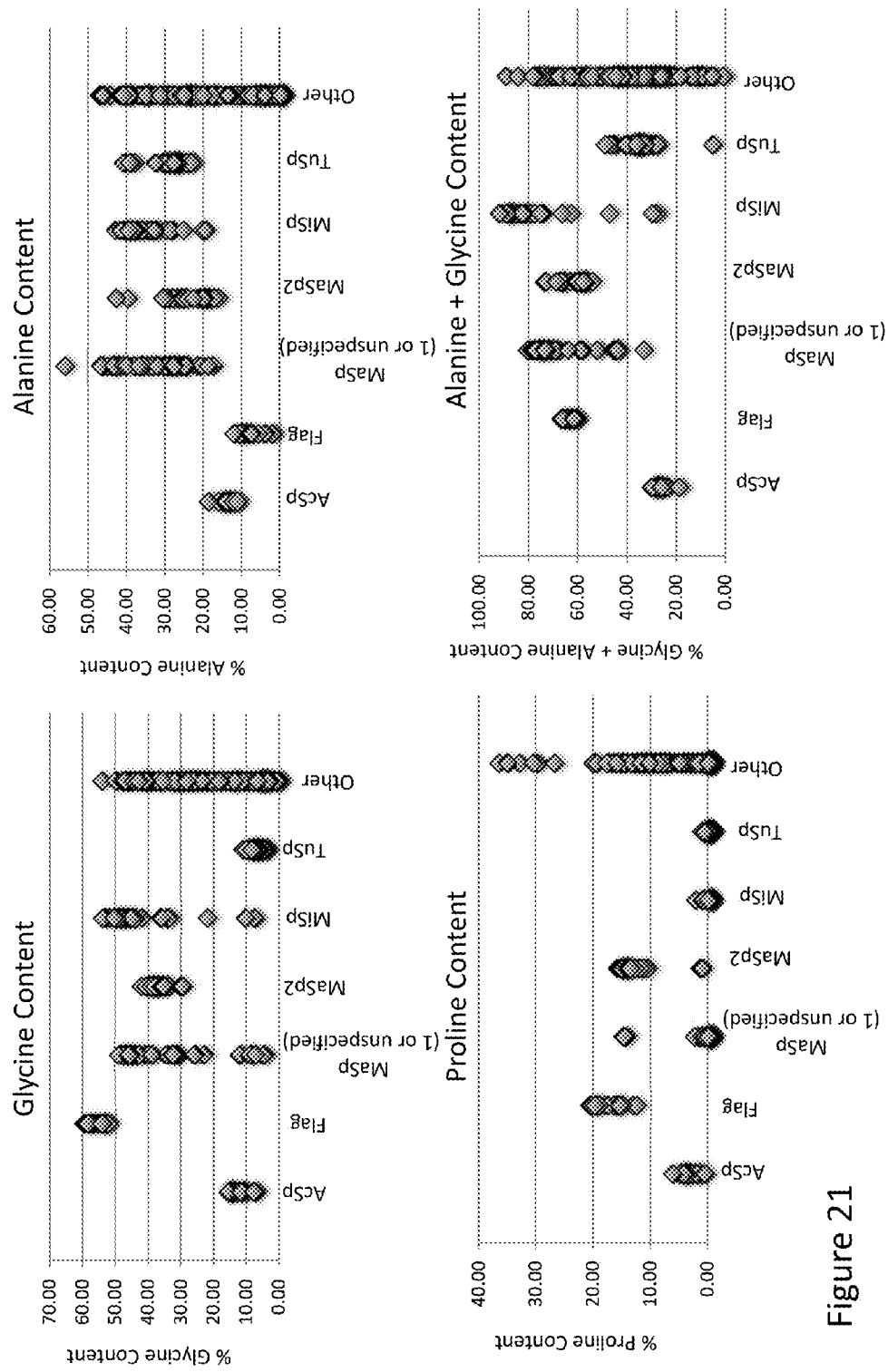
FIG. 21 illustrates graphs showing the amino acid content of various silk repeat sequences that can be expressed as block copolymers useful for the production of fibers.

Of the sequences in Tables 13a and 13b: (1) the proline content ranges from 11.35-15.74% (the percentages of Tables 13a and 13b refer to a number of amino acid residues of the specified content—in this case, proline—over a total number of amino acid residues in the corresponding polypeptide sequence). The proline content of similar R domains could also range between 13-15%, 11-16%, 9-20%, or 3-24%; (2) the alanine content ranges between 16.09-30.51%. The alanine content of similar R domains could also range between 15-20%, 16-31%, 12-40%, or 8-49%; (3) the glycine content ranges between 29.66-42.15%. The glycine content of similar R domains could also range between 38-43%, 29-43%, 25-50%, or 21-57%; (4) The glycine and alanine content ranges between 54.17-68.59%. The glycine and alanine content of similar R domains could also range between 54-69%, 48-75%, or 42-81%; (5) the β-turn content ranges between 18.22-32.16%. β-turn content is calculated using the SOPMA method from Geourjon, C., and Deleage, G., SOPMA: significant improvements in protein secondary structure prediction by consensus prediction from multiple alignments, *Comput. Appl. Biosci.*, 11:6, pg. 681-684 (1995). The SOPMA method is applied using the following parameters: window width—10; similarity threshold—10; number of states—4. The β-turn content of similar R domains could also range between 25-30%, 18-33%, 15-37%, or 12-41%; (6) the poly-alanine content ranges between 12.64-28.85%. A motif is considered a poly-alanine motif if it includes at least four consecutive alanine residues. The poly-alanine content of similar R domains could also range between 12-29%, 9-35%, or 6-41%; (7) the GPG motif content ranges between 22.95-46.67%. The GPG motif content of similar R domains could also range between 30-45%, 22-47%, 18-55%, or 14-63%; (8) the GPG and poly-alanine content ranges between 42.21-73.33%. The GPG and poly-alanine content of similar R domains could also range between 25-50%, 20-60%, or 15-70%. Other silk types exhibit different ranges of amino acid content and other properties. FIG. 21 shows ranges of glycine, alanine, and proline content for various silk types of the silk polypeptide sequences disclosed herein. FIG. 21 illustrates percentages of glycine, alanine, or proline amino acid residues over a total number of residues in the polypeptide sequences.

The resulting product of the concatenation comprising 4 repeat sequences, an alpha mating factor, and a 3× FLAG domain is digested with AscI and SbfI to release the desired silk sequence and ligated into expression vectors RM812 (SEQ ID N: 2701), RM837 (SEQ ID NO: 2702), RM814 (SEQ ID NO: 2703), and RM815 (SEQ ID NO: 2704) (key attributes of the expression vectors are summarized in Table 9) that have been digested with AscI and SbfI. A strain containing 4 copies of the silk polynucleotide under the transcriptional control of pGCW14 is generated by serially transforming *Pichia* (*Komagataella*) *pastoris* strain GS115 (NRRL Y15851) with the resulting expression vectors (after linearizing them with BsaI) using the PEG method. Similar quasi-repeat domains can range between 500-5000, 119-1575, 300-1200, 500-1000, or 900-950 amino acids in length. The entire block co-polymer can range between 40-400, 12.2-132, 50-200, or 70-100 kDa.

TABLE 13a

Properties of selected R domains

| 1x Repeat Domain Amino Acid SEQ ID NO | 1x Repeat Domain DNA SEQ ID NO | Alpha Mating Factor + 4x Repeat Domain + 3xFLAG Amino Acid SEQ ID NO | Alpha Mating Factor + 4x Repeat Domain + 3xFLAG DNA SEQ ID NO | % Proline | % Alanine | % Glycine | % Glycine + Alanine |
|---|---|---|---|---|---|---|---|
| 1313 | 382 | 2752 | 2777 | 14.22 | 21.10 | 38.07 | 59.17 |
| 1314 | 383 | 2753 | 2778 | 14.75 | 20.86 | 37.77 | 58.63 |
| 1315 | 384 | 2754 | 2779 | 14.74 | 18.33 | 39.84 | 58.17 |
| 1316 | 385 | 2755 | 2780 | 14.91 | 18.42 | 39.91 | 58.33 |
| 1317 | 386 | 2756 | 2781 | 14.79 | 18.68 | 39.69 | 58.37 |
| 1318 | 387 | 2757 | 2782 | 14.12 | 19.22 | 40.78 | 60.00 |
| 1319 | 388 | 2758 | 2783 | 14.68 | 18.65 | 39.68 | 58.33 |
| 1320 | 389 | 2759 | 2784 | 14.56 | 16.09 | 42.15 | 58.24 |
| 1321 | 390 | 2760 | 2785 | 14.73 | 18.99 | 39.53 | 58.53 |
| 1328 | 397 | 2761 | 2786 | 15.00 | 20.71 | 38.57 | 59.29 |
| 1329 | 398 | 2762 | 2787 | 14.29 | 20.71 | 38.57 | 59.29 |
| 1331 | 400 | 2763 | 2788 | 14.39 | 20.14 | 38.13 | 58.27 |
| 1335 | 404 | 2764 | 2789 | 11.86 | 30.51 | 29.66 | 60.17 |
| 1336 | 405 | 2765 | 2790 | 12.72 | 24.12 | 35.96 | 60.09 |
| 1337 | 406 | 2766 | 2791 | 13.52 | 22.54 | 35.25 | 57.79 |
| 1340 | 409 | 2767 | 2792 | 11.35 | 20.09 | 37.99 | 58.08 |
| 1370 | 439 | 2768 | 2793 | 15.74 | 17.13 | 37.04 | 54.17 |
| 1373 | 442 | 2769 | 2794 | 15.56 | 26.67 | 40.00 | 66.67 |
| 1374 | 443 | 2770 | 2795 | 14.22 | 28.89 | 38.22 | 67.11 |
| 1375 | 444 | 2771 | 2796 | 14.35 | 26.85 | 39.35 | 66.20 |
| 1376 | 445 | 2772 | 2797 | 15.18 | 26.79 | 39.29 | 66.07 |
| 1378 | 447 | 2773 | 2798 | 14.44 | 27.81 | 39.04 | 66.84 |
| 1379 | 448 | 2774 | 2799 | 14.94 | 25.86 | 40.80 | 66.67 |
| 1380 | 449 | 2775 | 2800 | 14.10 | 29.49 | 39.10 | 68.59 |
| 1384 | 453 | 2776 | 2801 | 12.16 | 25.00 | 35.81 | 60.81 |

TABLE 13b

Properties of selected R domains

| 1x Repeat Domain Amino Acid SEQ ID NO | 1x Repeat Domain DNA SEQ ID NO | Alpha Mating Factor + 4x Repeat Domain + 3xFLAG Amino Acid SEQ ID NO | Alpha Mating Factor + 4x Repeat Domain + 3xFLAG DNA SEQ ID NO | % Beta Turn | % Poly alanine | % GPG motif | % GPG + Poly Alanine | MW |
|---|---|---|---|---|---|---|---|---|
| 1313 | 382 | 2752 | 2777 | 28.44 | 17.89 | 27.52 | 45.41 | 76044 |
| 1314 | 383 | 2753 | 2778 | 30.22 | 17.63 | 28.06 | 45.68 | 95860 |
| 1315 | 384 | 2754 | 2779 | 30.68 | 15.54 | 32.27 | 47.81 | 86818 |
| 1316 | 385 | 2755 | 2780 | 28.51 | 14.91 | 31.58 | 46.49 | 79731 |
| 1317 | 386 | 2756 | 2781 | 28.79 | 15.56 | 32.68 | 48.25 | 89297 |
| 1318 | 387 | 2757 | 2782 | 32.16 | 16.08 | 30.59 | 46.67 | 88136 |
| 1319 | 388 | 2758 | 2783 | 30.56 | 15.87 | 32.14 | 48.02 | 87103 |
| 1320 | 389 | 2759 | 2784 | 28.74 | 12.64 | 31.03 | 43.68 | 90778 |
| 1321 | 390 | 2760 | 2785 | 28.68 | 15.89 | 32.56 | 48.45 | 89582 |
| 1328 | 397 | 2761 | 2786 | 31.43 | 17.86 | 32.14 | 50.00 | 49712 |
| 1329 | 398 | 2762 | 2787 | 29.29 | 17.86 | 30.00 | 47.86 | 49836 |
| 1331 | 400 | 2763 | 2788 | 29.50 | 17.27 | 30.22 | 47.48 | 49672 |

TABLE 13b-continued

Properties of selected R domains

| 1x Repeat Domain Amino Acid SEQ ID NO | 1x Repeat Domain DNA SEQ ID NO | Alpha Mating Factor + 4x Repeat Domain + 3xFLAG Amino Acid SEQ ID NO | Alpha Mating Factor + 4x Repeat Domain + 3xFLAG DNA SEQ ID NO | % Beta Turn | % Poly alanine | % GPG motif | % GPG + Poly Alanine | MW |
|---|---|---|---|---|---|---|---|---|
| 1335 | 404 | 2764 | 2789 | 18.22 | 24.58 | 25.42 | 50.00 | 83965 |
| 1336 | 405 | 2765 | 2790 | 25.00 | 19.74 | 30.26 | 50.00 | 80845 |
| 1337 | 406 | 2766 | 2791 | 22.54 | 18.85 | 22.95 | 42.21 | 87160 |
| 1340 | 409 | 2767 | 2792 | 20.09 | 16.59 | 27.51 | 44.10 | 81149 |
| 1370 | 439 | 2768 | 2793 | 26.85 | 15.28 | 40.28 | 55.56 | 77581 |
| 1373 | 442 | 2769 | 2794 | 25.78 | 26.67 | 46.67 | 73.33 | 76502 |
| 1374 | 443 | 2770 | 2795 | 26.67 | 28.00 | 42.67 | 70.67 | 75716 |
| 1375 | 444 | 2771 | 2796 | 24.07 | 26.39 | 43.06 | 69.44 | 73742 |
| 1376 | 445 | 2772 | 2797 | 28.12 | 26.34 | 44.20 | 70.54 | 76433 |
| 1378 | 447 | 2773 | 2798 | 24.60 | 27.27 | 43.32 | 70.59 | 63684 |
| 1379 | 448 | 2774 | 2799 | 25.86 | 25.86 | 44.83 | 70.69 | 59391 |
| 1380 | 449 | 2775 | 2800 | 27.56 | 28.85 | 42.31 | 71.15 | 53049 |
| 1384 | 453 | 2776 | 2801 | 28.38 | 18.24 | 24.32 | 42.57 | 52668 |

A clone of the resulting strain is cultured according to the following conditions: the culture is grown in a minimal basal salt media, similar to one described in [http://tools.invitrogen.com/content/sfs/manuals/pichiaferm_prot.pdf] with 50 g/L of glycerol as a starting feedstock. Growth occurs in a stirred fermentation vessel controlled at 30 C, with 1 VVM of air flow and 2000 rpm agitation. pH is controlled at 3 with the on-demand addition of ammonium hydroxide. Additional glycerol is added as needed based on sudden increases in dissolved oxygen. Growth is allowed to continue until dissolved oxygen reached 15% of maximum at which time the culture is harvested, typically at 200-300 OD of cell density.

The broth from the fermenter is decellularized by centrifugation. The supernatant from the Pichia (Komagataella) pastoris culture is collected. Low molecular weight components are removed from the supernatant using ultrafiltration to remove particles smaller than the block copolymer polypeptides. The filtered culture supernatant is then concentrated up to 50x.

The fiber spinning solution is prepared by dissolving the purified and dried block copolymer polypeptide in a formic acid-based spinning solvent. Spin dopes are incubated at 35° C. on a rotational shaker for three days with occasional mixing. After three days, the spin dopes are centrifuged at 16000 rcf for 60 minutes and allowed to equilibrate to room temperature for at least two hours prior to spinning. The spin dope is extruded through a 150 μm diameter orifice into a standard alcohol-based coagulation bath. Fibers are pulled out of the coagulation bath under tension, drawn from 1 to 5 times their length, and subsequently allowed to dry as a tight hank.

At least five fibers are randomly selected from at least 10 meters of spun fibers. Fibers are tested for tensile mechanical properties using a custom instrument, which includes a linear actuator and calibrated load cell. Fibers are mounted with a gauge length of 5.75 mm and pulled at a 1% strain rate until failure. The ultimate tensile strengths of the fibers are measured to be between 50-500 MPa. Depending on which fibers are selected: the yield stress is measured to be 24-172 MPa or 150-172 MPa, the ultimate tensile strength (maximum stress) is measured to be 54-310 MPa or 150-310 MPa, the breaking strain is measured to be 2-200% or 180-200%, the initial modulus is measured to be 1617-5820 MPa or 5500-5820 MPa, and the toughness value is measured to be at least 0.5 MJ/m$^3$, at least 3.1 MJ/m$^3$, or at least 59.2 MJ/m$^3$.

The resultant forces are normalized to the fiber diameter, as measured by light microscopy. Fiber diameters are measured with light microscopy at 20× magnification using image processing software. Fiber diameters are determined as the average of at least 4-8 fibers selected randomly from at least 10 m of spun fibers. For each fiber, six measurements are made over the span of 5.75 mm Depending on which fibers are selected, the fiber diameters are measured to be between 4-100 μm, between 4.48-12.7 μm, or between 4-5 μm.

To test the β-sheet crystallinity content of the fibers, the fibers are dried overnight at room temperature. FTIR spectra are collected with a diamond ATR module from 400 cm$^{-1}$ to 4000 cm$^{-1}$ with 4 cm$^{-1}$ resolution. The amide I region (1600 cm$^{-1}$ to 1700 cm$^{-1}$) is baselined and curve fitted with Gaussian profiles at 5-6 location determined by peak locations from the second derivative of the original curve. The β-sheet content is determined as the area under the Gaussian profile at ~1620 cm$^{-1}$ and ~1690 cm$^{-1}$ divided by the total area of the amide I region. To induce β-sheet crystallinity, fibers are incubated within a humidified vacuum chamber at 1.5 Torr for at least six hours. Fiber surface morphology and cross-sections (taken by freeze fracture using liquid nitrogen) are analyzed via scanning electron microscopy. Samples are sputter coated with platinum/palladium and imaged with a Hitachi TM-1000 at 5 kV accelerating voltage.

A number of embodiments of the invention have been described. Nevertheless, it will be understood that various modifications may be made without departing from the spirit and scope of the invention.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US09963554B2). An electronic copy of the "Sequence Listing" will also be available from the USPTO upon request and payment of the fee set forth in 37 CFR 1.19(b)(3).

What is claimed is:

1. A proteinaceous block co-polymer, comprising:
   a polypeptide, the polypeptide comprising from 2 to 8 concatenated repeats of SEQ ID NO: 1396 or circularly permuted variants thereof.

2. The proteinaceous block co-polymer of claim 1, wherein the polypeptide comprises a property selected from the group consisting of an alanine composition from 12 to 40%, a glycine composition from 25 to 50%, a proline composition from 9 to 20%, a β-turn composition from 15 to 37%, a GPG amino acid motif content from 18 to 55%, and a poly-alanine amino acid motif content from 9 to 35%.

3. The proteinaceous block co-polymer of claim 1, consisting of: 3 concatenated repeats of SEQ ID NO: 1396.

4. A fiber comprising the block co-polymer of claim 1.

5. The fiber of claim 4, comprising a circular cross-section and a diameter from 4.48 to 12.7 μm.

6. The fiber of claim 4, wherein the fiber has a yield stress from 24 to 172 MPa.

7. The fiber of claim 4, wherein the fiber has a maximum stress from 54 to 310 MPa.

8. The fiber of claim 4, wherein the fiber has a breaking strain from 2 to 200%.

9. The fiber of claim 4, wherein the fiber has an initial modulus from 1617 to 5820 MPa.

10. The fiber of claim 4, wherein the fiber has a toughness value from 0.5 MJ/m$^3$ to 59.2 MJ/m$^3$.

11. A culture medium comprising a secreted block copolymer of claim 1.

* * * * *